(12) United States Patent
Miller et al.

(10) Patent No.: US 10,961,197 B2
(45) Date of Patent: Mar. 30, 2021

(54) METAL CHELATORS FOR IMAGING, THERAPEUTICS, AND BIOANALYSIS

(71) Applicant: THE BOARD OF TRUSTEES OF THE UNIVERSITY OF ILLINOIS, Urbana, IL (US)

(72) Inventors: Lawrence Miller, Chicago, IL (US); Ali Mohamadi, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 16/331,293

(22) PCT Filed: Sep. 6, 2017

(86) PCT No.: PCT/US2017/050245
§ 371 (c)(1),
(2) Date: Mar. 7, 2019

(87) PCT Pub. No.: WO2018/048879
PCT Pub. Date: Mar. 15, 2018

(65) Prior Publication Data
US 2020/0010422 A1 Jan. 9, 2020

Related U.S. Application Data

(60) Provisional application No. 62/384,478, filed on Sep. 7, 2016.

(51) Int. Cl.
*C07D 215/38* (2006.01)
*C07F 5/00* (2006.01)
*C09K 11/06* (2006.01)

(52) U.S. Cl.
CPC ............ *C07D 215/38* (2013.01); *C07F 5/003* (2013.01); *C09K 11/06* (2013.01); *C09K 2211/1014* (2013.01); *C09K 2211/1029* (2013.01); *C09K 2211/182* (2013.01)

(58) Field of Classification Search
CPC .................................................. C07D 215/38
See application file for complete search history.

(56) References Cited

U.S. PATENT DOCUMENTS

| 5,089,663 A * | 2/1992 | Mease ................... C07C 229/16 |
| | | 562/507 |
| 5,434,287 A | 7/1995 | Gansow et al. |
| 2010/0204467 A1 | 8/2010 | Lamarque et al. |
| 2016/0194690 A1 | 7/2016 | Mustaev et al. |

OTHER PUBLICATIONS

Li "Luminescent Polyaminocarboxylate Chelates of Terbium and Europium: The Effect of Chelate Structure" J. Am. Chem. Soc. 1995, 117, 8132-8138.*
Seitz "Circularly Polarized Luminescence in Enantiopure Europium and Terbium Complexes with Modular, All-Oxygen Donor Ligands." Inorganic Chemistry, 2009, 48(17), 8469-8479.*

* cited by examiner

*Primary Examiner* — David K O'Dell
(74) *Attorney, Agent, or Firm* — Thomas|Horstemeyer, LLP

(57) ABSTRACT

A variety of compounds are provided capable of chelating a metal, in particular a lanthanide such as Eu(III) and Tb(III). Luminescent complexes of the compound and a metal ion are also provided, in particular luminescent metal complexes are provided containing a lanthanide such as Eu(III) or Tb(III) and a compound described herein. In some aspects, the luminescent complexes are capable of exhibiting bright emissions with high quantum yields. Methods of making the compound are provided. Methods of using the compounds and luminescent complexes are also provided, for example for imaging and therapeutic applications.

17 Claims, 3 Drawing Sheets

METAL CHELATORS FOR IMAGING, THERAPEUTICS, AND BIOANALYSIS

CROSS-REFERENCE TO RELATED APPLICATIONS

This application is the 35 U.S.C. § 371 national stage application of PCT Application No. PCT/US2017/050245, filed Sep. 6, 2017, where the PCT claims priority to, and the benefit of, U.S. provisional application entitled "METAL CHELATORS FOR IMAGING, THERAPEUTICS, AND BIOANALYSIS" having Ser. No. 62/384,478, filed Sep. 7, 2016, both of which are herein incorporated by reference in their entireties.

STATEMENT REGARDING FEDERALLY SPONSORED RESEARCH OR DEVELOPMENT

This invention was made with government support under award R01GM081030 awarded by the National Institutes of Health. The government has certain rights in the invention.

TECHNICAL FIELD

The present disclosure generally relates to metal chelators, metal complexes formed therefrom, and methods of making and uses thereof; more specifically, exemplary aspects provide luminescent complexes formed from a metal and a chelator and methods of use for detecting the presence of an analyte in a sample.

BACKGROUND

A coordination complex is the product of a Lewis acid-base reaction in which neutral or anionic organic ligands form coordinate covalent bonds with a central metal atom or ion. Also known as metal chelators, coordination compounds are a critical component of several biomedical technologies. For example, compounds that contain coordination complexes of radioactive isotopes are used extensively in both cancer diagnostics and treatment as in vivo imaging contrast agents and for targeted radiation therapy, respectively.[30] Molecules that coordinate to Gd(III) are used as contrast agents for magnetic resonance imaging (MRI).[31-32] A particular class of coordination compounds binds to lanthanide ions like Tb(III) or Eu(III) and contain organic chromophores that act to sensitize lanthanide-centered luminescence.[33] Lanthanide luminophores have photophysical properties such as ms-scale excited state lifetimes and multiple, narrow-line emission bands that make them uniquely suited for use in high throughput screening (HTS) in drug discovery,[33] immunoassays[34] and live-cell microscopy.[35]

In order to function effectively in technological applications, metal chelators must meet a number of requirements. Firstly, they must be unimolecular constructs that can be easily conjugated to antibodies, peptides or receptor-targeting ligands. So-called bifunctional chelators (BFCs) are widely used for targeting tumors in cancer imaging and therapeutics. Secondly, they must bind to a given metal ion with high thermodynamic stability and kinetic inertness. Kinetic inertness is the propensity to retain metal when diluted to extremely low concentrations (ca. nM) in the presence of large amounts of competing chelators and other metal ions. Such conditions are prevalent in blood, tissues, cell lysates or other environments where coordination compounds are used. While kinetic stability is paramount, the ability to form the metal complex rapidly is critical for radiometal binders because many isotopes have short half-lives. Moreover, it is desirable that metal complexation occur under mild physiological conditions so that antibody conjugates or other heat- or pH-sensitive preparations can be used effectively. Thirdly, the synthetic route to preparing metal chelators must be efficient, and ideally will be adaptable so that a single molecular scaffold can be used to prepare functional complexes of a wide variety of metals with different ionic radii and coordination numbers. For luminescent lanthanide complexes, the synthetic route must allow for efficient incorporation of sensitizing chromophores.

Hundreds of differently structured chelators have been prepared, and many are used in commercial bioassays or clinically. Among the reported structures, there are a handful of basic molecular architectures, or scaffolds, that have been widely used as a basis to create a diverse array of BFCs.[30] (See FIG. 1) These scaffolds vary in the degree to which they can be adapted for binding different metal ions, and they also vary in their ability to meet the stringent requirements for clinical or commercial application. For example, diethylamine triamine pentaacetic acid (DTPA) is a flexible linear, 8-coordinate chelator, and variants of DTPA have been used clinically for MRI (with Gd). While the formation kinetics of DTPA/metal complexes are favorable, their kinetic inertness can be extremely poor. By contrast, BFCs based on 1,4,7,10-tetraazacyclododecane-1,4,7,10-tetraacetic acid (DOTA) and 1,4,7-triazacyclononane-triacetic acid (NOTA) exhibit excellent kinetic stability, and they have been used clinically for MRI and certain radiopharmaceutical applications. However, metallation of macrocycles like DOTA and NOTA analogues requires prolonged reaction at high temperatures and low pH, and this greatly limits their use with antibody conjugates or with radioisotopes with short half-lives. Other reported BFCs like Lumi4 (a luminescent Tb complex) and CHX-A"-DTPA exhibit both favorable metallation properties and good kinetic stability. However, their architecture limits their use to one or a few different metals.

Luminescent Tb(III) and Eu(III) complexes exhibit unique and useful photophysical properties including large Stokes shifts (>150 nm), long excited state lifetimes (μs-ms) and multiple, narrow emission bands (<10 nm half-maximal) that span the visible spectrum.[1-2] Time-gated detection of long-lived lanthanide emission following pulsed excitation eliminates ns-scale fluorescence background and enables the development of highly sensitive diagnostic assays, high throughput screening methods or luminescence microscopy. In addition, the multiple emission bands afford exceptional multiplexing capabilities, especially when Tb(III) or Eu(III) complexes are used as Forster Resonance Energy Transfer (FRET) donors in combination with differently colored, fluorescent acceptors.[3] To be used effectively in time-gated bio-analysis, lanthanide probes must meet several requirements including good brightness (the product of absorptivity and quantum yield of emission), strong and kinetically stable metal binding, bio-compatibility, and ease of synthesis and modification.[4]

There remains a need for a general chelator that can be easily modified structurally for use with a broad array of clinically and technologically relevant metal ions, including for Eu(III) and Tb(III), that exhibits requisite kinetic and thermodynamic metal binding stabilities, that complexes rapidly under benign physiological conditions and that can be easily appended with functional groups that enable easy conjugation to antibodies, peptides or other targeting molecules.

SUMMARY

Various solutions are provided that overcome one or more of the aforementioned deficiencies. In particular, a variety of compounds (chelators) are provided as well as luminescent complexes formed between the compounds and a metal ion. Methods of making the compounds and complexes are also provided, as are methods of using the compounds and luminescent complexes formed therefrom.

In some aspects, a class of lanthanide chelators are provided. In some aspects, the chelator is a compound according to Formula I or Formula II. In some aspects, the compound is based on cyclohexyl triethylenetetraamine hexaacetic acid (cyTTHA). In some aspects, functionalization of a central pendant carboxylic group with 7-aminoquinolinone (cs124) or 7-amino-4-trifluoromethyl-2-(1H)-quinolinone (cs124-CF3) sensitizer chromophores yielded Tb(III) and Eu(III) complexes with exceptional quantum yields in water (up to 54%), high absorptivity (>15,000 M-1 cm-1 at 365 nm), fast metal complexation rates and kinetic stability comparable to "industry standard" cryptates and macrocycles. Moreover, the modular synthesis of cyTTHA described below provides a robust scaffold for preparing multifunctional metal complexes via selective N-alkylation of the chelator backbone.

In some aspects, a compound is provided having a formula according to Formula I or Formula II below.

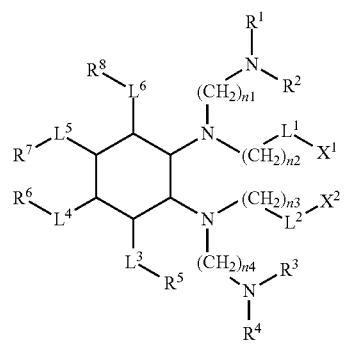

I

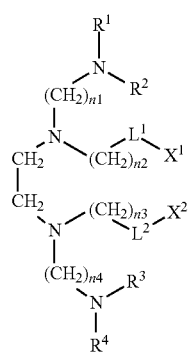

II

In some aspects, n1 and n4 are independently selected from integers of from 1 to 5, e.g. 2; and n2 and n3 are independently selected from integers of from 0 to 5, e.g. 0 or 1. In various aspects, $R^1$, $R^2$, $R^3$ and $R^4$ are independently selected from H, —$CH_2COOH$, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl, and substituted and unsubstituted heteroaryl. In some aspects, $R^1$, $R^2$, $R^3$ and $R^4$ are selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl and substituted and unsubstituted heteroaryl. In some aspects, $R^2$, $R^3$, and $R^4$ are each —$CH_2COOH$; while $R^1$ is selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl and substituted and unsubstituted heteroaryl.

In some aspects, $R^5$, $R^6$, $R^7$ and $R^8$, are independently selected from H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2OR^9$, —$OC(O)R^9$, —$C(O)NR^9R^{10}$, —$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, or $R^5$, together with the atom to which it is attached and one or more of $R^6$, $R^7$, $R^5$ forms a substituted and unsubstituted cycloalkyl, substituted and unsubstituted heterocyclyl, substituted and unsubstituted aryl, and substituted and unsubstituted heteroaryl. In some aspects, $R^5$, $R^7$ and $R^5$ are H, while $R^6$ is selected from the group consisting of H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2R^9$, —$OC(O)R^9$, —$C(O)NR^9R^{10}$—$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol.

In some aspects, $R^9$ and $R^{10}$ are independently selected from H, substituted and unsubstituted alkyl, substituted and unsubstituted aryl, substituted and unsubstituted heteroaryl and substituted and unsubstituted heterocyclyl, or $R^9$ and $R^{10}$, together with the atoms to which they are attached, form a 5- to 7 membered substituted or unsubstituted heterocyclyl or heteroaryl.

In some aspects, $L^1$, $L^2$, $L^3$, $L^4$, $L^5$, and $L^6$, are independently none (i.e. absent) or selected from substituted and unsubstituted alkyl.

In some aspects, $X^1$ and $X^2$ are independently selected from H, halogen, —CHO, —COOH, —$PO(OH)_2$, —$CONH_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, substituted and unsubstituted alkyl, substituted and unsubstituted alkynyl, substituted and unsubstituted heteroalkyl, substituted and unsubstituted cycloalkyl, substituted and unsubstituted heterocyclyl, substituted and unsubstituted aryl, substituted and unsubstituted heteroaryl, fluorophores or chromophores that absorb light of a wavelength in the range of about 300 to about 420 nm, and a group of formula III:

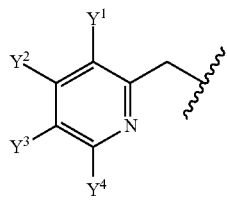

III wherein $Y^1$, $Y^2$, $Y^3$, $Y^4$ are independently selected from H, substituted and unsubstituted alkyl, halogen, CN, $CF_3$, acyl, —$SO_2NR^{11}R^{12}$, —$NR^{11}R^{12}$, —$OR^{11}$, —$SO_2R^{11}$, —$COOR^{11}$, —$SO_2OR^{11}$, —$OC(O)NR^{11}$, —$C(O)NR^{11}R^{12}$—$NR^{11}C(O)R^{12}$, —$NR^{11}SO_2R^{12}$, and —$NO_2$, or $Y^1$ together with the atom to which it is attached and one or more of $Y^2$, $Y^3$, $Y^4$ and forms a substituted and unsubstituted cycloalkyl, substituted and unsubstituted heterocyclyl, substituted and unsubstituted aryl or substituted and unsubstituted heteroaryl. In some aspects, $X^1$ and $X^2$ are each independently selected from the group consisting of —COOH, —$PO(OH)_2$, and a sensitizer so long as at least one of $X^1$ and $X^2$ is a sensitizer. In some aspects, at least one of $X^1$ and $X^2$ is —COOH. In other aspects, both $X^1$ and $X^2$ are a sensitizer.

In some aspects, $X^1$ and $X^2$ are independently selected from halogen, —$CONH_2$, —CHO, —$C(O)NHNH_2$, —COOH, maleimidyl, thiazolidyl, haloacetyl, pyridyl disulfide, substituted and unsubstituted NHS ester, sulfonated NHS ester, succinimidyl, —NCO, —NCS, —$N_3$, substituted and unsubstituted alkynyl, tetrazolyl, substituted and unsubstituted cycoloctynyl, an amino acid moiety, and a phosphoramidite moiety. In some aspects, one or both of $X^1$ and $X^2$ are independently selected from tyramine, a tyramine derivative, biotin, estrogen, trimethoprim, methotrexate, benzyl guanine, and benzyl cytosine. In some aspects, one or both of $X^1$ and $X^2$ are independently selected from 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol.

In Formula III above, $R^{11}$ and $R^{12}$ are independently selected from H, substituted and unsubstituted alkyl, substituted and unsubstituted aryl, substituted and unsubstituted heteroaryl and substituted and unsubstituted heterocyclyl, or $R^{11}$ and $R^{12}$, together with the atoms to which they are attached, are optionally joined to form a 5- to 7 membered heterocyclyl or heteroaryl;

Suitable sensitizers can include, for example,

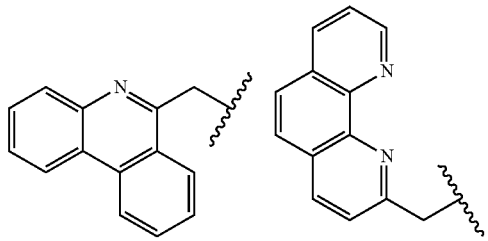

-continued

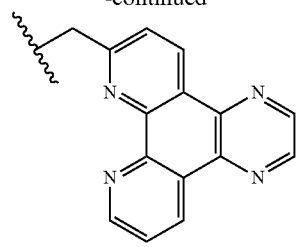

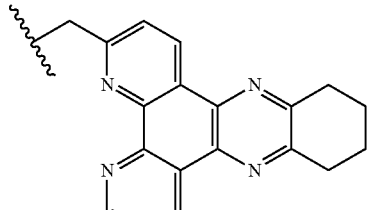

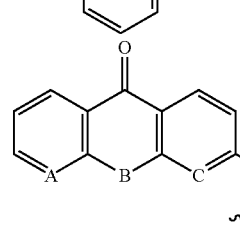

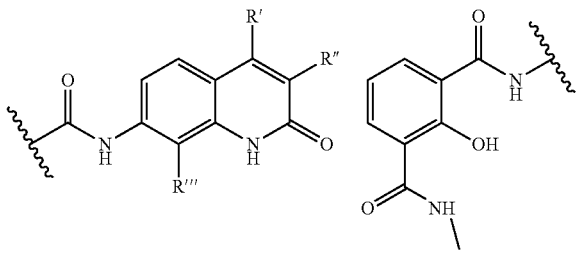

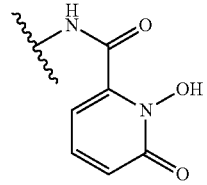

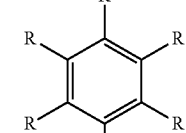

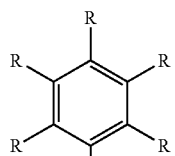

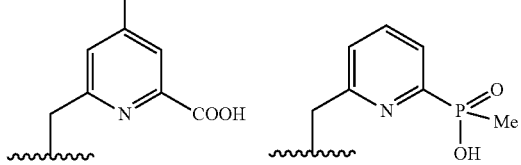

-continued

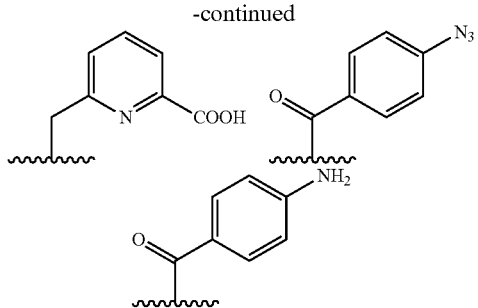

where A and C are independently selected from N and CH; R is independently selected at each occurrence from H and —OCH$_3$; R' is selected from —CH$_3$, —CF$_3$, and —CH$_2$COOH; R" is selected from H and —CH$_2$COOH; and R''' is selected from H and —CH$_3$. In some aspects, each occurrence of the sensitizer has a formula according to

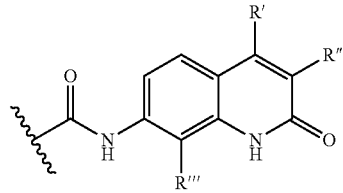

where R', R", and R''' are as defined above.

In some aspects, the compound is

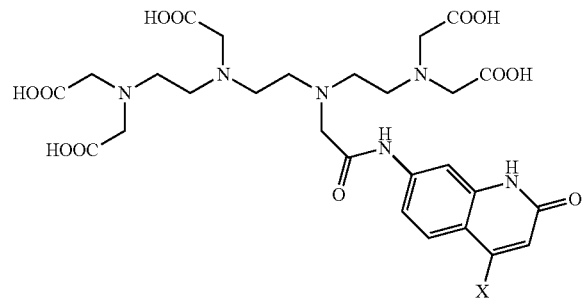

where X is CH$_3$ or CF$_3$.

In some aspects, the compound is

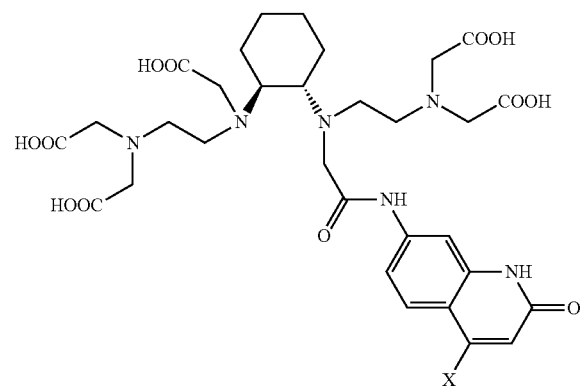

where X is CH$_3$ or CF$_3$.

In some aspects, the compound is

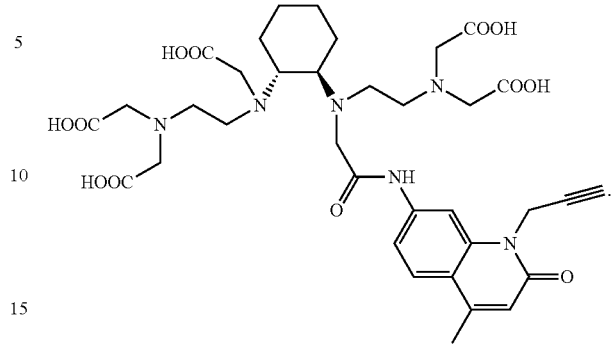

In some aspects, the compound is

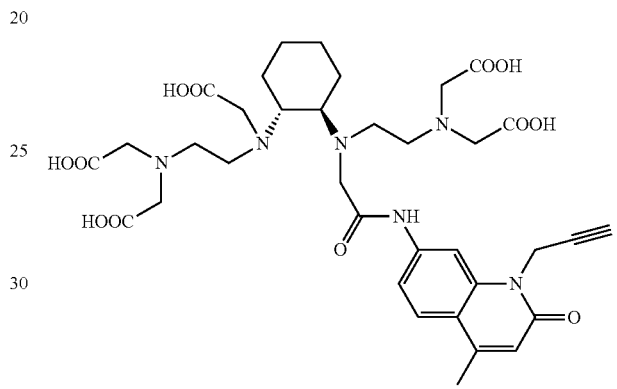

In some aspects, the compound is

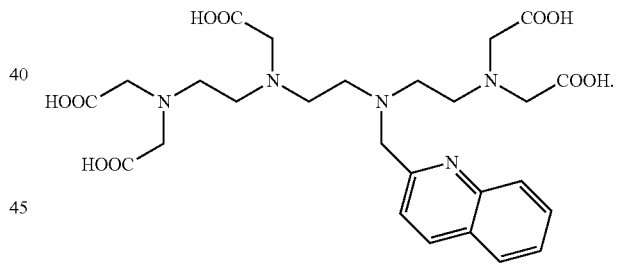

In some aspects, the compound is selected from the group consisting of

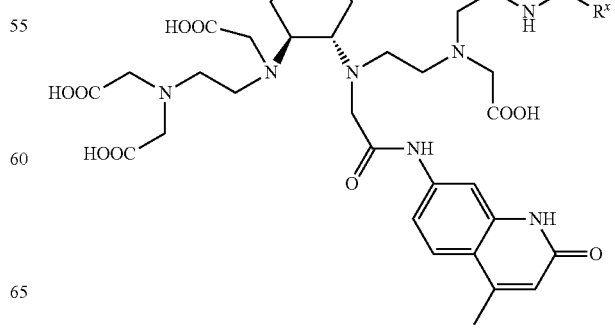

-continued
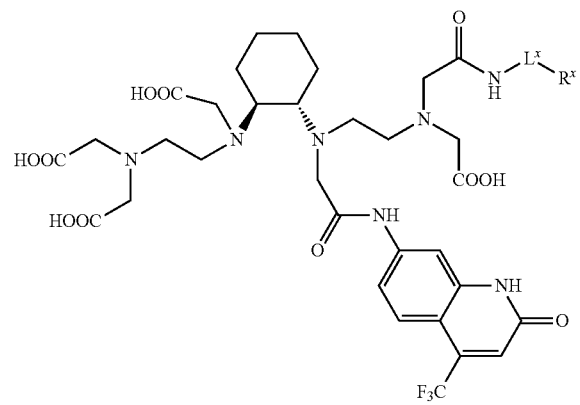
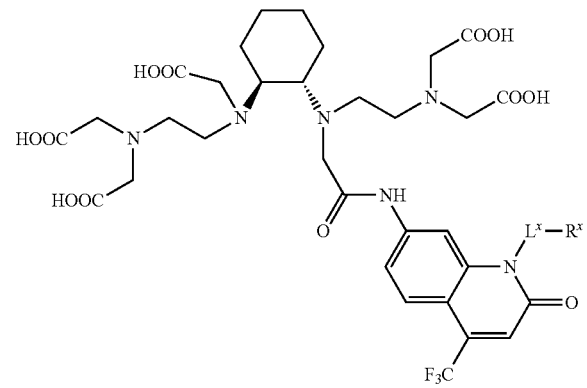
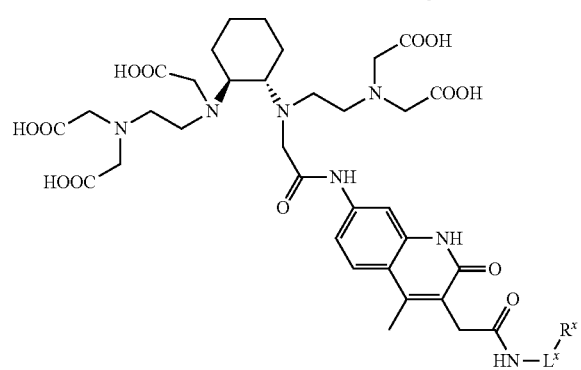
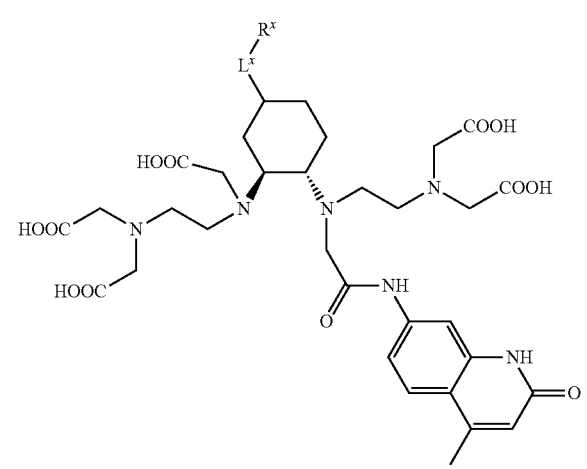
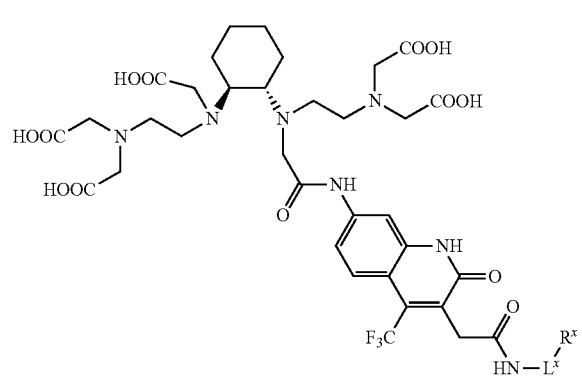
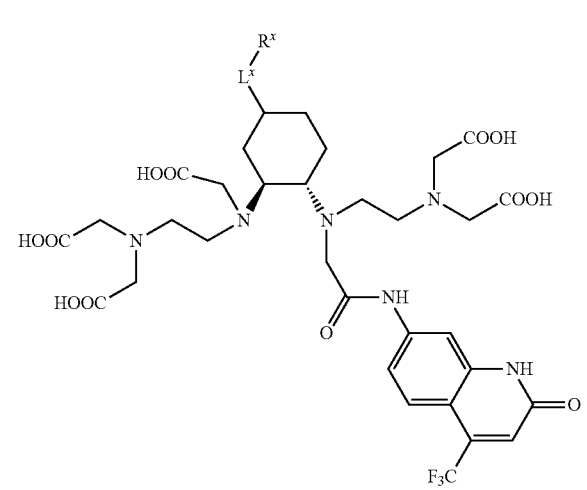

-continued

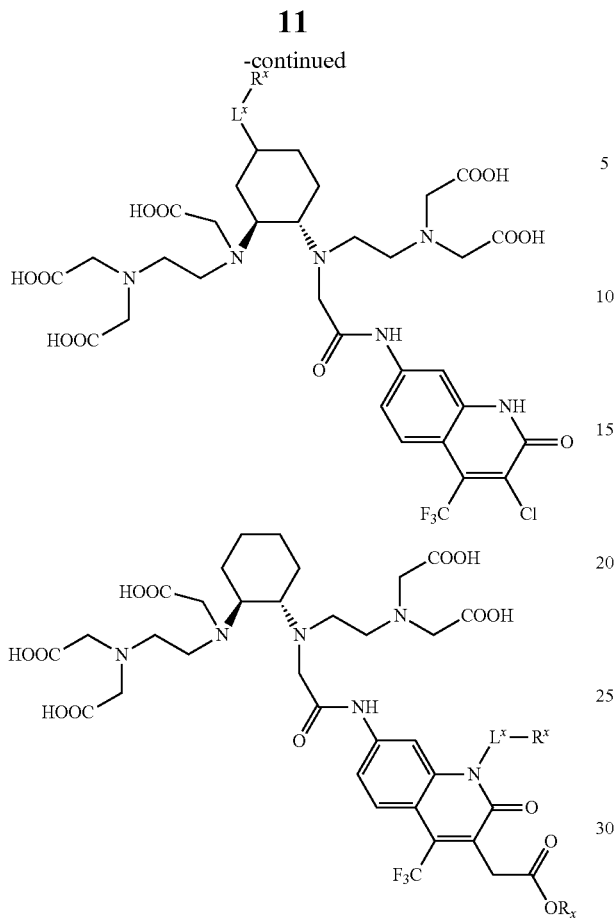

In the above formulas, $L^x$ is independently selected at each occurrence from none, substituted and unsubstituted alkyl, substitute and unsubstituted heteroalkyl, substituted and unsubstituted heteroaryl, and substituted and unsubstituted heterocycloalkyl. In some aspects, $L^x$ has about 3 to 30 carbon atoms, about 3 to 20 carbon atoms, about 6 to 20 carbon atoms, or about 6 to 12 carbon atoms.

In the above formulas, $R^x$ is independently selected at each occurrence from H, a halogen, substituted and unsubstituted alkyl, substituted and unsubstituted heteroalkyl, substituted and unsubstituted heteroaryl, substituted and unsubstituted heterocycloalkyl. In some aspects, Rx is independently selected at each occurrence from the following group

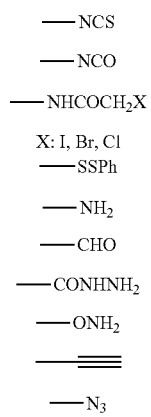

-continued

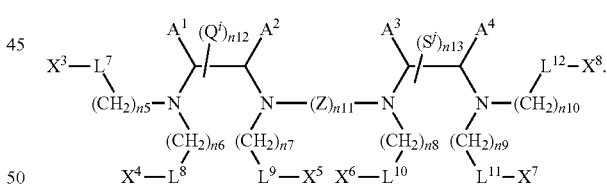

In some aspects, the compound is a compound according to Formula VIII:

$$X^3-L^7\underset{(CH_2)_{n5}}{\overset{A^1\ (Q^i)_{n12}\ A^2}{\diagup\!\!\!\diagdown}}N-(Z)_{n11}-N\underset{(CH_2)_{n8}\ (CH_2)_{n9}}{\overset{A^3\ (S^j)_{n13}\ A^4}{\diagup\!\!\!\diagdown}}\underset{(CH_2)_{n10}}{\diagdown}L^{12}-X^8.$$
$$X^4-L^8\quad L^9-X^5\ X^6-L^{10}\quad L^{11}-X^7$$

In the above formula, $A^1$ and $A^2$ form together with the atoms to which they are attached a $C_3$-$C_8$-cycloalkyl group. In the above formula, $A^3$ and $A^4$ form together with the atoms to which they are attached a $C_3$-$C_8$-cycloalkyl group. In the above, Z is selected from the group consisting of —CH$_2$—, —CH$_2$CH$_2$—, —CH$_2$CH$_2$OCH$_2$CH$_2$—, and —CH$_2$CH$_2$SCH$_2$CH$_2$—.

In the above formula, n5, n6, n7, n8, n9 and n10 are integers. In some aspects, n5, n6, n7, n8, n9 and n10 are independently selected from integers from 0 to 5 or from 0 to 3 inclusive. In some aspects, n11 is selected from integers from 1 to 10, from 1 to 5, or from 5 to 10 inclusive. In some aspects, n12 and n13 are independently selected from integers of from 1 to 16, from 1 to 5, from 6 to 10, or from 11 to 16 inclusive. In some aspects, i is an integer selected from integers of from 1 to n12 inclusive; and j is selected from integers of from 1 to n13 inclusive.

In the above formula, $nQ^i$ and $S^j$ are independently R, $R^i$ or $R^j$, where R, $R^i$ and $R^j$ are independently selected from substituted and unsubstituted alkyl, halogen, CN, $CF_3$, acyl, —$SO_2NR'R''$, —NR'R'', —OR', —$SO_2R'$, —COOR', —$SO_2OR'$, —OC(O)R', —C(O)NR'R'—NR'C(O)R'', —$NR'SO_2R''$, —$NO_2$, —C(O)$NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol or $R^i$, together with the atom to which it is attached and one or more additional $R^i$, forms a substituted and unsubstituted cycloalkyl, substituted and unsubstituted heterocyclyl, substituted and unsubstituted aryl or substituted and unsubstituted heteroaryl, or $R^j$, together with the atom to which it is attached and one or more additional $R^j$ forms a substituted and unsubstituted cycloalkyl, substituted and unsubstituted heterocyclyl, substituted and unsubstituted aryl, and substituted and unsubstituted heteroaryl. In the above, R' and R'' are independently selected from H, substituted and unsubstituted alkyl, substituted and unsubstituted aryl, substituted and unsubstituted heteroaryl, and substituted and unsubstituted heterocyclyl;

In the above, $L^7$, $L^8$, $L^9$, $L^{10}$, $L^{11}$, and $L^{12}$ are independently absent, H or selected from substituted and unsubstituted heteroalkyl, and substituted and unsubstituted alkyl. In the above, $X^3$, $X^4$, $X^5$, $X^6$, $X^7$ and $X^8$ are independently selected from H, halogen, —CHO, —COOH, —PO(OH)$_2$, —CONH$_2$, —C(O)NHNH$_2$, —NCO, —NCS, —N$_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, substituted and unsubstituted alkyl, substituted and unsubstituted alkynyl, substituted and unsubstituted cycloalkyl, substituted and unsubstituted heterocyclyl, substituted and unsubstituted aryl, substituted and unsubstituted heteroaryl, fluorophores or chromophores that absorb light of a wavelength in the range of about 300 to about 420 nm, and compounds according to formula IX:

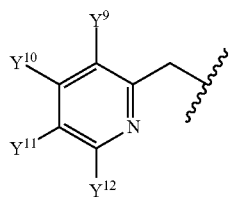

IX

In compound IX, $Y^9$, $Y^{10}$, $Y^{11}$, $Y^{12}$ are independently selected from H, substituted and unsubstituted alkyl, halogen, CN, $CF_3$, acyl, —$SO_2NR^{13'}R^{13''}$, —$NR^{13'}R^{13''}$, —$OR^{13'}$, —$SO_2R^{13'}$, —$COOR^{13'}$, —$SO_2OR^{13'}$, —$OC(O)R^{13'}$, —$C(O)NR^{13'}R^{13''}$, —$NR^{13'}C(O)R^{13''}$, —$NR^{13'}SO_2R^{13''}$, and —$NO_2$, or $Y^9$ together with the atom to which it is attached and one or more of $Y^{10}$, $Y^{11}$, $Y^{12}$ and forms a substituted and unsubstituted cycloalkyl, substituted and unsubstituted heterocyclyl, substituted and unsubstituted aryl or substituted, and unsubstituted heteroaryl, where $R^{13'}$ and $R^{13''}$ are independently selected from H, substituted and unsubstituted alkyl, substituted and unsubstituted aryl, substituted and unsubstituted heteroaryl and substituted, and unsubstituted heterocyclyl.

In some aspects, the compound is a compound according to Formula IX where at least one of $X^3$, $X^4$, $X^5$, $X^6$, $X^7$ and $X^5$ is the fluorophore or chromophore that absorbs light of a wavelength in the range of about 300 to about 420 nm, and the fluorophore or chromophore is selected from the group consisting of

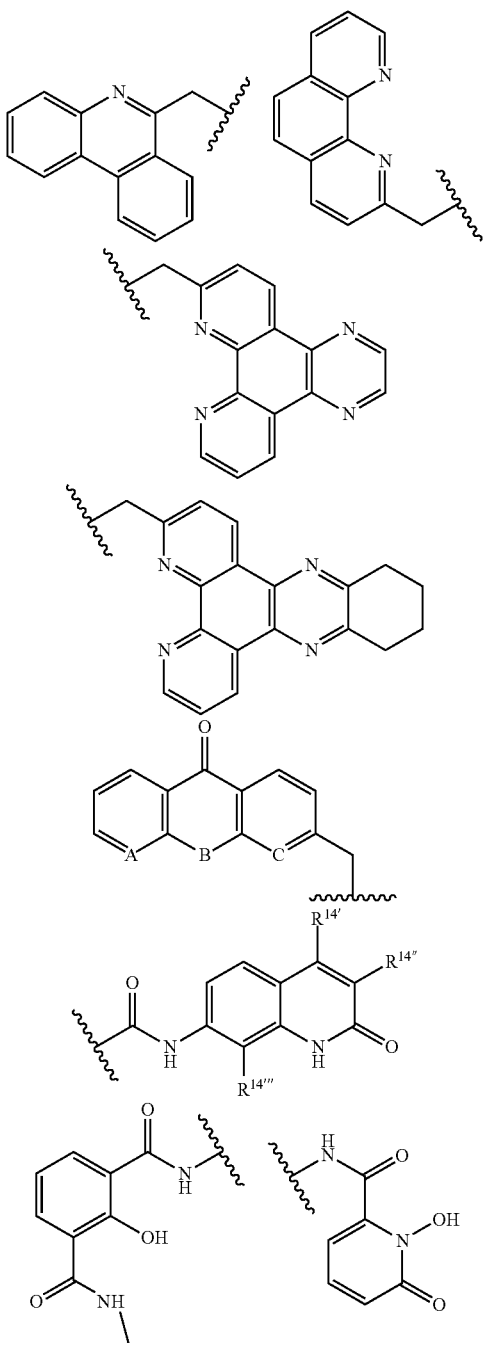

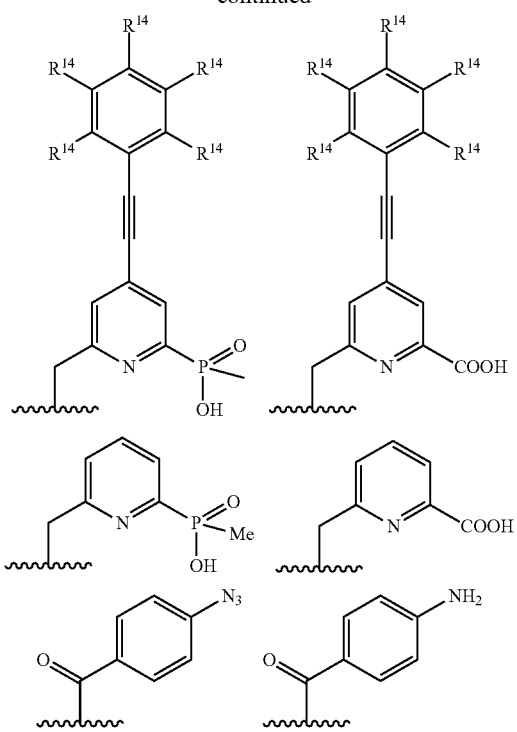

wherein A and C are independently selected from N and CH; wherein $R^{14}$ is independently selected at each occurrence from H and —OCH$_3$; wherein $R^{14'}$ is selected from —CH$_3$, —CF$_3$, and —CH$_2$COOH; wherein $R^{14'''}$ is selected from H and —CH$_2$COOH; and wherein $R^{14''''}$ is selected from H and —CH$_3$.

In some aspects, the compound is a compound according to Formula IX where the fluorophore or chromophore is a compound of formula:

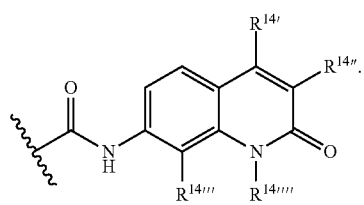

wherein $R^{14'}$, $R^{14'''}$, and $R^{14''''}$ are as in Claim 7; and wherein $R^{14''''}$ is selected from H and —CH$_3$.

In some aspects, the compound is selected from the group consisting of

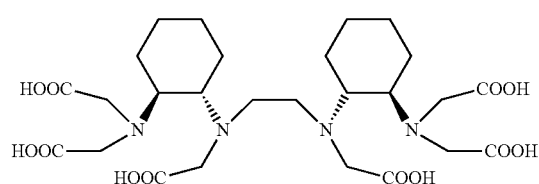

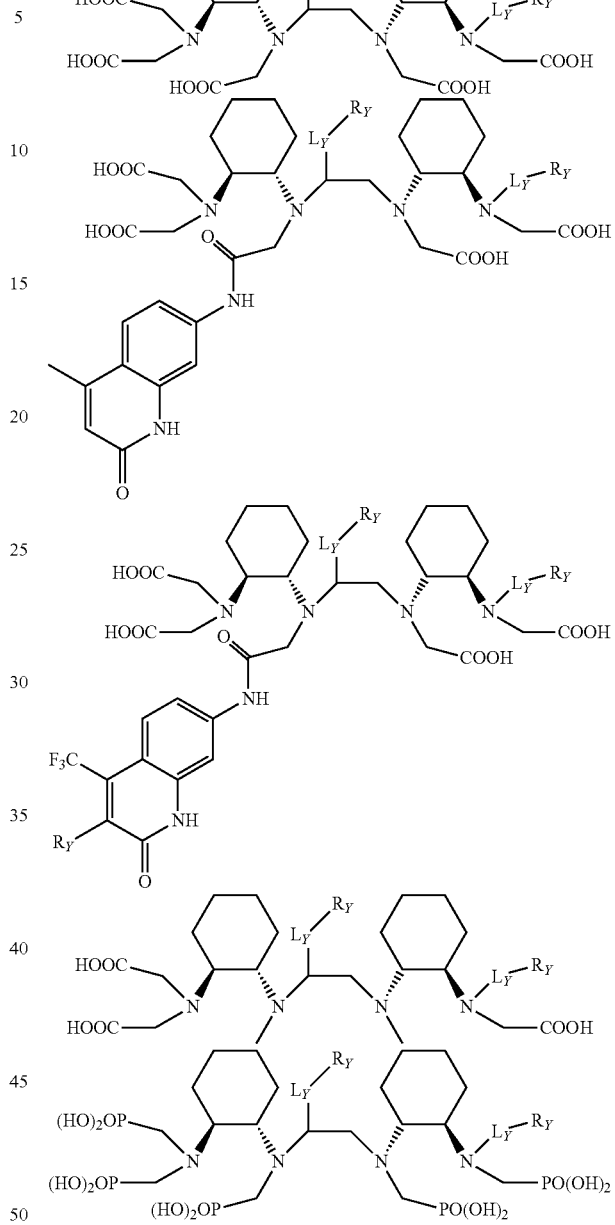

where $L_Y$ is independently at each occurrence selected from the group consisting of none, substituted and unsubstited alkyl, substituted and unsubstited heteroalkyl, substituted and unsubstited heteroaryl, and substituted and unsubstited heterocycloalkyl; and where $R_Y$ is independently at each occurrence selected from the group consisting of hydrogen, a halogen, substituted and unsubstited alkyl, substituted and unsubstited heteroalkyl, substituted and unsubstited heteroaryl, and substituted and unsubstited heterocycloalkyl.

In some aspects, $R_Y$ is selected from the group consisting of

—NCS

-continued

—NCO

—NHCOCH₂X

X: I, Br, Cl

—SSPh

—NH₂

—CHO

—CONHNH₂

—ONH₂

—≡

—N₃

—SO₂Cl

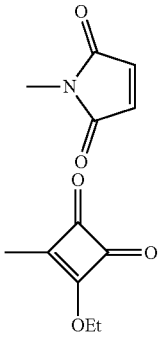

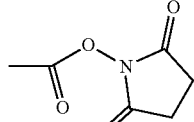

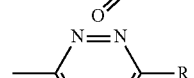

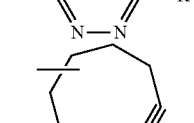

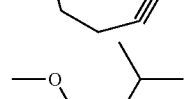

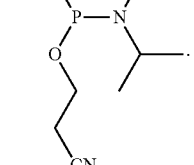

Luminescent complexes are also provided. High brightness at relatively long excitation wavelengths is useful to minimize inner filter effects in bioassays, and it is critical for time-gated, luminescence microscopy because conventional optics do not effectively transmit below 350 nm.[4-5] However, 1:1 ligand:metal complexes with brightness values exceeding 5000 $M^{-1}$ $cm^{-1}$ above 350 nm are rare.[6-7] Disclosed herein are protein-targeted Tb(III) labels that can be used for intracellular, time-gated imaging.[8-11] These efforts have leveraged the exceptionally bright (QY, 54%) and kinetically stable Lumi4 Tb(III) complex which is compatible with the 365 nm LED excitation source of our microscope ($\varepsilon_{365}$, ca. 8500 $M^{-1}$ $cm^{-1}$).[6]

The luminescent complexes provided herein include a complex formed between a compound described herein and a metal atom or ion. In some aspects, the metal ion is a lanthanide. In some aspects, the metal ion is Eu(III) or Tb(III). The metal ion can include any stable or any radioactive isotope of a metal selected from the group consisting of Ga, In, Tl, La, Ce, Pr, Nd, Pm, Sm, Eu, Gd, Tb, Dy, Ho, Er, Tm, Yb, Lu, Sc, Y, Ti, Zr, Cr, Mn, Tc, Re, Fe, Ru, Co, Rh, Ir, Ni, Pd, Pt, Cu, Zn, Cd, Hg, Al, Ge, Sn, Pb, Sb, Bi, Te, Po, Mg, Ca, Sr, Ba, Ra, Ac, Th and U. The metal ion can include a metal ion selected from the group consisting of $^{66}$Ga, $^{67}$Ga, $^{68}$, $^{111}$In, $^{201}$Tl, $^{142}$Pr, $^{149}$Pm, $^{153}$Sm, $^{153}$Gd, $^{159}$Gd, $^{166}$Ho, $^{175}$Yb, $^{177}$Lu, $^{47}$Sc, $^{90}$Y, $^{89}$Zr, $^{51}$Cr, $^{99m}$Tc, $^{188}$Re, $^{186}$Re, $^{57}$Co, $^{101m}$Rh, $^{62}$Cu, $^{64}$Cu, $^{67}$Cu, $^{117m}$Sn, $^{203}$Pb, $^{212}$Pb, $^{212}$Bi, $^{213}$Bi, $^{223}$Ra, and $^{225}$Ac.

Various methods of making the compounds herein are also provided. In some aspects, the methods include a modular synthesis that follows a general reaction scheme of N-benzyl protection, N-alkylation with an alkyl halide, benzyl deprotection via hydrogenation, a second alkyl halide N-alkylation, and finally a sensitizer installation via a third alkylation.

In various aspects, methods of making the compounds are provided that include (i) alkylating a compound according to Formula I-C or Formula II-C with a compound according to Formula IV to produce a first intermediate; (ii) alkylating the first intermediate with a compound according to Formula V to produce a second intermediate; and (iii) deprotecting the second intermediate to produce the compound according to Formula I or Formula II. In some aspects, the first alkylating step, the second alkylating step, or both alkylating steps are performed at about room temperature, e.g. about 65° C. to 75° C.

The compound according to Formula I-C and Formula II-C are

I-C

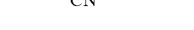

II-C

The compounds according to Formula IV and Formula V are

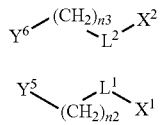
IV

V

In some aspects, the method further includes (a) alkylating a compound according to Formula I-B or Formula II-B with one or both of a compound according to Formula VI and a compound according to Formula VII followed by benzyl deprotection via hydrogenation to produce the compound according to Formula I-C or Formula II-C. The step of alkylating the compound according to Formula I-B or Formula II-B can be performed at a temperature of about 60° C., e.g. about 55° C. to 65° C.

The compounds according to Formula I-B and Formula II-B are:

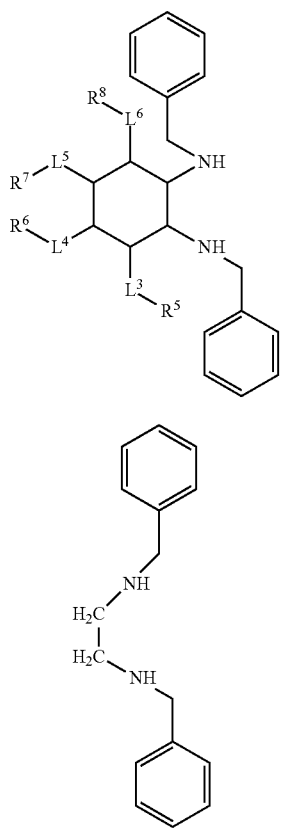

I-B

II-B

The compounds according to Formula VI and VII are

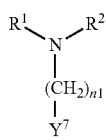

VI

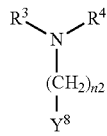

VII

In the above formulas, $Y^7$ and $Y^8$ are each independently a halogen, preferably Br. In the above formulas, $Y^5$ and $Y^6$ are each independently a halogen such as Cl or Br, preferably Cl. In the above formula, n1, n2, n3, and n4 are as defined above; and $L^1$, $L^2$, $L^3$, $L^4$, $L^5$ and $L^6$, are as defined elsewhere herein.

In the above formulas, $R^1$, $R^2$, $R^3$ and $R^4$ are as defined elsewhere herein, except that the $R^1$, $R^2$, $R^3$ and $R^4$ can be protected with one or more protecting groups to protect from unwanted alkylation during the alkylation steps. For example, in some aspects the $R^1$, $R^2$, $R^3$ or $R^4$ include a carboxylic acid that is protected with a suitable carboxylic acid protecting group, e.g. a methyl ester, a benzyl ester, or a tert-butyl ester. In some aspects, one or more (sometime all) of $R^1$, $R^2$, $R^3$, and $R^4$ are each —CH$_2$COOtBu.

In the above formulas, $R^5$, $R^6$, $R^7$ and $R^8$ are as defined elsewhere herein, except that the $R^5$, $R^6$, $R^7$ and $R^8$ can be protected with one or more protecting groups to protect from unwanted alkylation during the alkylation steps. For example, in some aspects the $R^5$, $R^6$, $R^7$ and $R^8$ include a carboxylic acid that is protected with a suitable carboxylic acid protecting group, e.g. a methyl ester, a benzyl ester, or a tert-butyl ester.

In the above formulas, $R^9$ and $R^{16}$ are as defined elsewhere herein, except that $R^9$ and $R^{10}$ can be protected with one or more protecting groups to protect from unwanted alkylation during the alkylation steps. For example, in some aspects the $R^9$ and $R^{10}$ include a carboxylic acid that is protected with a suitable carboxylic acid protecting group, e.g. a methyl ester, a benzyl ester, or a tert-butyl ester.

In some aspects, a method is provided for detecting the presence of an analyte in a sample. The sample can be a living sample, for example the sample can be a human. The sample can include tissue such as muscles or organs. The method can include (a) contacting the sample with a composition comprising a luminescent complex described herein, (b) exciting the complex; and (c) detecting luminescence from the complex.

In some aspects, a method is provided for detecting the presence of an analyte in a sample, the method including: (a) contacting the sample and a composition comprising a luminescent complex according to any one of claims 12-14 and a luminescence modifying group; (b) exciting the complex; and (c) determining a luminescent property of the sample; wherein energy is transferred between the luminescent complex and the luminescence modifying group when the complex is excited; and wherein the presence of the analyte results in a change in the luminescent property. The complex and the luminescence modifying group can be part of the same molecule or they can be part of different molecules.

Other systems, methods, features, and advantages of compound, luminescent complexes, and methods of making and used thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
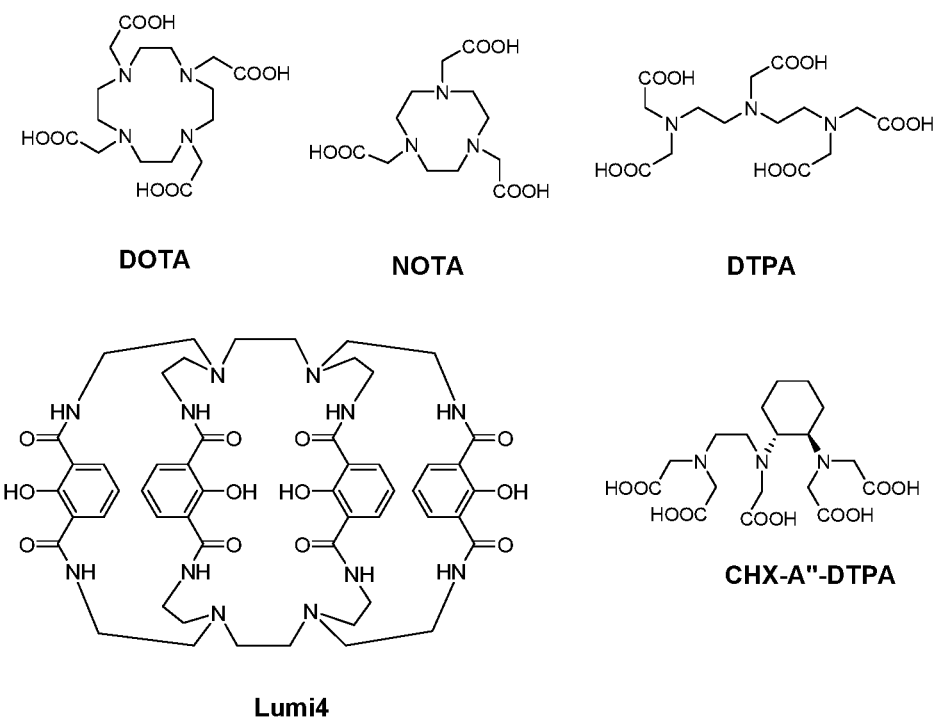
FIG. 1 is a figure of chelators used in various commercial or clinical applications.

In various aspects, modular synthetic strategies are provided allowing for the facile synthesis of a series of compounds (metal chelators) capable of forming luminescent complexes with a variety of metals. In particular, the compounds are suitable for chelating with lanthanide metals such as Eu(III) and Tb(III) to form luminescent complexes with exceptional brightness and stability needed for time-gated biosensing and microscopy applications.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of organic chemistry, analytical chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

"Alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl. In some aspects, alkenyl contains from 2 to 8 carbon atoms, from 2 to 6 carbon atoms, from 3 to 8 carbon atoms, or from 4 to 8 carbon atoms.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" means a straight or branched chain hydrocarbon containing from 1 to 10 carbon atoms unless otherwise specified. An alkyl chain may incorporate one or more O, S or NH groups, e.g. and ethylene glycol or poly(ethylene glycol) group. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to, —CH$_2$—, —CH$_2$CH$_2$—, —CH$_2$CH$_2$CHC(CH$_3$)—, and —CH$_2$CH(CH$_2$CH$_3$)CH$_2$—. In some aspects, alkyl contains 1, 2, 3, 4, 5, 6, 7, 8, 9, or 10 carbon atoms.

"Alkynyl" means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl. In some aspects, alkynyl contains from 2 to 8 carbon atoms, from 2 to 6 carbon atoms, from 3 to 8 carbon atoms, or from 4 to 8 carbon atoms.

"Amino acid," as used herein, refers to the twenty conventional amino acids. Stereoisomers (e.g., D-amino acids) of the twenty conventional amino acids, unnatural amino acids such as α-, α-disubstituted amino acids, N-alkyl amino acids, and other unconventional amino acids may also be suitable components for the compound of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline).

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl can be attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain aspects, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. In certain aspects of the disclosure, the aryl group is phenyl or naphthyl. In certain other aspects, the aryl group is phenyl.

"Cyano" and "nitrile" mean a —CN group.

The term "cycloalkyl," as used herein, means a monocyclic or a bicyclic alkyl ring system. Monocyclic ring systems are cyclic hydrocarbon groups containing from 3 to 8 carbon atoms, where such groups can be saturated or unsaturated, but not aromatic. In certain aspects, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain aspects, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In certain aspects of the disclosure, the cycloalkyl is cyclopentyl, cyclohexyl, or cycloheptyl, "Halo" or "halogen" mean —Cl, —Br, —I or —F. In certain aspects, "halo" or "halogen" refers to —Cl or —F.

"Haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl. In certain aspects, each "haloalkyl" is a fluoroalkyl, for example, a polyfluoroalkyl such as a substantially perfluorinated alkyl.

"Heteroaryl," means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain aspects, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. In certain aspects of the disclosure, the heteroaryl group is furyl, imidazolyl, pyridinyl, pyrimidinyl, pyrazinyl, pyrazolyl, pyrrolyl, thiazolyl, thienyl, triazolyl, benzimidazolyl, benzofuranyl, indazolyl, indolyl, or quinolinyl.

The term "heterocyclyl" is used herein to refer both to a monocyclic heterocycle and a bicyclic heterocycle. The term "monocyclic heterocycle" is used herein to refer to a 3, 4, 5, 6 or 7 membered ring containing at least one heteroatom independently selected from the group consisting of O, N, and S where the ring is saturated or unsaturated, but not aromatic. The 3 or 4 membered ring can contain 1 heteroatom selected from the group consisting of O, N and S. The 5 membered ring can contain zero or one double bond. The 5 membered ring can also contain one, two or three heteroatoms selected from the group consisting of O, N and S. The 6 or 7 membered ring can contain zero, one or two double bonds; and can contain one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl,1,1-dioxidothiomorpholinyl (thiomorpholine sulfone), thiopyranyl, and trithianyl. The term "bicyclic heterocycle" is used herein to refer to a monocyclic heterocycle fused to either a phenyl, a monocyclic cycloalkyl, a monocyclic cycloalkenyl, a monocyclic heteroaryl, or to another monocyclic heterocycle that may be the same or different. The bicyclic heterocycle is connected to the parent molecular moiety through any carbon atom or any nitrogen atom contained within the monocyclic heterocycle portion of the bicyclic ring system. Representative examples of bicyclic heterocycles include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain aspects, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. In certain aspects of the disclosure, the heterocyclyl is pyrrolidinyl, piperidinyl, piperazinyl, or morpholinyl.

"NHS ester" means a succinimidy ester, i.e. an ester of formula:

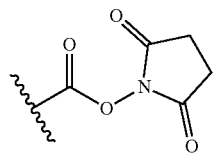 [SMILES: *C(=O)ON1C(=O)CCC1=O]

"Peptide," as used herein, refers generally to a single linear chain of amino acids. The terms "peptide" and "fragment" refer to a linear chain of amino acids. In certain aspects, the peptide comprises less than about 100 amino acids. In other aspects, the peptide comprises less than about 50 amino acids. The peptide may also comprise one or more chemical modifications known in the art and/or described herein. The peptide can be produced by naturally-occurring organisms and specifically non-recombinant cells, or by genetically-engineered or recombinant cells, and comprise molecules having the amino acid sequence of the native protein, or sequences that have deletions, additions, and/or substitutions of one or more amino acids of the native sequence.

"Phosphoramidite" means a group of formula —OP(NRR)₂OR where R is H or substituted or unsubstituted alkyl. An exemplary phosphoramidite group is —OP(N-iPr₂)₂OCH₂CH₂CN.

"Sulfonated NHS ester" as used herein, refers to a NHS ester as defined above substituted with a —SO₃⁻ group. A representative sulfonated NHS ester is a group of formula:

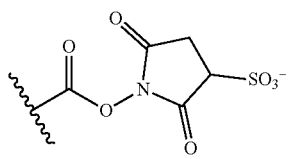

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

When substituted, heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various aspects, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some aspects, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some aspects, the substituent is selected from cyano, halogen, hydroxyl, and nitro.

Compounds and Luminescent Complexes Thereof

In some aspects, a class of lanthanide chelators are provided. In some aspects, the chelator is a compound according to Formula I or Formula II. In some aspects, the compound is based on cyclohexyl triethylenetetraamine hexaacetic acid (cyTTHA). In some aspects, functionalization of a central pendant carboxylic group with 7-aminoquinolinone (cs124) or 7-amino-4-trifluoromethyl-2-(1H)-quinolinone (cs124-CF3) sensitizer chromophores yielded Tb(III) and Eu(III) complexes with exceptional quantum yields in water (up to 54%), high absorptivity (>15,000 M-1 cm-1 at 365 nm), fast metal complexation rates and kinetic stability comparable to "industry standard" cryptates and macrocycles. Moreover, the modular synthesis of cyTTHA described below provides a robust scaffold for preparing multifunctional metal complexes via selective N-alkylation of the chelator backbone.

In some aspects, a compound is provided having a formula according to Formula I or Formula II below.

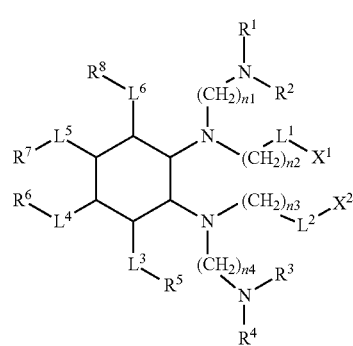

I

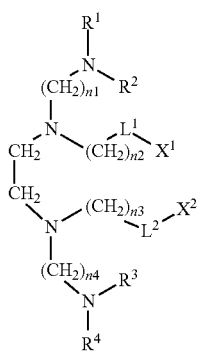

II

In the above, n1, n2, n3, and n4 are integers that can be chosen independently. In some aspects, n1 and n4 are independently selected from integers of from 1 to 5 or from 1 to 3. In some aspects, n1 and n4 are independently 1, 2, or 3. In some aspects, n2 and n3 are independently selected from integers of from 0 to 5 or from 0 to 3. In some aspects, n2 and n3 are independently 0, 1, 2, or 3.

In various aspects, $R^1$, $R^2$, $R^3$ and $R^4$ are independently selected from H, —$CH_2COOH$, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl, and substituted and unsubstituted heteroaryl. In some aspects, $R^1$, $R^2$, $R^3$ and $R^4$ are selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl and substituted and unsubstituted heteroaryl. In some aspects, $R^1$, $R^2$, $R^3$ and $R^4$ can have about 1 to 20, about 3 to 20, about 3 to 15, about 3 to 12, or about 6 to 12 carbon atoms. In some aspects, $R^2$, $R^3$, and $R^4$ are each —$CH_2COOH$; while $R^1$ is selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl and substituted and unsubstituted heteroaryl.

In some aspects, $R^5$, $R^6$, $R^7$ and $R^8$, are independently selected from H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2OR^9$, —$OC(O)R^9$, —$C(O)NR^9R^{10}$—$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, or $R^5$, together with the atom to which it is attached and one or more of $R^6$, $R^7$, $R^8$ forms a substituted and unsubstituted cycloalkyl, substituted and unsubstituted heterocyclyl, substituted and unsubstituted aryl, and substituted and unsubstituted heteroaryl. In some aspects, $R^5$, $R^7$ and $R^8$ are H, while $R^6$ is selected from the group consisting of H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2OR^9$, —$OC(O)R^9$, —$C(O)NR^9R^{10}$—$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol.

In some aspects, $R^5$, $R^6$, $R^7$, and $R^8$ are independently selected from halogen, —$CONH_2$, —CHO, —$C(O)NHNH_2$, —COOH, maleimidyl, thiazolidyl, haloacetyl, pyridyl disulfide, substituted and unsubstituted NHS ester, sulfonated NHS ester, succinimidyl, —NCO, —NCS, —$N_3$, substituted and unsubstituted alkynyl, tetrazolyl, substituted and unsubstituted cycoloctynyl, an amino acid moiety, and a phosphoramidite moiety. In some aspects, $R^5$, $R^6$, $R^7$, and $R^8$ are independently selected from tyramine, a tyramine derivative, biotin, estrogen, trimethoprim, methotrexate, benzyl guanine, and benzyl cytosine. In some aspects, $R^5$, $R^6$, $R^7$, and $R^8$ are independently selected from 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol.

In some aspects, $R^9$ and $R^{10}$ are independently selected from H, substituted and unsubstituted alkyl, substituted and unsubstituted aryl, substituted and unsubstituted heteroaryl and substituted and unsubstituted heterocyclyl, or $R^9$ and $R^{10}$, together with the atoms to which they are attached, form a 5- to 7 membered substituted or unsubstituted heterocyclyl or heteroaryl.

In some aspects, $L^1$, $L^2$, $L^3$, $L^4$, $L^5$, and $L^6$, are independently none (i.e. absent) or selected from substituted and unsubstituted alkyl.

In some aspects, $X^1$ and $X^2$ are independently selected from H, halogen, —CHO, —COOH, —$PO(OH)_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, substituted and unsubstituted alkyl, substituted and unsubstituted alkynyl, substituted and unsubstituted heteroalkyl, substituted and unsubstituted cycloalkyl, substituted and unsubstituted heterocyclyl, substituted and unsubstituted aryl, substituted and unsubstituted heteroaryl, fluorophores or chromophores that absorb light of a wavelength in the range of about 300 to about 420 nm, and a group of formula III:

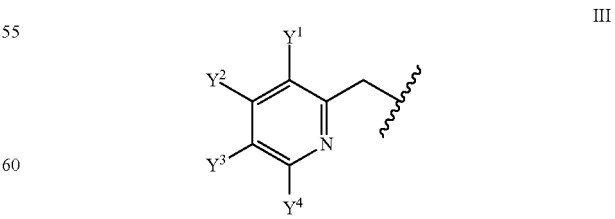

wherein $Y^1$, $Y^2$, $Y^3$, $Y^4$ are independently selected from H, substituted and unsubstituted alkyl, halogen, CN, $CF_3$, acyl, —$SO_2NR^{11}R^{12}$, —$NR^{11}R^{12}$, —$OR^{11}$, —$SO_2R^{11}$, —$COOR^{11}$, —$SO_2OR^{11}$, —$OC(O)NR^{11}$, —C(O)

NR$^{11}$R$^{12}$—NR$^{11}$C(O)R$^{12}$, —NR$^{11}$SO$_2$R$^{12}$, and —NO$_2$, or Y$^1$ together with the atom to which it is attached and one or more of Y$^2$, Y$^3$, Y$^4$ and forms a substituted and unsubstituted cycloalkyl, substituted and unsubstituted heterocyclyl, substituted and unsubstituted aryl or substituted and unsubstituted heteroaryl. In some aspects, X$^1$ and X$^2$ are each independently selected from the group consisting of —COOH, —PO(OH)$_2$, and a sensitizer so long as at least one of X$^1$ and X$^2$ is a sensitizer. In some aspects, at least one of X$^1$ and X$^2$ is —COOH. In other aspects, both X$^1$ and X$^2$ are a sensitizer.

In some aspects, X$^1$ and X$^2$ are independently selected from halogen, —CONH$_2$, —CHO, —C(O)NHNH$_2$, —COOH, maleimidyl, thiazolidyl, haloacetyl, pyridyl disulfide, substituted and unsubstituted NHS ester, sulfonated NHS ester, succinimidyl, —NCO, —NCS, —N$_3$, substituted and unsubstituted alkynyl, tetrazolyl, substituted and unsubstituted cycoloctynyl, an amino acid moiety, and a phosphoramidite moiety. In some aspects, one or both of X$^1$ and X$^2$ are independently selected from tyramine, a tyramine derivative, biotin, estrogen, trimethoprim, methotrexate, benzyl guanine, and benzyl cytosine. In some aspects, one or both of X$^1$ and X$^2$ are independently selected from 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol.

In Formula III above, R$^{11}$ and R$^{12}$ are independently selected from H, substituted and unsubstituted alkyl, substituted and unsubstituted aryl, substituted and unsubstituted heteroaryl and substituted and unsubstituted heterocyclyl, or R$^{11}$ and R$^{12}$, together with the atoms to which they are attached, are optionally joined to form a 5- to 7 membered heterocyclyl or heteroaryl;

Suitable sensitizers can include, for example,

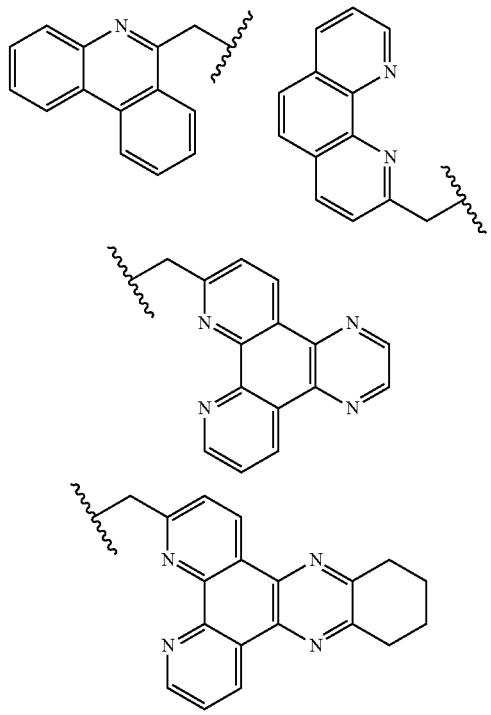

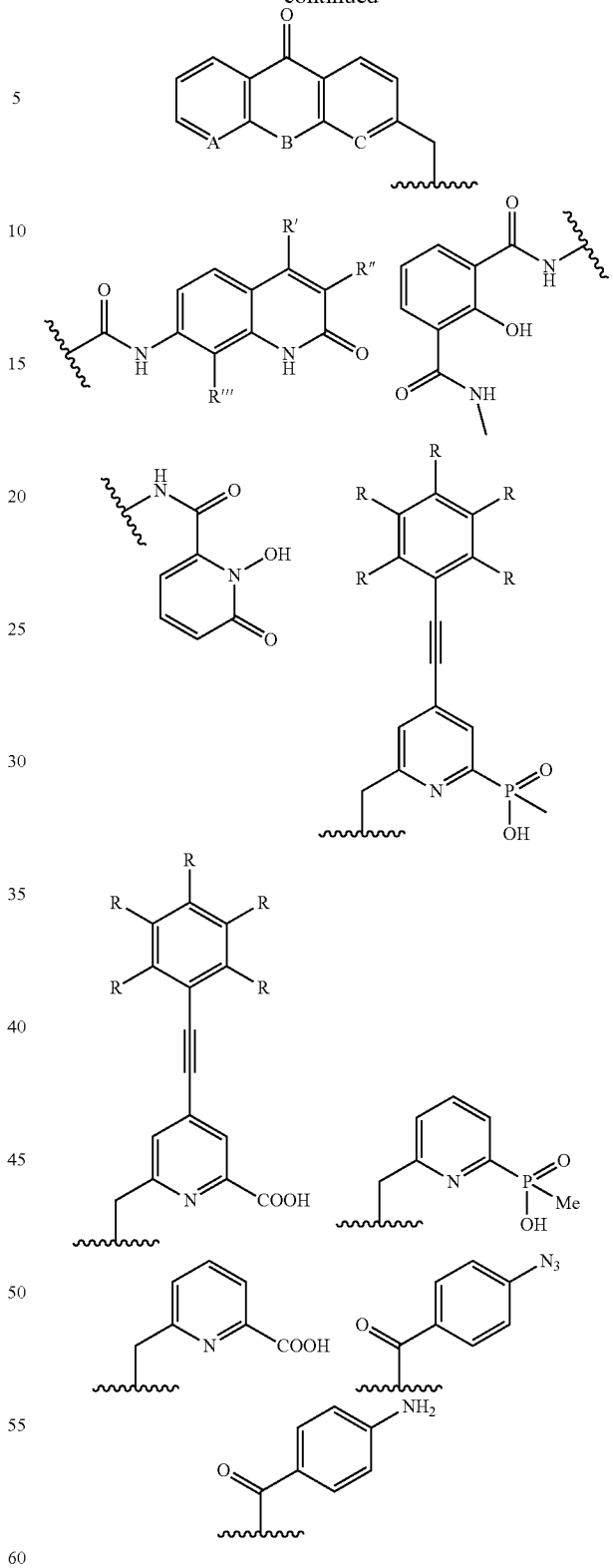

where A and C are independently selected from N and CH; R is independently selected at each occurrence from H and —OCH$_3$; R' is selected from —CH$_3$, —CF$_3$, and —CH$_2$COOH; R" is selected from H and —CH$_2$COOH; and R'" is selected from H and —CH$_3$. In some aspects, each occurrence of the sensitizer has a formula according to

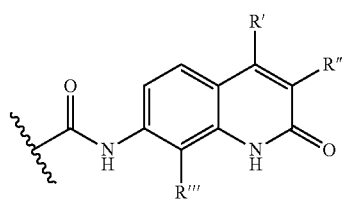

where R', R", and R'" are as defined above.

In some aspects, at least one of $R^1$, $R^2$, $R^3$, $R^4$, $X^1$ and $X^2$ are other than —$CH_2COOH$ or —$CH_2PO(OH)_2$. The compounds do not include the following compounds where R is $CH_3$ or $CF_3$.

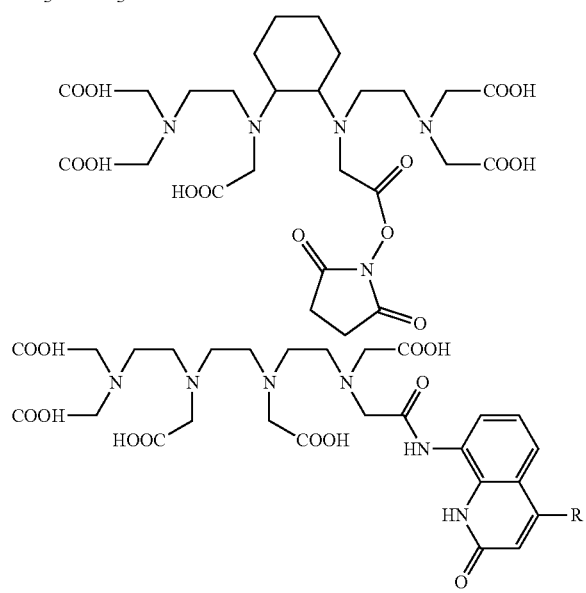

In some aspects, the compound is a compound according to Formula I wherein $R^1$ is —$CH_2COOH$; wherein $R^6$ is H. In some aspects, the compound is a compound according to Formula II where $R^1$ is —$CH_2COOH$. In some aspects, the compound is according to Formula I or Formula II where $L^3$, $L^4$, $L^5$, and $L^6$ are absent and $R^5$, $R^6$, $R^7$, and $R^8$ are H. In some aspects, the compound is according to Formula I or Formula II where $R^1$, $R^2$, $R^3$, and $R^4$ are —$CH_2COOH$. In some aspects, the compound is according to Formula I or Formula II wherein one of $X^1$ and $X^2$ is —COOH and the other is a fluorophore or chromophore that absorbs light of a wavelength in the range of about 300 to about 420 nm. For example, the fluorophore or chromophore can be any sensitizer described herein.

In some aspects, the compound is

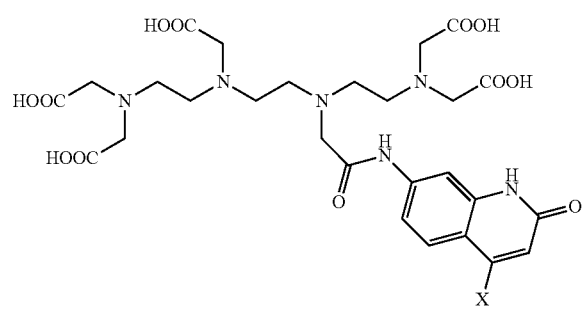

where X is $CH_3$ or $CF_3$.

In some aspects, the compound is

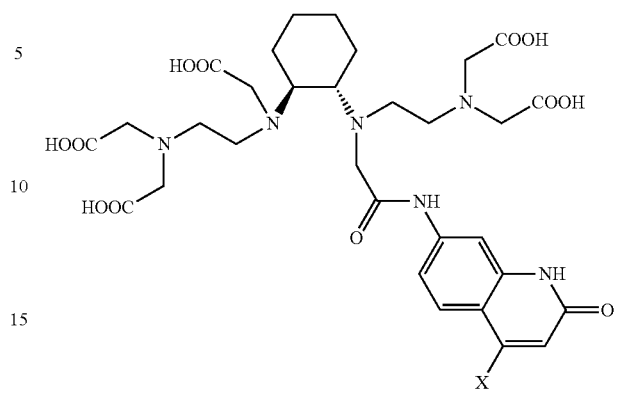

where X is $CH_3$ or $CF_3$.

In some aspects, the compound is

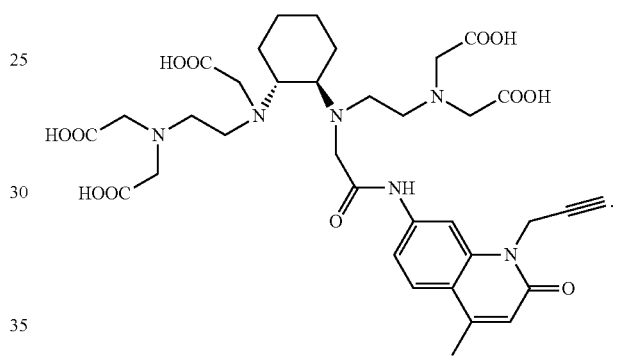

In some aspects, the compound is

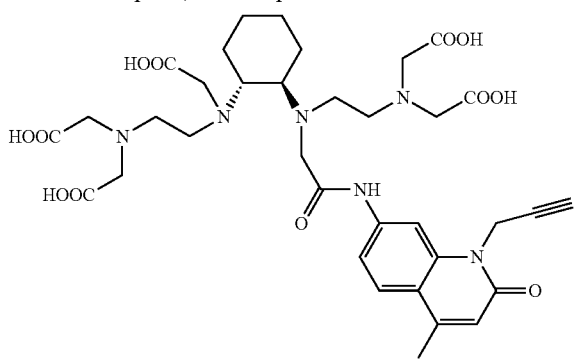

In some aspects, the compound is

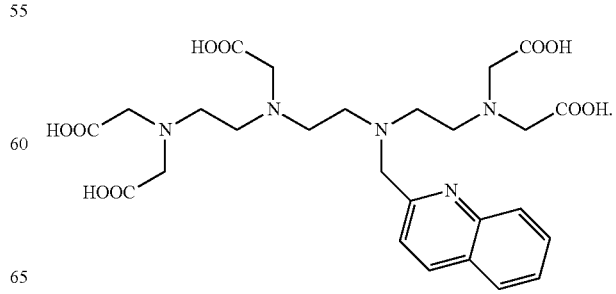

In some aspects, the compound is selected from the group consisting of
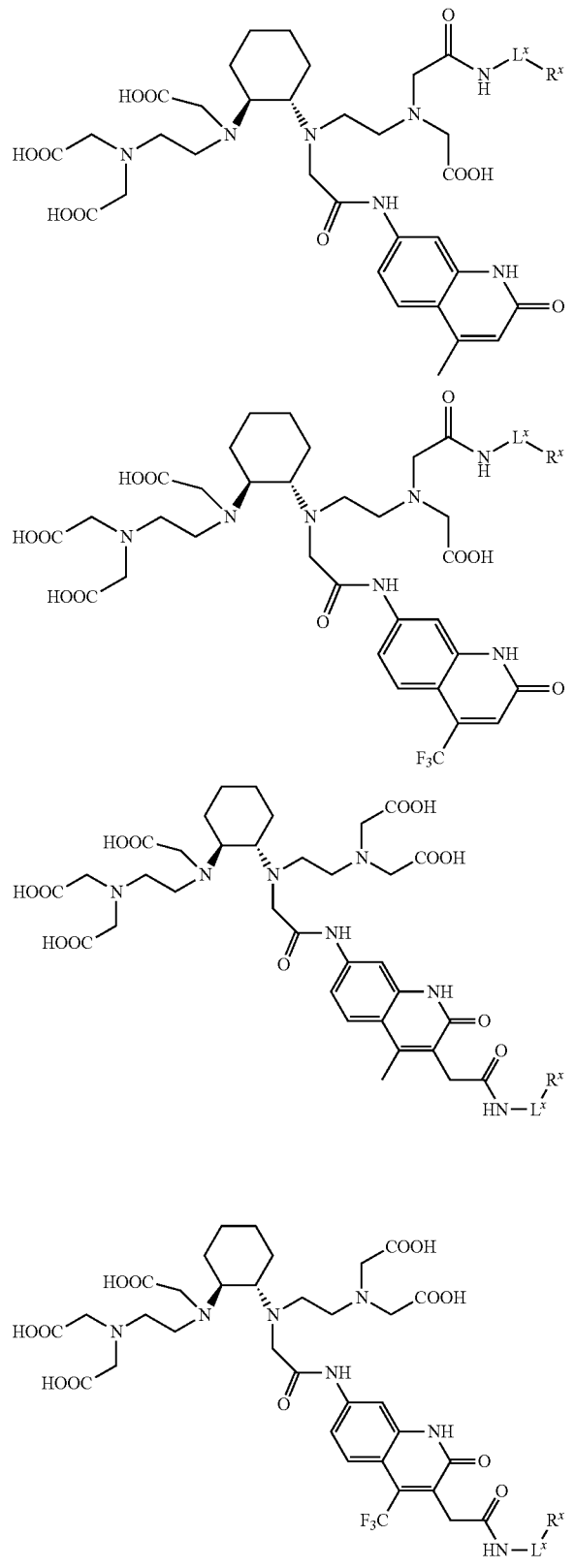
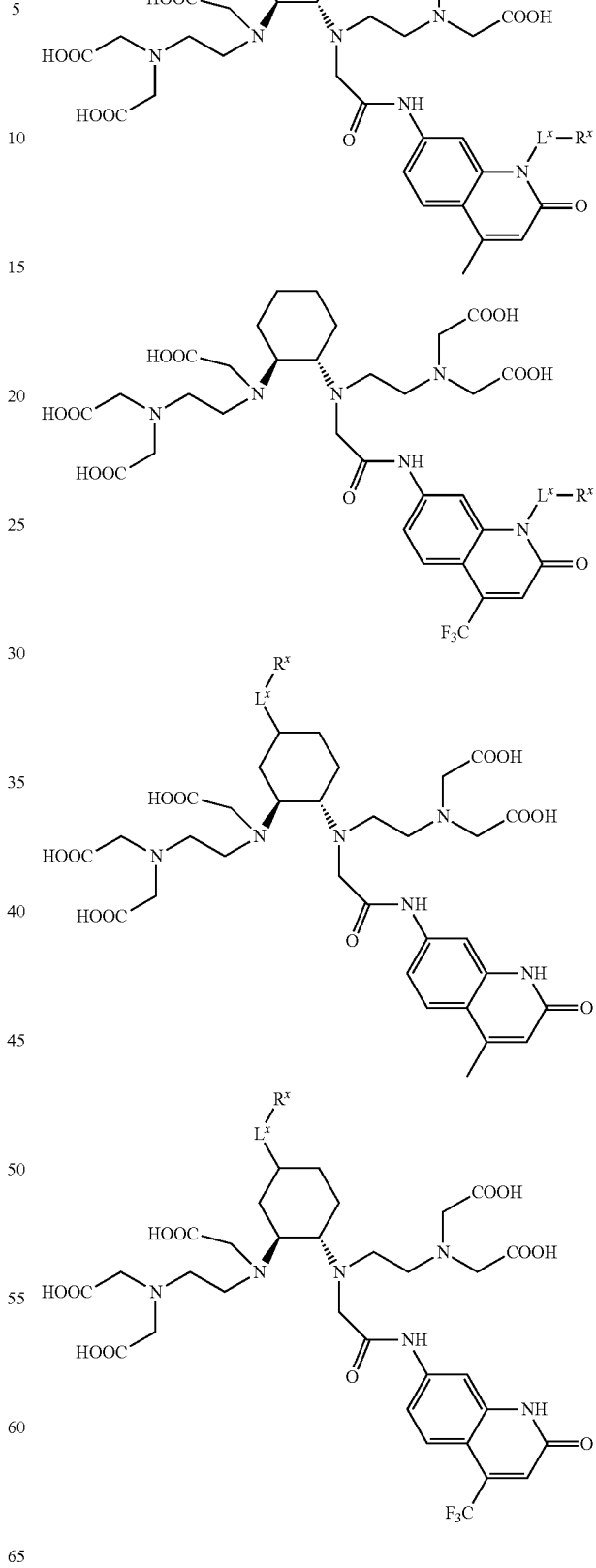

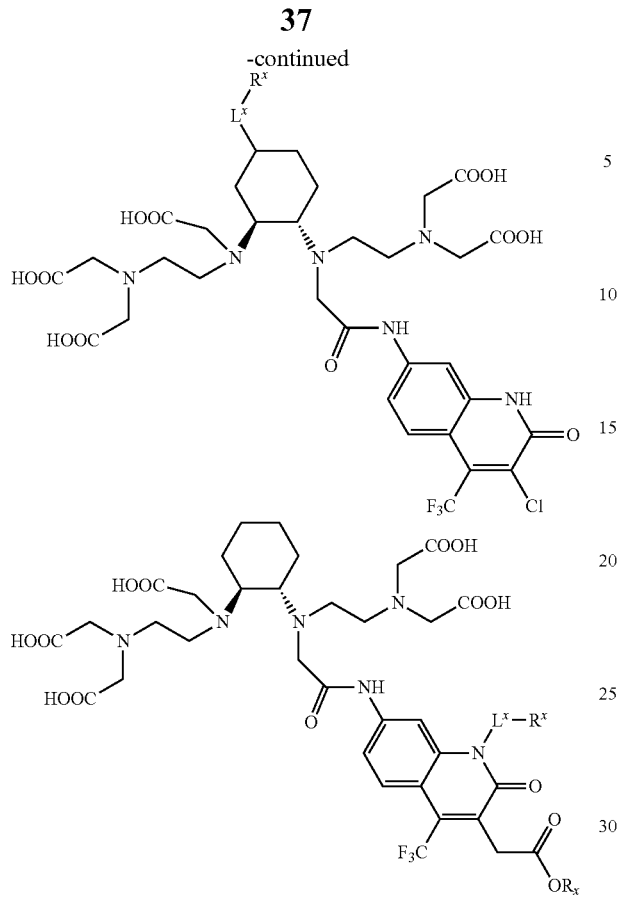

In the above formulas, $L^x$ is independently selected at each occurrence from none, substituted and unsubstituted alkyl, substitute and unsubstituted heteroalkyl, substituted and unsubstituted heteroaryl, and substituted and unsubstituted heterocycloalkyl. In some aspects, $L^x$ has about 3 to 30 carbon atoms, about 3 to 20 carbon atoms, about 6 to 20 carbon atoms, or about 6 to 12 carbon atoms.

In the above formulas, $R^x$ is independently selected at each occurrence from H, a halogen, substituted and unsubstituted alkyl, substituted and unsubstituted heteroalkyl, substituted and unsubstituted heteroaryl, and substituted and unsubstituted heterocycloalkyl. In some aspects, $R^x$ has about 3 to 30 carbon atoms, about 3 to 20 carbon atoms, about 6 to 20 carbon atoms, or about 6 to 12 carbon atoms.

In some aspects, Rx is independently selected at each occurrence from the following group —NCS
—NCO
—NHCOCH₂X
X: I, Br, Cl
—SSPh
—NH₂
—CHO
—CONHNH₂
—ONH₂

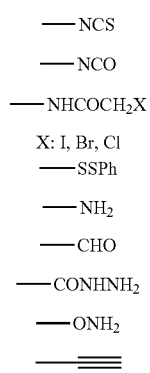

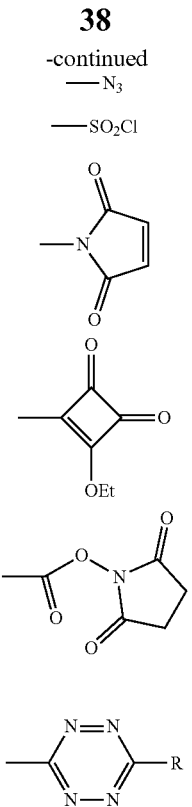

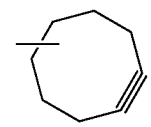

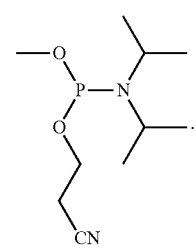

In some aspects, a structural feature of the compounds (chelators) is the presence of two diaminocycloalkyl moieties that are linked by a bridge of variable length (e.g., $(-CH_2-)_n$). The four cycloalkyl nitrogens serve as donor atoms, and pendant arms with variable numbers of donor atoms can be attached to the nitrogens. Thus, analogs of the chelators can be easily prepared that complex metal ions with different coordination numbers (e.g., compounds i, ii and v described below). Due to the inherent variability of the backbone of the metal chelators, it may be possible to stably bind metal ions of various diameters by varying the pendant coordinating structures (compounds iii, iv, vi, viii described below). Functional groups for conjugation can be attached to one of the cycloalkyl rings, or to the ring-bridging moiety (compound vii described below).

Accordingly, in some aspects the compounds is a compound of formula i, ii, iii, iv, v, vi, vii, or viii.

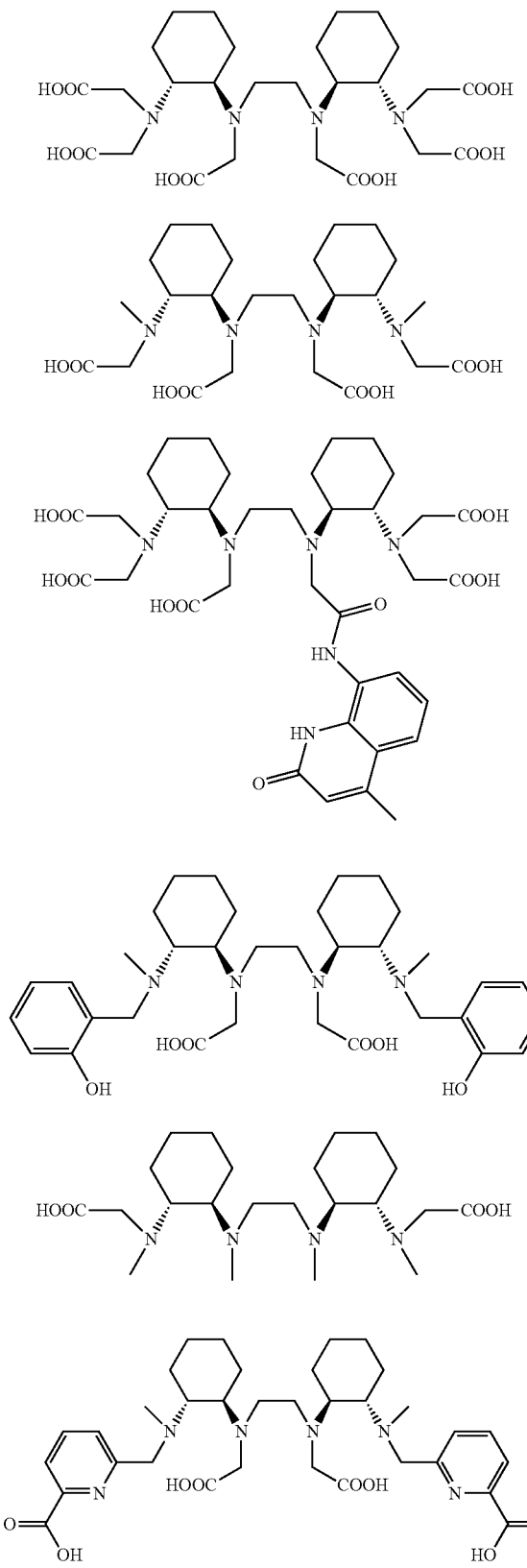

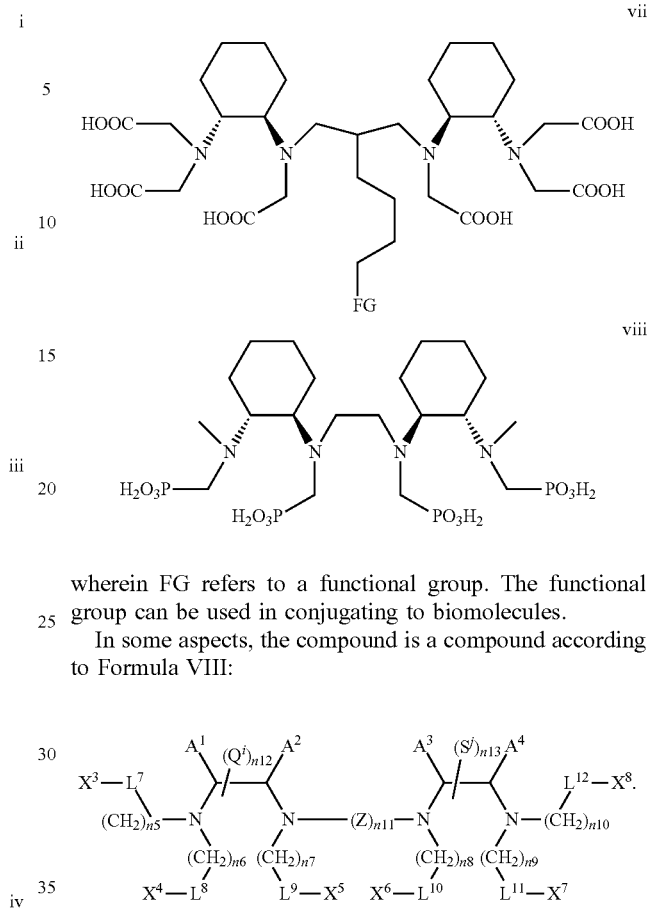

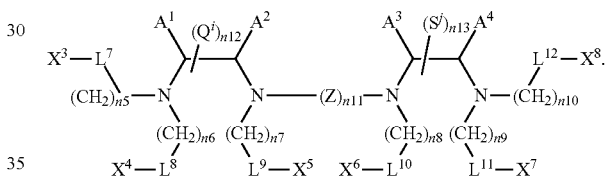

wherein FG refers to a functional group. The functional group can be used in conjugating to biomolecules.

In some aspects, the compound is a compound according to Formula VIII:

$$X^3-L^7\underset{(CH_2)_{n5}}{\overset{A^1\ (Q^i)_{n12}\ A^2}{\diagup}}N-\underset{(CH_2)_{n6}\ (CH_2)_{n7}}{\overset{}{N}}-(Z)_{n11}-\underset{(CH_2)_{n8}\ (CH_2)_{n9}}{\overset{}{N}}-\underset{X^6-L^{10}\ L^{11}-X^7}{\overset{A^3\ (S^j)_{n13}\ A^4}{\diagup}}N-(CH_2)_{n10}L^{12}-X^8.$$

In the above formula, $A^1$ and $A^2$ form together with the atoms to which they are attached a $C_3$-$C_8$-cycloalkyl group. In the above formula, $A^3$ and $A^4$ form together with the atoms to which they are attached a $C_3$-$C_8$-cycloalkyl group. In the above, Z is selected from the group consisting of of —$CH_2$—, —$CH_2CH_2$—, —$CH_2CH_2OCH_2CH_2$—, and —$CH_2CH_2SCH_2CH_2$—.

In the above formula, n5, n6, n7, n8, n9 and n10 are integers. In some aspects, n5, n6, n7, n8, n9 and n10 are independently selected from integers from 0 to 5 or from 0 to 3 inclusive. In some aspects, n11 is selected from integers from 1 to 10, from 1 to 5, or from 5 to 10 inclusive. In some aspects, n12 and n13 are independently selected from integers of from 1 to 16, from 1 to 5, from 6 to 10, or from 11 to 16 inclusive. In some aspects, i is an integer selected from integers of from 1 to n12 inclusive; and j is selected from integers of from 1 to n13 inclusive.

In the above formula, $nQ^i$ and $S^i$ are independently R, $R^i$ or where R, $R^i$ and $R^j$ are independently selected from substituted and unsubstituted alkyl, halogen, CN, $CF_3$, acyl, —$SO_2NR'R''$, —NR'R'', —OR', —$SO_2R'$, —COOR', —$SO_2OR'$, —OC(O)R', —C(O)NR'R'—NR'C(O)R'', —NR'$SO_2R''$, —$NO_2$, —C(O)$NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol or $R^i$, together with the atom to which it is attached and one or more additional R', forms a substituted and unsubstituted cycloalkyl, substituted and unsubstituted heterocyclyl, substituted and unsubstituted aryl or substituted and unsubstituted heteroaryl, or R', together with the atom to which it is attached and one or more additional R' forms a substituted and unsubstituted cycloalkyl, substituted and unsubstituted heterocyclyl, substituted and unsubstituted aryl, and substituted and unsubstituted heteroaryl. In the above, R' and R" are independently selected from H, substituted and unsubstituted alkyl, substituted and unsubstituted aryl, substituted and unsubstituted heteroaryl, and substituted and unsubstituted heterocyclyl;

In the above, $L^7$, $L^8$, $L^9$, $L^{10}$, $L^{11}$, and $L^{12}$ are independently absent, H or selected from substituted and unsubstituted heteroalkyl, and substituted and unsubstituted alkyl. In the above, $X^3$, $X^4$, $X^5$, $X^6$, $X^7$ and $X^8$ are independently selected from H, halogen, —CHO, —COOH, —PO(OH)$_2$, —CONH$_2$, —C(O)NHNH$_2$, —NCO, —NCS, —N$_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, 5-cholesten-3β-ol, substituted and unsubstituted alkyl, substituted and unsubstituted alkynyl, substituted and unsubstituted cycloalkyl, substituted and unsubstituted heterocyclyl, substituted and unsubstituted aryl, substituted and unsubstituted heteroaryl, fluorophores or chromophores that absorb light of a wavelength in the range of about 300 to about 420 nm, and compounds according to formula IX:

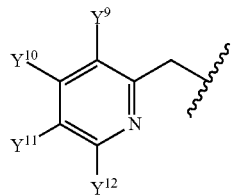

IX

In compound IX, $Y^9$, $Y^{10}$, $Y^{11}$, $Y^{12}$ are independently selected from H, substituted and unsubstituted alkyl, halogen, CN, CF$_3$, acyl, —SO$_2$NR$^{13'}$R$^{13''}$, —NR$^{13'}$R$^{13''}$, —OR$^{13'}$, —SO$_2$R$^{13'}$, —COOR$^{13'}$, —SO$_2$OR$^{13'}$, —OC(O)R$^{13'}$, —C(O)NR$^{13'}$R$^{13''}$, —NR$^{13'}$C(O)R$^{13''}$, —NR$^{13'}$SO$_2$R$^{13''}$, and —NO$_2$, or $Y^9$ together with the atom to which it is attached and one or more of $Y^{10}$, $Y^{11}$, $Y^{12}$ and forms a substituted and unsubstituted cycloalkyl, substituted and unsubstituted heterocyclyl, substituted and unsubstituted aryl or substituted, and unsubstituted heteroaryl, where R$^{13'}$ and R$^{13''}$ are independently selected from H, substituted and unsubstituted alkyl, substituted and unsubstituted aryl, substituted and unsubstituted heteroaryl and substituted, and unsubstituted heterocyclyl.

In some aspects, the compound is a compound according to Formula IX where at least one of $X^3$, $X^4$, $X^5$, $X^6$, $X^7$ and $X^8$ is the fluorophore or chromophore that absorbs light of a wavelength in the range of about 300 to about 420 nm, and the fluorophore or chromophore is selected from the group consisting of

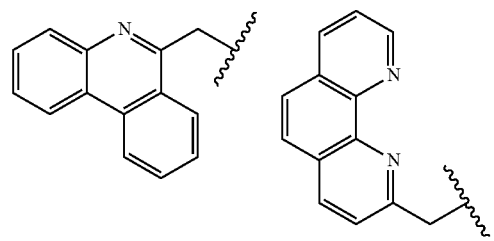

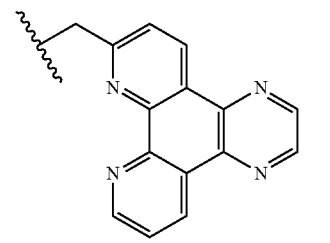

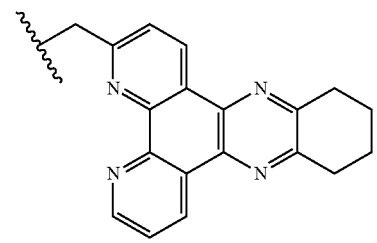

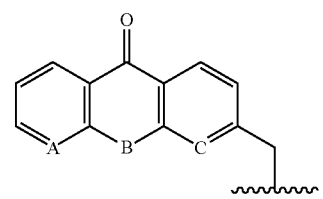

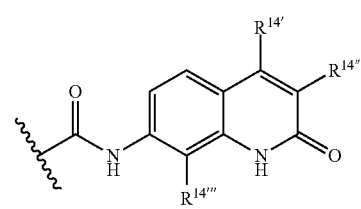

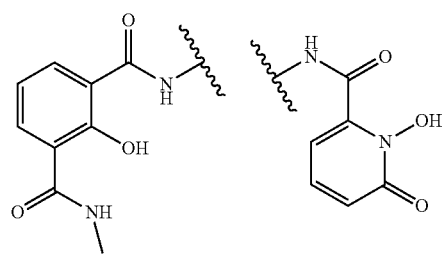

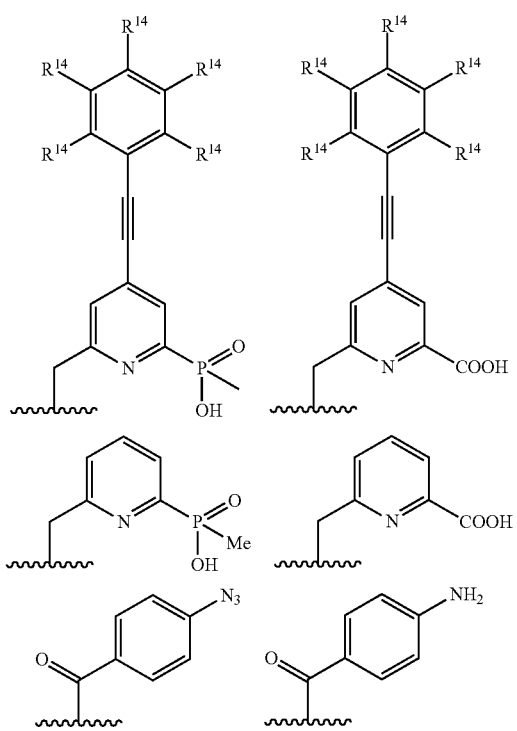

wherein A and C are independently selected from N and CH; wherein $R^{14}$ is independently selected at each occurrence from H and —OCH$_3$; wherein $R^{14'}$ is selected from —CH$_3$, —CF$_3$, and —CH$_2$COOH; wherein $R^{14''}$ is selected from H and —CH$_2$COOH; and wherein $R^{14'''}$ is selected from H and —CH$_3$.

In some aspects, the compound is a compound according to Formula IX where the fluorophore or chromophore is a compound of formula:

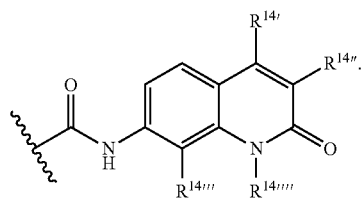

wherein $R^{14'}$, $R^{14''}$, and $R^{14'''}$ are as in Claim 7; and wherein $R^{14''''}$ is selected from H and —CH$_3$.

In some aspects, the compound is a compound according to Formula IX where the compound is selected from the group consisting of

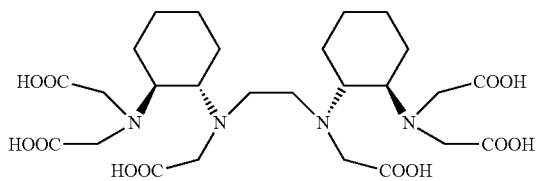

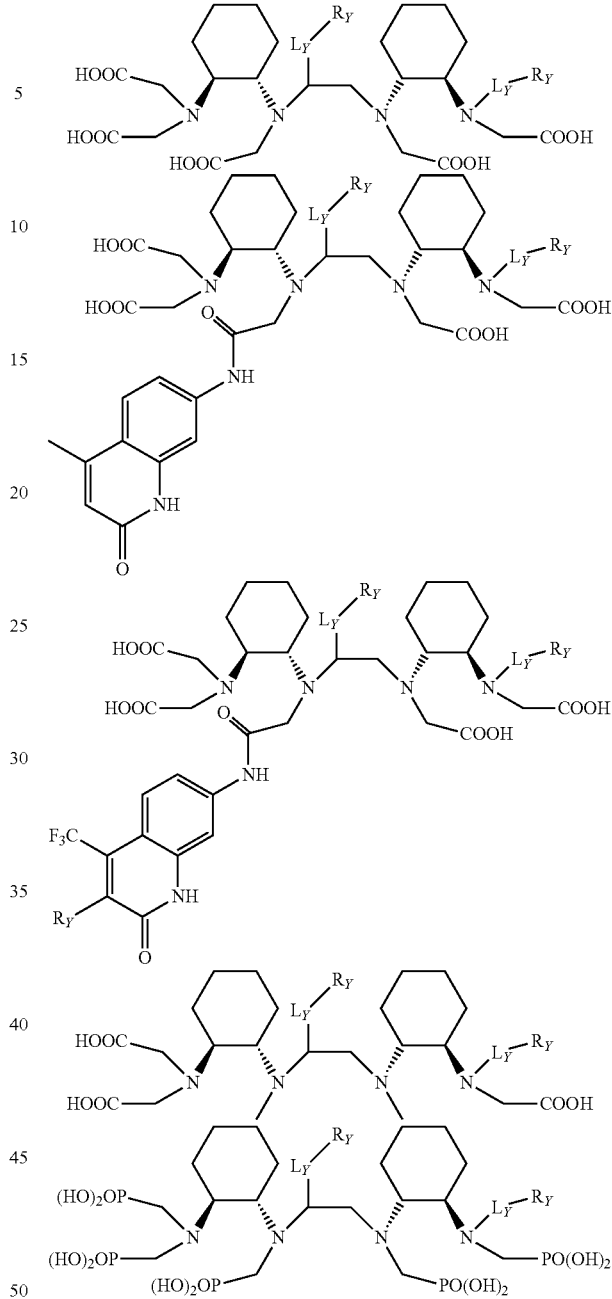

where $L_Y$ is independently at each occurrence selected from the group consisting of none, substituted and unsubstited alkyl, substituted and unsubstited heteroalkyl, substituted and unsubstited heteroaryl, and substituted and unsubstited heterocycloalkyl; and where $R_Y$ is independently at each occurrence selected from the group consisting of hydrogen, a halogen, substituted and unsubstited alkyl, substituted and unsubstited heteroalkyl, substituted and unsubstited heteroaryl, and substituted and unsubstited heterocycloalkyl.

In some aspects, $R_Y$ is selected from the group consisting of

—NCS

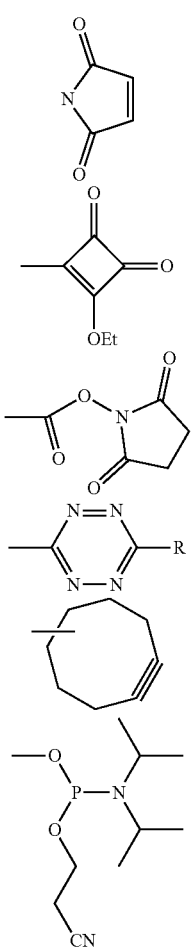

Luminescent complexes are also provided. High brightness at relatively long excitation wavelengths is useful to minimize inner filter effects in bioassays, and it is critical for time-gated, luminescence microscopy because conventional optics do not effectively transmit below 350 nm.[4-5] However, 1:1 ligand:metal complexes with brightness values exceeding 5000 $M^{-1}$ $cm^{-1}$ above 350 nm are rare.[6-7] Disclosed herein are protein-targeted Tb(III) labels that can be used for intracellular, time-gated imaging.[8-11] These efforts have leveraged the exceptionally bright (QY, 54%) and kinetically stable Lumi4 Tb(III) complex which is compatible with the 365 nm LED excitation source of our microscope ($\varepsilon_{365}$, ca. 8500 $M^{-1}$ $cm^{-1}$).[6]

The luminescent complexes provided herein include a complex formed between a compound described herein and a metal atom or ion. In some aspects, the metal ion is a lanthanide. In some aspects, the metal ion is Eu(III) or Tb(III). The metal ion can include any stable or any radioactive isotope of a metal selected from the group consisting of Ga, In, Tl, La, Ce, Pr, Nd, Pm, Sm, Eu, Gd, Tb, Dy, Ho, Er, Tm, Yb, Lu, Sc, Y, Ti, Zr, Cr, Mn, Tc, Re, Fe, Ru, Co, Rh, Ir, Ni, Pd, Pt, Cu, Zn, Cd, Hg, Al, Ge, Sn, Pb, Sb, Bi, Te, Po, Mg, Ca, Sr, Ba, Ra, Ac, Th and U. The metal ion can include a metal ion selected from the group consisting of $^{66}$Ga, $^{67}$Ga, $^{68}$, $^{111}$In, $^{201}$Tl, $^{142}$Pr, $^{149}$Pm, $^{153}$Sm, $^{153}$Gd, $^{159}$Gd, $^{166}$Ho, $^{175}$Yb, $^{177}$Lu, $^{47}$Sc, $^{90}$Y, $^{89}$Zr, $^{51}$Cr, $^{99m}$Tc, $^{188}$Re, $^{186}$Re, $^{57}$Co, $^{101m}$Rh, $^{62}$Cu, $^{64}$Cu, $^{67}$Cu, $^{117m}$Sn, $^{203}$Pb, $^{212}$Pb, $^{212}$Bi, $^{213}$Bi, $^{223}$Ra, and $^{225}$Ac.

Many of the compounds described herein will be recognized as exhibiting stereoisomerism, enantiomerism and/or diastereomerism, as the case may be. Unless a specific stereoisomer is indicated, the disclosure will be understood to refer to all possible stereoisomers, so whenever a structure is shown in the stereochemical ambiguous form such as the structure of Formula I, it will be understood that the disclosure includes all possible stereoisomers as if each stereoisomer were individually and explicitly disclosed. Compositions containing the compounds described herein, where applicable, may contain a racemic mixture or any other mixture of the stereoisomers. For example, in some aspects compositions contain a single stereoisomer or contain a non-racemic mixture of two or more stereoisomers where at least one stereoisomer has a greater relative concentration than would otherwise be present in a racemic mixture of the stereoisomers. As a specific non-limiting example, compounds according to Formula I can exist in any one of the following stereoisomers. Each of the following stereoisomers should be considered a part of the disclosure, as well as mixtures of two or more of the stereoisomers. Such mixtures can be racemic or otherwise.

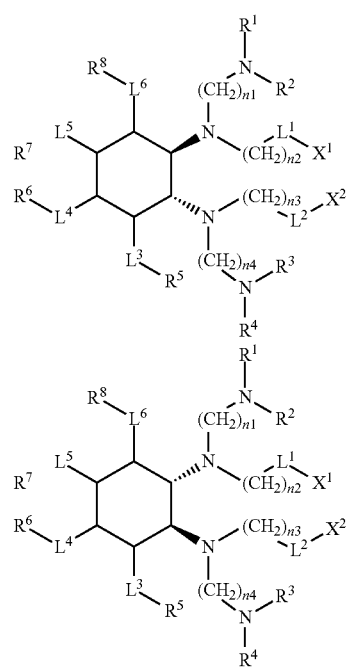

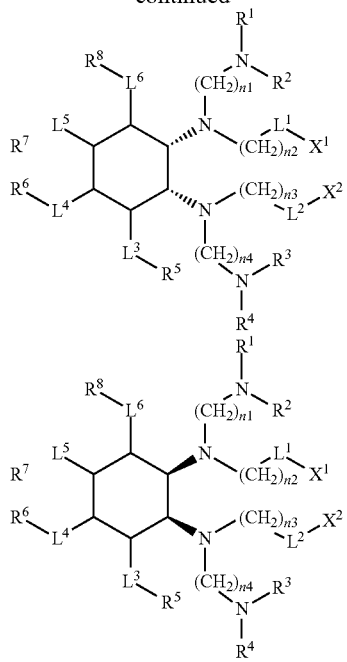

Methods of Making Compounds and Luminescent Complexes Thereof

Various methods of making the compounds herein are also provided. In some aspects, the methods include a modular synthesis that follows a general reaction scheme of N-benzyl protection, N-alkylation with an alkyl halide, benzyl deprotection via hydrogenation, a second alkyl halide N-alkylation, and finally a sensitizer installation via a third alkylation. The methods can allow for the synthesis of a variety of compounds described herein with overall yields in excess of 25% and without the need for HPLC purification. Since sensitizer inclusions occurs at or near the last step, the methods can be applied to insert a variety of sensitizers, fluorophores, and chromophores.

In various aspects, methods of making the compounds are provided that include (i) alkylating a compound according to Formula I-C or Formula II-C with a compound according to Formula IV to produce a first intermediate; (ii) alkylating the first intermediate with a compound according to Formula V to produce a second intermediate; and (iii) deprotecting the second intermediate to produce the compound according to Formula I or Formula II. In some aspects, the first alkylating step, the second alkylating step, or both alkylating steps are performed at about room temperature, e.g. about 65° C. to 75° C.

The compound according to Formula I-C and Formula II-C are

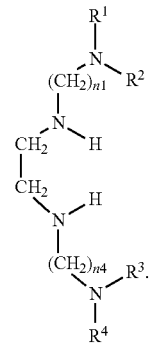

The compounds according to Formula IV and Formula V are

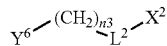

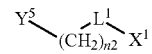

In some aspects, the method further includes (a) alkylating a compound according to Formula I-B or Formula II-B with one or both of a compound according to Formula VI and a compound according to Formula VII followed by benzyl deprotection via hydrogenation to produce the compound according to Formula I-C or Formula II-C. The step of alkylating the compound according to Formula I-B or Formula II-B can be performed at a temperature of about 60° C., e.g. about 55° C. to 65° C.

The compounds according to Formula I-B and Formula II-B are:

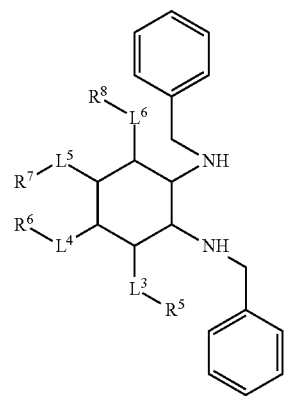

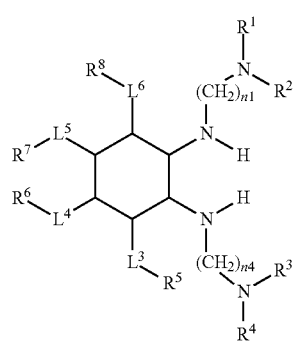

-continued

II-B

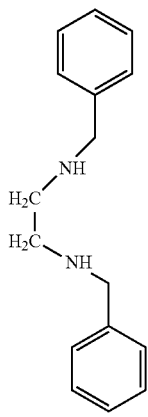

The compounds according to Formula VI and VII are

VI

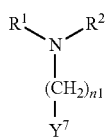

VII

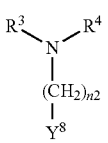

In the above formulas, $Y^7$ and $Y^8$ are each independently a halogen, preferably Br. In the above formulas, $Y^5$ and $Y^6$ are each independently a halogen such as Cl or Br, preferably Cl. In the above formula, n1, n2, n3, and n4 are as defined above; and $L^1$, $L^2$, $L^3$, $L^4$, $L^5$ and $L^6$, are as defined above.

In the above formulas, $R^1$, $R^2$, $R^3$ and $R^4$ are as defined above, except that the $R^1$, $R^2$, $R^3$ and $R^4$ can be protected with one or more protecting groups to protect from unwanted alkylation during the alkylation steps. Such protection chemistry is generally known to those skilled in the art. For example, in some aspects the $R^1$, $R^2$, $R^3$ or $R^4$ include a carboxylic acid that is protected with a suitable carboxylic acid protecting group, e.g. a methyl ester, a benzyl ester, or a tert-butyl ester. In some aspects, one or more (sometime all) of $R^1$, $R^2$, $R^3$, and $R^4$ are each —CH$_2$COOtBu.

In the above formulas, $R^5$, $R^6$, $R^7$ and $R^9$ are as defined above, except that the $R^5$, $R^6$, $R^7$ and $R^9$ can be protected with one or more protecting groups to protect from unwanted alkylation during the alkylation steps. Such protection chemistry is generally known to those skilled in the art. For example, in some aspects the $R^5$, $R^6$, $R^7$ and $R^9$ include a carboxylic acid that is protected with a suitable carboxylic acid protecting group, e.g. a methyl ester, a benzyl ester, or a tert-butyl ester.

In the above formulas, $R^9$ and $R^{19}$ are as defined above, except that $R^9$ and $R^{19}$ can be protected with one or more protecting groups to protect from unwanted alkylation during the alkylation steps. Such protection chemistry is generally known to those skilled in the art. For example, in some aspects the $R^9$ and $R^{19}$ include a carboxylic acid that is protected with a suitable carboxylic acid protecting group, e.g. a methyl ester, a benzyl ester, or a tert-butyl ester.

In the above formulas, $X^1$ and $X^2$ are as defined above, except that $X^1$ and $X^2$ can be protected with one or more protecting groups to protect from unwanted alkylation during the alkylation steps. Such protection chemistry is generally known to those skilled in the art. For example, in some aspects the $X^1$ and $X^2$ include a carboxylic acid that is protected with a suitable carboxylic acid protecting group, e.g. a methyl ester, a benzyl ester, or a tert-butyl ester.

In the above aspects, one or more groups can be protected with a suitable protecting group to prevent unwanted alkylation or other reactions that may occur during alkylation. Such protecting groups are generally described elsewhere. In some aspects, a carboxylic acid is protected with a suitable carboxylic acid protecting group. Carboxylic acid protecting groups can include a variety of esters such as methyl esters, benzyl esters, esters of 2,6-disubstituted phenols (e.g. 2,6-dimethylphenol, 2,6-diisopropylphenol, 2,6-di-tert-butylphenol), and silyl esters. In some aspects, an alcohol can be protected with a suitable alcohol protecting group such as acetyl, methoxy methyl, or tetrahydrofuran. In some aspects, an amine is protected by a suitable amine protecting group such as tert-Butyloxycarbonyl, carbamate, and tosyl groups. In some aspects, the methods further include one or more protecting and deprotecting steps.

Methods of Using Compounds and Luminescent Complexes Thereof

The compounds provided herein can be used in a variety of manners, including but not limited to as therapeutics, e.g. as cancer therapeutics for carrying various radioisotopes, or for a variety of imaging applications.

In some aspects, a method is provided for detecting the presence of an analyte in a sample. The sample can be a living sample, for example the sample can be a human. The sample can include tissue such as muscles or organs. The method can include (a) contacting the sample with a composition comprising a luminescent complex described herein, (b) exciting the complex; and (c) detecting luminescence from the complex.

In some aspects, a method is provided for detecting the presence of an analyte in a sample, the method including: (a) contacting the sample and a composition comprising a luminescent complex according to any one of claims 12-14 and a luminescence modifying group; (b) exciting the complex; and (c) determining a luminescent property of the sample; wherein energy is transferred between the luminescent complex and the luminescence modifying group when the complex is excited; and wherein the presence of the analyte results in a change in the luminescent property. The complex and the luminescence modifying group can be part of the same molecule or they can be part of different molecules.

In some aspects, the analyte binds to an antibody, wherein the antibody is covalently linked to a member selected from a luminescence modifying group and a luminescent complex described herein.

In some aspects, the excitation of the complex is performed by irradiating the complex with light, in particular with near-UV light. The term "near-UV" as used herein means ultraviolet radiation having wavelengths in the range from about 315 nm to about 410 nm. In some aspects, the step of detecting lumenescence includes detecting luminescence in the visible spectrum. As used herein, the visible spectrum includes wavelengths in the range of about 400 nm to about 700 nm.

In some aspects, the methods include time-gated detecting to eliminate background fluoresence. In some aspects, the samples include blood cells, tissues, and living cells. The methods can be particularly well suited for high-throughput screening.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

A modular synthesis was designed that followed a general reaction scheme of N-benzyl protection, N-alkylation with an alkyl halide, benzyl deprotection via hydrogenation, a second alkyl halide N-alkylation, and finally a sensitizer installation via a third alkylation. See Schemes 2 and 3. As with previously reported attempts to heterogeneously alkylate TTHA, we observed that formation of piperazin-2-one byproducts substantially lowered reaction yields,[21-22] particularly when preparing the acyclic TTHA analogs. We minimized piperazin-2-one formation by first alkylating with two relatively bulky alkyl bromide groups and then running the subsequent alkylation reaction at room temperature.[13, 14] Following this route, we prepared sensitized cyTTHA analogs 1a-b and 3a-d in 6 steps with good overall yields (25% for 3a) and without the need for HPLC purification. Since sensitizer inclusion occurred in the last step, we further tested the generality of our strategy by substitution of a quinoline chromophore instead of carbostyril in the central carboxylic arm to yield compound 2.

Synthetic Methods

The syntheses of representative compounds is shown in Schemes 1-4 and synthetic procedures below.

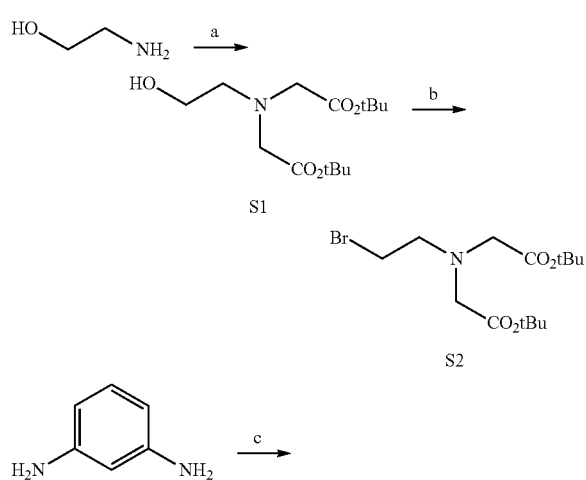

Scheme 1

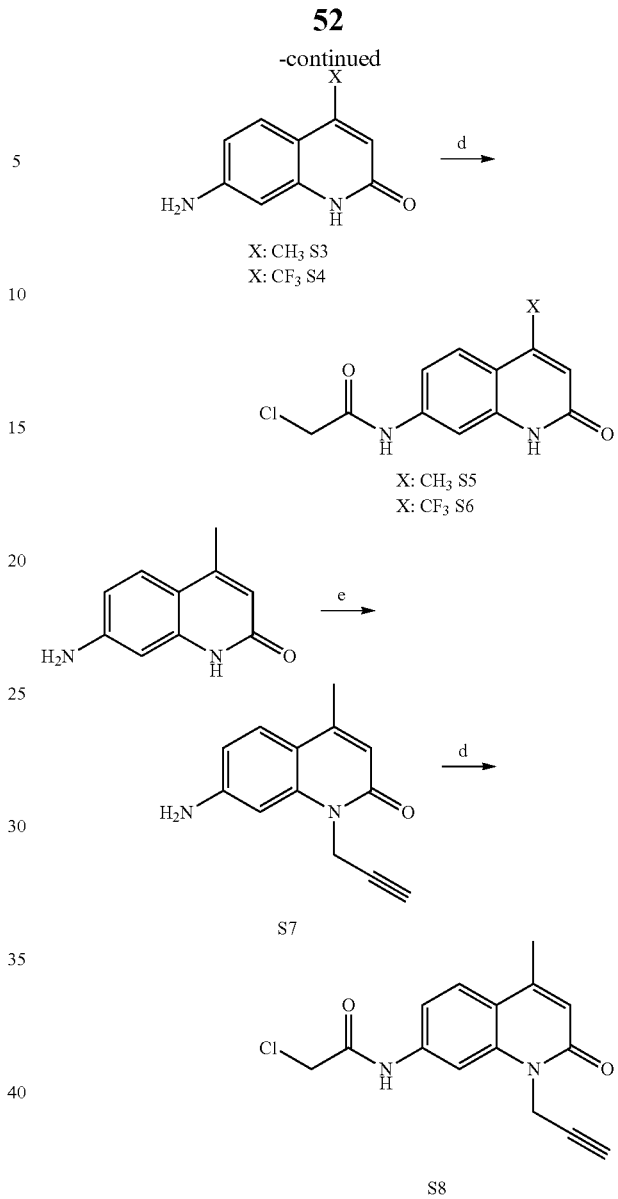

tert-butyl 2,2'-(2-hydroxyethylazanediyl)diacetate (S1)

In a round bottom flask, sodium carbonate (5.32 g, 50.2 mmol) and dry DMF (50 mL) were mixed and 2-Ethanolamine (1.20 mL, 20.0 mmol) was added in one portion, and the flask was placed in an ice bath. To this suspension, tert-butylbromoacetate (6.64 mL, 45.0 mmol, 2.25 equiv) was added over 1 h. The contents were stirred for 24 h at RT. The reaction mixture was dissolved in a 1:1 mixture of EtOAc and water. The product was extracted with EtOAc and washed with brine (100 mL). The EtOAc layer was separated, dried over $MgSO_4$ and concentrated to obtain colorless viscous oil. The crude mixture purified via flash column chromatography over silica gel to obtain the product as colorless, viscous oil. Yield 99%. $^1H$ NMR (500 MHz, $CDCl_3$): δ ppm 3.47 (t, J=10.0 Hz, 2H), 3.36 (s, 4H), 2.95 (t, J=10.0 Hz, 2H), 1.34 (s, 9H). $^{13}C$ NMR (126 MHz, $CDCl_3$): δ ppm 170.76, 81.37, 56.92, 42.53, 28.44. ESIMS (m/z) 290 [M+H]$^+$, 312 [M+Na]$^+$, 288 [M−H]$^−$ tert-butyl 2,2'-(2-bromoethylazanediyl)diacetate (S2)

Starting with compound S1 (5.78 g, 20.0 mmol) and triphenylphosphine (7.86 g, 30.0 mmol, 1.5 equiv) were dissolved in dry DCM (100 mL) with in an ice bath. N-Bromosuccinimide (4.27 g, 24.0 mmol, 1.2 equiv) was added in small portions over 40 minutes. The contents were allowed to warm to the RT and stirred for 3 h under $N_2$ atmosphere. The solvent was removed on a rotavap to obtain brown-red viscous oil that was washed with diethyl ether and was filtered through a small silica column to obtain colorless viscous oil. The crude mixture was purified using flash chromatography over silica gel to obtain product as colorless, viscous oil. Yield 98%. $^1$H NMR (500 MHz, $CDCl_3$):δ ppm 3.48 (s, 4H), 3.43 (t, J=10.0 Hz, 2H), 3.12 (t, J=10.0 Hz, 2H), 1.46 (s, 9H). $^{13}$C NMR (126 MHz, $CDCl_3$): δ ppm 170.55, 81.32, 56.49, 30.33, 28.17. ESIMS (m/z) 352 $[M+H]^+$, 374 $[M+Na]^+$, 350 $[M-H]^-$

7-amino-4-methylquinolin-2(1H)-one (S3)

1,3-Phenylenediamine (1.08 g, 10.0 mmol) and ethyl acetoacetate (1.26 mL, 10.0 mmol) were refluxed for 48 h. Crystallization using MeOH gave colorless needle crystals. Yield 75%. $^1$H NMR (500 MHz, DMSO-d6):δ ppm 11.14 (s, 1H), 7.31 (d, J=10.0 Hz, 1H), 6.44 (dd, J=10.0, 5.0 Hz, 1H), 6.35 (d, J=5.0 Hz, 1H), 5.93 (s, 1H), 5.72 (s, 2H), 2.26 (s, 3H). $^{13}$C NMR (126 MHz, DMSO-d6): δ ppm 162.84, 151.52, 148.37, 141.23, 126.01, 115.12, 110.87, 97.26, 18.91. ESIMS (m/z) 175 $[M+H]^+$, 197 $[M+Na]^+$, 173 $[M-H]^-$

7-amino-4-(trifluoromethyl)quinolin-2(1H)-one (S4)

1,3-phenylenediamine (1.08 g, 10.0 mmol) and ethyl 4,4,4-trifluoro-3-oxobutanoate (1.46 mL, 10.0 mmol, 1 equiv) were refluxed for 24 h in 20 mL DMF. The crude mixture was purified using flash chromatography over silica gel to obtain product as a yellow powder. Yield 95%. $^1$H NMR (500 MHz, DMSO-d6):δ ppm 11.83 (s, 1H), 7.35 (d, J=10.0 Hz, 1H), 6.57 (d, J=10.0 Hz, 1H), 6.47 (s, 1H), 6.44 (s, 1H), 6.16 (s, 2H). $^{13}$C NMR (126 MHz, DMSO-d6): δ ppm 161.34, 152.56, 142.62, 137.09-137.34, 125.58, 124.45, 113.93, 112.27, 103.96, 97.18. ESIMS (m/z) 229 $[M+H]^+$, 251 $[M+Na]^+$, 227 $[M-H]^-$

2-chloro-N-(4-methyl-2-oxo-1,2-dihydroquinolin-7-yl)acetamide (S5)

To compound S3 (348 mg, 2.0 mmol) in DMF (0.20 M) was added $NEt_3$ (418 uL, 6.0 mmol, 3.0 equiv) and the solution was cooled to 0° C. before chloroacetyl chloride (159 uL, 1.0 equiv) diluted in DMF was added drop wise to the reaction solution. After 6 h, the reaction mixture was diluted with EtOAc and washed with $H_2O$ and brine to give a grey precipitate in the organic layer. After filtration, the solid was dried under high vacuum to give compound S5 as a white solid (76%). $^1$H NMR (500 MHz, DMSO-d6): δ ppm 11.60 (s, 1H), 10.67 (s, 1H), 7.77 (s, 1H), 7.66 (d, J=10.0 Hz, 1H), 7.35 (d, J=10.0 Hz, 1H), 6.29 (s, 1H), 3.36 (s, 2H), 2.39 (s, 3H). $^{13}$C NMR (126 MHz, DMSO-d6): δ ppm 165.45, 162.42, 148.05, 140.62, 139.90, 125.92, 119.79, 116.40, 114.02, 105.24, 44.08, 18.86. ESIMS (m/z) 251 $[M+H]^+$, 273 $[M+Na]^+$, 249 $[M-H]^-$

2-chloro-N-(2-oxo-4-(trifluoromethyl)-1,2-dihydroquinolin-7-yl)acetamide (S6)

To compound S4 (456 mg, 2.0 mmol) in DMF (0.20 M) was added $NEt_3$ (418 uL, 6.0 mmol, 3.0 equiv) and the solution was cooled to 0° C. before chloroacetyl chloride (159 uL, 2.0 mmol, 1.0 equiv) diluted in DMF was added drop wise to the reaction solution. After 6 h, water 100 mL, 50 mL EtOAc was added. The aqueous layer was extracted twice more with EtOAc (100 mL). The combined organic layers were dried over $MgSO_4$, filtered, and concentrated in vacuo to afford a yellow solid. The crude product was purified by silica gel column chromatography. Yield 76%. $^1$H NMR (500 MHz, DMSO-d6):δ ppm 12.29 (s, 1H), 10.80 (s, 1H), 7.95 (s, 1H), 7.66 (d, J=10.0 Hz, 1H), 7.40 (d, J=10.0 Hz, 1H), 6.82 (s, 1H), 3.32 (s, 2H). $^{13}$C NMR (126 MHz, DMSO-d6): δ ppm 165.80, 160.80, 141.73, 141.26, 136.58, 125.54, 120.18, 115.24, 109.62, 105.68, 44.05. ESIMS (m/z) 305 $[M+H]^+$, 327 $[M+Na]^+$, 303 $[M-H]^-$

7-amino-4-methyl-1-(prop-2-ynyl)quinolin-2(1H)-one (S7)

To compound S3 (2.0 mmol, 348 mg) in DMF (0.2 M) was added 1.0 equiv of 10 M NaOH and stirred at room temperature for 15 min. Propargyl bromide (178 uL, 2.0 mmol, 1.0 equiv) was added drop wise and stirred at 60° C. After 12 h, water 100 mL, 50 mL EtOAc was added. The aqueous layer was extracted twice more with EtOAc (100 mL). The combined organic layers were dried over $MgSO_4$, filtered, and concentrated in vacuo to afford a yellow solid. The crude product was purified by silica gel column chromatography. Yield 80%. $^1$H NMR (500 MHz, MeOD): δ ppm 7.42 (d, J=10.0 Hz, 1H), 6.54-6.59 (m, 2H), 6.09 (s, 1H), 5.95 (s, 2H), 4.89 (s, 2H), 3.19 (S, 1H), 2.28 (s, 3H). $^{13}$C NMR (126 MHz, MeOD): δ ppm 161.05, 152.15, 148.06, 140.65, 127.14, 113.90, 111.51, 110.58, 97.58, 79.92, 74.48, 31.05, 18.96. ESIMS (m/z) 213 $[M+H]^+$, 235 $[M+Na]^+$, 211 $[M-H]^-$ chloro-N-(4-methyl-2-oxo-1-(prop-2-ynyl)-1,2-dihydroquinolin-7-yl)acetamide (S8)

Prepared in similar way as compound S5, except compound S7 used in place of compound S3. Yield 81%. $^1$H NMR (500 MHz, MeOD): δ ppm 11.20 (s, 1H), 8.06 (s, 1H), 7.75 (d, J=10.0 Hz, 1H), 7.57-7.60 (m, 2H), 6.44 (s, 1H), 4.95 (s, 2H), 4.42 (s, 2H), 3.27-3.28 (m, 1H), 2.40 (s, 3H). $^{13}$C NMR (126 MHz, MeOD): δ ppm 166.14, 161.09, 148.23, 141.90, 139.57, 127.23, 118.97, 117.74, 114.57, 105.28, 79.60, 75.44, 44.52, 31.76, 19.32. ESIMS (m/z) 289 $[M+H]^+$, 311 $[M+Na]^+$, 287 $[M-H]^-$

Scheme 2

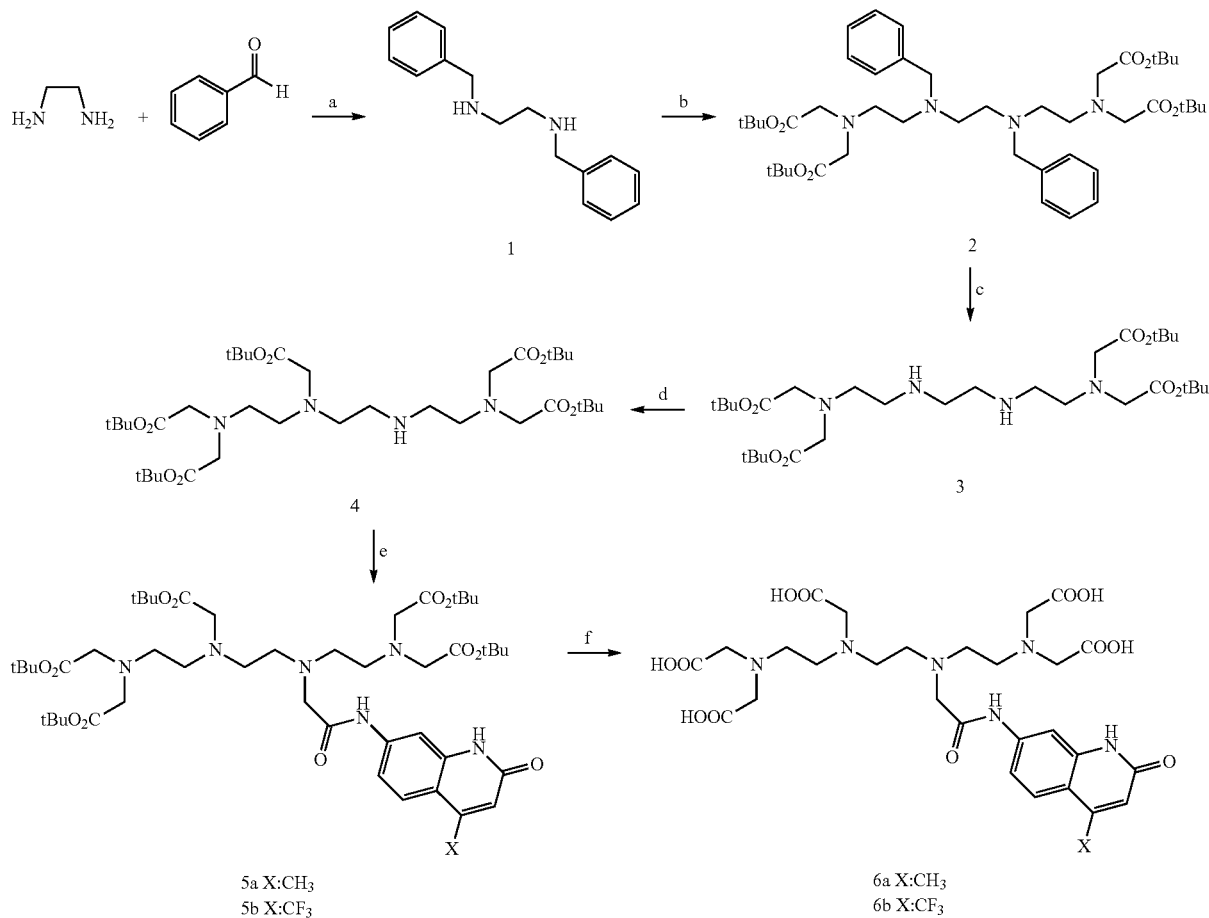

N,N'-(Benzyl)ethylenediamine (1)

To a solution of ethylenediamine (2.82 mL, 20.0 mmol) in dry methanol (100 mL) was added benzaldehyde (4.06 mL, 40.0 mmol, 2 equiv). The solution was refluxed for 10 h and then cooled via an ice bath. Addition of NaBH$_4$ (3.25 g, 86 mmol, 4.3 equiv) was performed slowly and in small portions to prevent boiling, and the reaction mixture was stirred for 4 h until completion. The solvent was evaporated in vacuo, and then saturated NaHCO$_3$ (50 mL), water (50 mL) and dichloromethane (200 mL) were added. The aqueous layer was extracted twice more with dichloromethane (100 mL). The combined organic layers were dried over MgSO$_4$, filtered, and concentrated in vacuo to afford a waxy, yellow solid. Product was purified by silica column chromatography to afford 1 as yellow oil. Yield 62%. $^1$H NMR (500 MHz, CDCl$_3$): δ ppm 7.36 (d, J=5.0 Hz, 8H), 7.30 (m, 2H), 3.81 (s, 4H), 2.79 (s, 4H), 1.63 (s, 2H). $^{13}$C NMR (126 MHz, CDCl$_3$): δ ppm 140.68, 128.45, 128.20, 126.96, 54.02, 48.92. 241. ESIMS (m/z) 241 [M+H]$^+$, 263 [M+Na]$^+$, 239 [M−H]$^-$ di-tert-butyl 6,9-dibenzyl-3,12-bis(2-tert-butoxy-2-oxoethyl)-3,6,9,12-tetraazatetradecane-1,14-dioate (2)

To a solution of compound 1 (2.40 g, 10.0 mmol) and compound S2 (7.39 g, 21.0 mmol, 2.1 equiv) in DMF was added sodium carbonate (3.17 g, 3.0 equiv). The solution was heated for 24 hours at 60° C. under N$_2$. Sodium carbonate was removed by filtration. The filtrate was washed with H$_2$O and aqueous phase extracted twice with EtOAc. The combined organic layers were dried over MgSO$_4$, filtered, and concentrated in vacuo. Product was purified by silica column chromatography to afford 2 as yellow oil. Yield 89%. $^1$H NMR (500 MHz, CDCl$_3$): δ ppm 7.24-7.26 (m, 10H), 3.55 (s, 4H), 3.37 (s, 8H), 2.75-2.77 (m, 4H), 2.55-2.57 (m, 8H), 1.41 (s, 36H). $^{13}$C NMR (126 MHz, CDCl$_3$): δ ppm 170.69, 139.64, 128.80, 128.09, 126.73, 80.71, 59.23, 56.14, 53.07, 52.13, 28.17. ESIMS (m/z) 783 [M+H]$^+$, 805 [M+Na]$^+$, 781 [M−H]$^-$ di-tert-butyl 3,12-bis(2-tert-butoxy-2-oxoethyl)-3,6,9,12-tetraazatetradecane-1,14-dioate (3)

To a solution of compound 2 (1.62 g, 2.0 mmol) in methanol (7 mL) was added Pd/C (200 mg, 10 wt %). Hydrogen gas was bubbled through the solution for 3 min, and then the reaction mixture was stirred under hydrogen for 18 h. The Pd/C was filtered out over Celite, rinsing well with methanol, and the filtrate was evaporated to dryness in vacuo. The crude product was purified by silica gel column chromatography. Product fractions were combined and concentrated in vacuo to afford the product 3 as a waxy yellow solid. Yield 95%. $^1$H NMR (500 MHz, MeOD):δ ppm 3.55

(s, 8H), 3.13-3.23 (m, 12H), 1.49 (s, 36H). $^{13}$C NMR (126 MHz, MeOD): δ ppm 172.01, 81.64, 56.48, 50.83, 46.11, 43.39. ESIMS (m/z) 603 [M+H]$^+$, 625 [M+Na]$^+$, 601 [M−H]$^−$ di-tert-butyl 3,6,12-tris(2-tert-butoxy-2-oxoethyl)-3,6,9,12-tetraazatetradecane-1,14-dioate (4)

To a solution compound 3 (1.2 g, 2.0 mmol) and sodium carbonate (423 mg, 4.0 mmol, 2.0 equiv) in dry acetonitrile was added dropwise a solution of tertbutyl bromoacetate (295 uL, 2.0 mmol, 1.0 equiv). The reaction mixture was stirred for 18 h at room temperature. Sodium carbonate was filtered and the filtrate concentrated in vacuo to dryness. EtOAc and water were added and aqueous layer were extracted twice with EtOAc. The combined organic layers were dried over MgSO$_4$, filtered, and concentrated in vacuo to afford a waxy, yellow solid. Product was purified by silica column chromatography to afford compound 4 as yellow oil. Yield 90%. $^1$H NMR (500 MHz, CDCl$_3$):δ ppm 2.82-3.18 (m, 16H), 2.40-2.50 (m, 6H), 1.10-1.15 (m, 45H). ESIMS (m/z) 717 [M+H]$^+$, 739 [M+Na]$^+$, 715 [M−H]$^−$ di-tert-butyl 3,6,12-tris(2-tert-butoxy-2-oxoethyl)-9-(2-(4-methyl-2-oxo-1,2-dihydroquinolin-7-ylamino)-2-oxoethyl)-3,6,9,12-tetraazatetradecane-1,14-dioate (5a)

To compound 4 (143 mg, 0.2 mmol) and compound S5 (55 mg, 0.22 mmol, 1.1 equiv) in 10 mL DMF was added sodium carbonate (42 mg, 0.4 mmol, 2.0 equiv), and the reaction mixture was heated to 60° C. for 24 h under nitrogen. After cooling to room temperature, the reaction mixture was diluted with EtOAc, washed with H$_2$O and brine, aqueous layer were extracted twice with EtOAc. The combined organic layers were dried over MgSO$_4$, filtered, and concentrated in vacuo to afford a waxy, yellow solid. Product was purified by silica column chromatography to afford 5a as yellow oil. Yield 60%. $^1$H NMR (500 MHz, CDCl$_3$):δ ppm 7.55-7.78 (m, 3H), 6.41 (s, 1H), 3.34-3.46 (m, 12H), 2.74-2.84 (m, 12H), 2.44 (s, 3H), 1.40-1.45 (m, 45H). ESIMS (m/z) 931 [M+H]$^+$, 953 [M+Na]$^+$, 929 [M−H]$^−$ di-tert-butyl 3,6,12-tris(2-tert-butoxy-2-oxoethyl)-9-(2-oxo-2-(2-oxo-4-(trifluoromethyl)-1,2-dihydroquinolin-7-ylamino)ethyl)-3,6,9,12-tetraazatetradecane-1,14-dioate (5b)

Prepared in a similar way as compound 5a, except compound S6 was used instead of compound S5. Yield 55%. $^1$H NMR (500 MHz, CDCl$_3$):δ ppm 7.63-8.19 (m, 3H), 6.90 (s, 1H), 3.34-3.47 (m, 12H), 2.74-2.88 (m, 12H), 1.40-1.45 (m, 45H). ESIMS (m/z) 985 [M+H]$^+$, 1007 [M+Na]$^+$, 983 [M−H]$^−$ Scheme 3

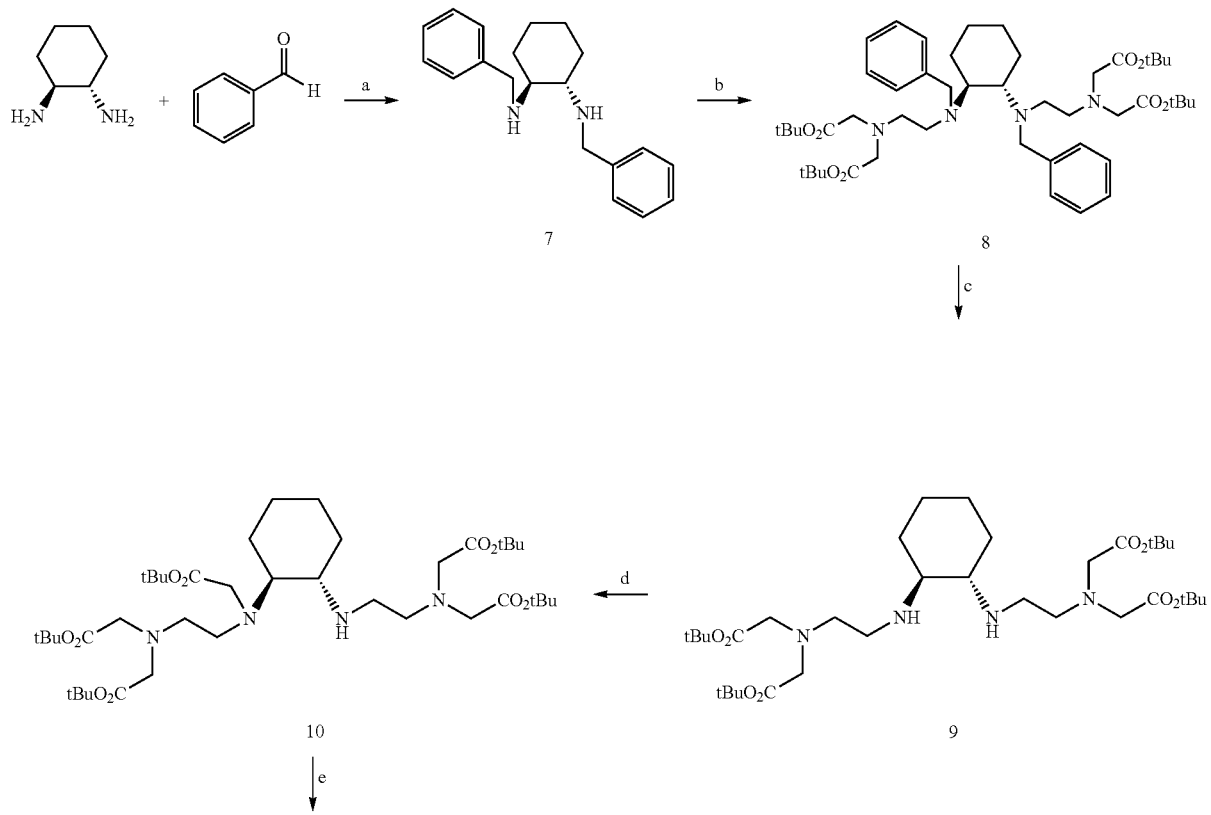

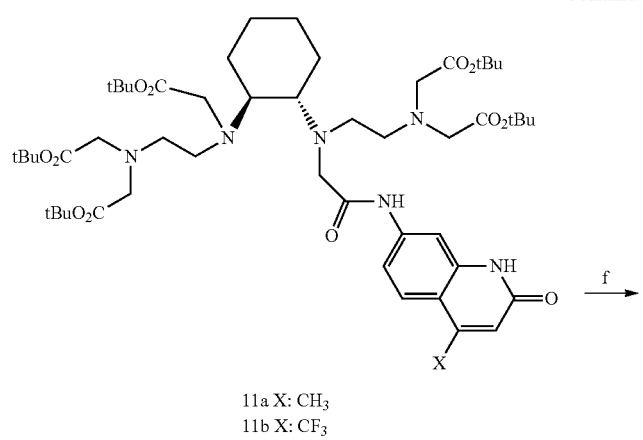
11a X: CH₃
11b X: CF₃ f →

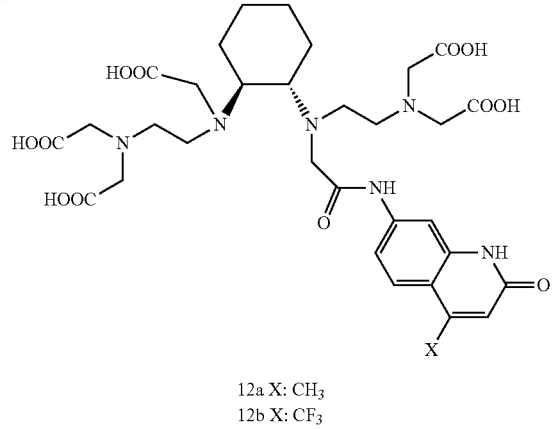
12a X: CH₃
12b X: CF₃

(1S,2S)—N1,N2-dibenzylcyclohexane-1,2-diamine (7)

To a solution of (1S,2S)-cyclohexane-1,2-diamine (1.14 g, 10.0 mmol) in dry methanol was added benzaldehyde (2.03 mL, 20.0 mmol, 2 equiv). The solution was refluxed for 4 h and then cooled via an ice bath. Addition of NaBH₄ (1.62 g, 43.0 mmol, 4.3 equiv) was performed slowly and in small portions to prevent boiling, and the reaction mixture was stirred for 12 h until completion. The solvent was evaporated in vacuo, and then saturated NaHCO₃ (50 mL), water (50 mL) and dichloromethane (200 mL) were added. The aqueous layer was extracted twice more with dichloromethane (100 mL). The combined organic layers were dried over MgSO₄, filtered, and concentrated in vacuo to afford a waxy, yellow solid. Product was purified by silica column chromatography to afford 7 as yellow oil. Yield 69%. $^1$H NMR (500 MHz, CDCl₃):δ ppm 7.29-7.40 (m, 8H), 7.23-7.29 (m, 2H), 3.92 (d, J=10.0 Hz, 2H), 3.69 (d, J=10.0 Hz, 2H), 2.28-2.35 (m, 2H), 2.14-2.26 (m, 4H), 1.76 (m, 2H), 1.21-1.33 (m, 2H), 1.03-1.14 (m, 2H), $^{13}$C NMR (126 MHz, CDCl₃): δ ppm 141.15, 128.40, 128.15, 126.84, 60.92, 50.92, 31.58, 25.18. ESIMS (m/z) 295 [M+H]⁺, 317 [M+Na]⁺, 293 [M–H]⁻ tert-butyl 2,2',2'',2'''-(2,2'-(1S,2S)-cyclohexane-1,2-diylbis(benzylazanediyl)bis(ethane-2,1-diyl))bis(azanetriyl)tetraacetate (8)

To a solution of compound 7 (294 mg, 1.0 mmol) and compound S2 (739 mg, 2.1 mmol, 2.1 equiv) in DMF was added sodium carbonate (317 mg, 3 mmol, 3 equiv). The solution was heated for 24 h at 60° C. under N₂. Sodium carbonate was removed by filtration. The filtrate was washed with H₂O and aqueous phase extracted twice with EtOAc. The combined organic layers were dried over MgSO₄, filtered, and concentrated in vacuo. Product was purified by silica column chromatography to afford 8 as yellow oil. Yield 88%. $^1$H NMR (500 MHz, CDCl₃):δ ppm 7.07-7.28 (m, 10H), 3.73 (d, J=10.0 Hz, 2H), 3.37 (d, J=10.0 Hz, 2H), 3.26 (s, 8H), 2.53-2.71 (m, 10H), 1.35-1.63 (m, 43H). $^{13}$C NMR (126 MHz, CDCl₃): δ ppm 170.54, 141.11, 128.24, 127.80, 126.36, 80.46, 61.02, 60.23, 55.96, 54.82, 53.86, 48.49, 28.08, 26.61, 26.04, 20.92, 14.17. ESIMS (m/z) 837 [M+H]⁺, 859 [M+Na]⁺, 835 [M–H]⁻ tert-butyl 2,2',2'',2'''-(2,2'-(1S,2S)-cyclohexane-1,2-diylbis(azanediyl)bis(ethane-2,1-diyl)bis(azanetriyl)tetraacetate (9)

To a solution of compound 8 (836 mg, 1.0 mmol) in methanol (7 mL) was added Pd/C (150 mg, 10 wt %). Hydrogen gas was bubbled through the solution for 3 min, and then the reaction mixture was stirred under hydrogen for 24 h. The Pd/C was filtered out over Celite, rinsing well with methanol, and the filtrate was evaporated to dryness in vacuo. The crude product was purified by silica gel column chromatography. Product fractions were combined and concentrated in vacuo to afford the product 8 as a waxy yellow solid. Yield 90%. $^1$H NMR (500 MHz, MeOD):δ ppm 3.20-3.70 (m, 18H), 1.49-1.87 (m, 42H). $^{13}$C NMR (126 MHz, MeOD): δ ppm 172.15, 81.80, 56.71, 56.48, 51.54, 48.71, 44.20, 27.36, 25.43, 21.42. ESIMS (m/z) 657 [M+H]⁺, 679 [M+Na]⁺, 655 [M–H]⁻ tert-butyl 2,2'-(2-(((1S,2S)-2-((2-(bis(2-tert-butoxy-2-oxoethyl)amino)ethyl)(2-tert-butoxy-2-oxoethyl)amino)cyclohexylamino)ethylazanediyl)diacetate (10)

To a solution of compound 9 (328 mg, 0.5 mmol) and sodium carbonate (105.99 mg, 2 mmol, 2.0 equiv) in dry acetonitrile was added dropwise a solution of tertbutyl bromoacetate (74 uL, 0.5 mmol, 1.0 equiv). The reaction mixture was stirred at 18 h at room temperature. Sodium carbonate was filtered and the filtrate concentrated in vacuo to dryness. EtOAc and water were added and aqueous layer were extracted twice with EtOAc. The combined organic layers were dried over MgSO₄, filtered, and concentrated in vacuo to afford a waxy, yellow solid. Product was purified by silica column chromatography to afford 10 as yellow oil. Yield 85%. $^1$H NMR (500 MHz, CDCl₃):δ ppm 3.30-3.40 (m, 20H), 1.10-1.45 (m, 42H). $^{13}$C NMR (126 MHz, CDCl₃): δ ppm 170.58, 170.48, 170.30, 170.14, 82.48, 80.92, 80.73, 80.33, 59.86, 56.55, 56.11, 55.85, 52.90, 50.54, 43.15, 41.60. ESIMS (m/z) 771 [M+H]⁺, 793 [M+Na]⁺, 769 [M–H]⁻ tert-butyl 2,2'-(2-(((1S,2S)-2-((2-(bis(2-tert-butoxy-2-oxoethyl)amino)ethyl)(2-(4-methyl-2-oxo-1,2-dihydroquinolin-7-ylamino)-2-oxoethyl)amino)cyclohexyl)(2-tert-butoxy-2-oxoethyl)amino)ethylazanediyl)diacetate (11a)

Prepared in a similar way as compound 5a, except compound 10 was used instead of compound 4. Yield 52%. $^1$H NMR (500 MHz, CDCl$_3$):δ ppm 7.52-7.64 (m, 3H), 6.38 (m, 1H), 2.15-3.44 (m, 25H), 1.23-1.43 (m, 53H). ESIMS (m/z) 985 [M+H]$^+$, 1007 [M+Na]$^+$, 983 [M−H]$^−$ tert-butyl 2,2'-(2-(((1S,2S)-2-((2-(bis(2-tert-butoxy-2-oxoethyl)amino)ethyl)(2-tert-butoxy-2-oxoethyl)amino)cyclohexyl)(2-oxo-2-(2-oxo-4-(trifluoromethyl)-1,2-dihydroquinolin-7-ylamino)ethyl)amino)ethylazanediyl)diacetate (11b)

Prepared in a similar way as compound 5b, except compound 10 was used instead of compound 4. Yield 52%. $^1$H NMR (500 MHz, CDCl$_3$):δ ppm 7.44-7.62 (m, 3H), 6.87 (s, 1H), 2.50-3.50 (m, 22H), 1.33-1.44 (m, 53H). ESIMS (m/z) 985 [M+H]$^+$, 1007 ESIMS (m/z) 1039 [M+H]$^+$, 1061 [M+Na]$^+$, 1037 [M−H]$^−$ Scheme 4

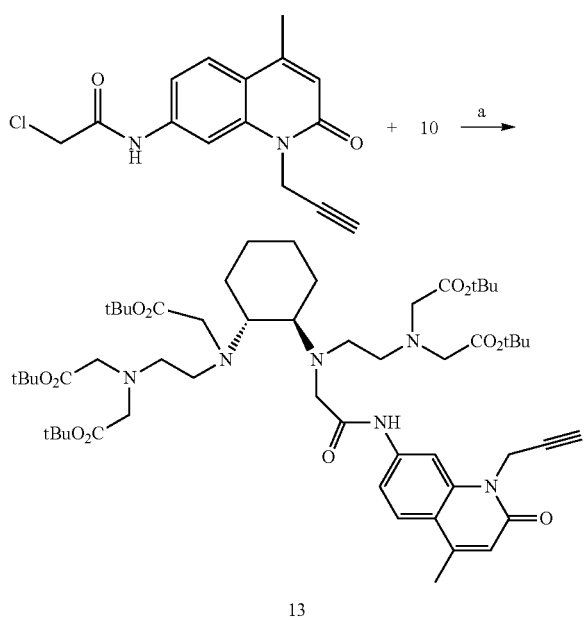

13

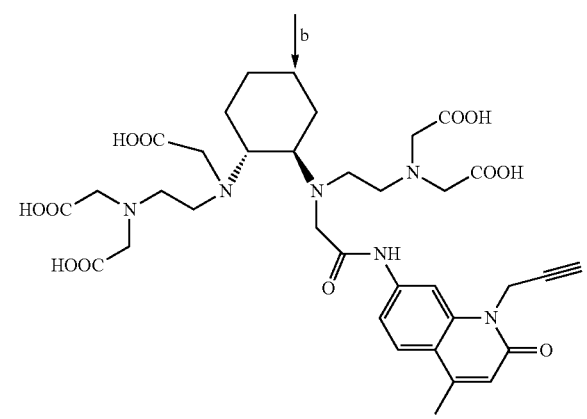

14

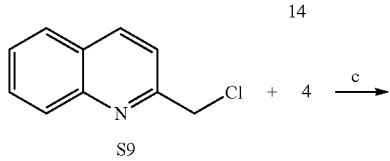

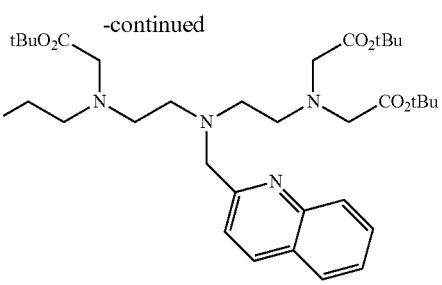

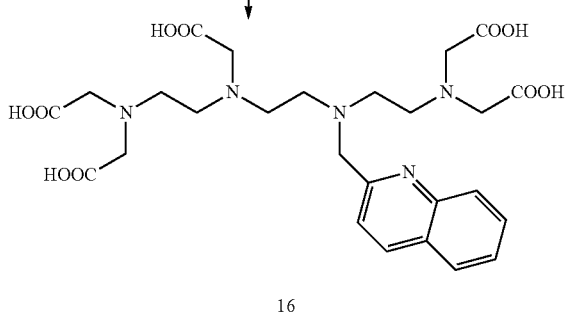

16 tert-butyl 2,2'-(2-(((1S,2S)-2-((2-(bis(2-tert-butoxy-2-oxoethyl)amino)ethyl)(2-(4-methyl-2-oxo-1-(prop-2-ynyl)-1,2-dihydroquinolin-7-ylamino)-2-oxoethyl)amino)cyclohexyl)(2-tert-butoxy-2-oxoethyl)amino)ethylazanediyl)diacetate (13)

Prepared in a similar way as compound 11a, except compound S8 was used instead of compound S5. Yield 52%. $^1$H NMR (500 MHz, CDCl$_3$):δ ppm 7.82-8.10 (m, 2H), 7.56 (m, 1H), 6.49 (s, 1H), 5.09 (s, 2H), 4.24 (s, 1H). ESIMS (m/z) 1023 [M+H]$^+$, 1045 [M+Na]$^+$, 1021 [M−H]$^−$ di-tert-butyl 3,6,12-tris(2-tert-butoxy-2-oxoethyl)-9-(quinolin-2-ylmethyl)-3,6,9,12-tetraazatetradecane-1,14-dioate (15)

Prepared in a similar way as compound 5a, except compound S9 was used instead of compound 5a. Yield 75%. $^1$H NMR (500 MHz, CDCl$_3$):δ ppm 8.10 (d, J=5.0 Hz, 1H), 7.99 (d, J=5.0 Hz, 1H), 7.75 (d, J=5.0 Hz, 1H), 7.60-7.66 (m, 2H), 7.47 (t, J=5.0 Hz, 1H), 3.95 (s, 2H), 3.46-3.51 (m, 2H), 3.39 (s, 4H), 3.32-3.35 (m, 4H), 2.72-2.86 (m, 12H), 1.34-1.43 (m, 45H). $^{13}$C NMR (126 MHz, CDCl$_3$): δ ppm 171.02, 169.32, 166.73, 160.96, 147.90, 136.80, 129.69, 129.35, 127.96, 127.79, 126.44, 121.56, 81.97, 81.25, 61.99, 58.78, 56.98, 56.45, 53.24, 52.39, 52.00, 49.75, 47.56, 44.74, 28.52. ESIMS (m/z) 858 [M+H]$^+$, 880 [M+Na]$^+$, 856 [M−H]$^−$ Compound 6a, 6b, 12a, 12b, 14, and 16.

To the corresponding ester was added deprotection mixture (TFA/CH$_2$Cl$_2$/iPr$_3$SiH, 5:5:1.8, v/v, 11.8 mL). After stirring for 24 h, toluene (10 mL) was added, and the solvent was removed by evaporation under reduced pressure. Ethyl acetate (5 mL) was added and the heterogeneous mixture was stirred for 1 h at 60° C. The resulting precipitate was filtered off, washed with ethyl acetate (5 mL), and mixed with water (20 mL). Lyophilization afforded the pure compound.

Compound iii

A cyclohexyl analog of the metal chelator was prepared with methylenecarboxylate pendant groups and a sensitizing chromophore (carbostyril 124) appended to one of the central nitrogens (compound iii). The synthesis of compound iii was remarkably efficient (8 steps, 45% overall yield). Moreover, it can be scaled up and altered to prepare different derivatives, as evidenced by the incorporation of a single chromophore into the structure. Given its position in the molecule, the amide oxygen between the cyclohexyl nitrogen and the chromophore may coordinate to a bound Tb ion. This coordination in turn would allow for efficient sensitization of metal luminescence and result in a high quantum yield of emission. Indeed this has proved to be the case. The quantum yield of compound iii exceeded 50% in water, making it among the most efficient luminescent Tb complexes known.

Reagents and conditions: (a) Boc2O, DCM, 0° C.-RT, 12 h, 92%. (b) PhCHO, MeOH, reflux, 10 h then NaBH4 (2.1 equiv), 0° C.-RT, 4 h, 95%. (c) BrCH2CH2Br, DMF, 60° C., 24 h, 80%. (d) TFA/DCM, RT, 24 h then t-butyl bromoacetate (4.0 equiv), Na2CO3 (4.0 equiv), MeCN, 24 h, 85%. (e) Pd/C (10 wt %), H2, RT, 24 h, 90%. (f) t-butyl bromoacetate (1.0 equiv), Na2CO3 (1.0 equiv), MeCN, 18 h, 85%. (g) cs-124-COCH2Cl, Na2CO3, DMF, 60° C., 24 h, 60%. (h) TFA/CH2Cl2, RT, 24 h, 99%.

The introduction of two rigid cyclohexyl groups into the otherwise flexible backbone provides a degree of pre-organization to the molecule that serves to increase thermodynamic and kinetic stability while preserving fast metallation kinetics. Polyaminocarboxylates with cyclohexane incorporated into the backbone are not unprecedented. CHX-A-DTPA has been extensively tested as a binder of $^{111}$In, $^{86/90}$Y and other radiometals since its introduction in the early 1990's, and analogs of triethylene tetraamine hexaacetic acid (TTHA) with a single ring structure have been described. A DTPA analog with two cyclohexane rings was also described as a Gd complexing agent.

Results and Discussion

All of the complexes prepared show characteristic lanthanide emission spectra. UV-Vis absorption spectra closely matched those of previously reported carbostyril-sensitized complexes. Measurement of luminescent lifetimes in H$_2$O and D$_2$O and fitting to the Horrocks and Sudnick equation[23] showed that water is excluded from the inner coordination sphere (Table 1). Most notably, exceptionally high quantum yields of 0.50 and 0.40 were observed in aqueous buffer for the Tb(III) and Eu(III) complexes of 12a and 12b, respectively, which are among the highest reported in the literature. The efficient emission and lack of bound waters support the hypothesis that inner substitution positions the sensitizer such that it remains coordinated to the metal center.

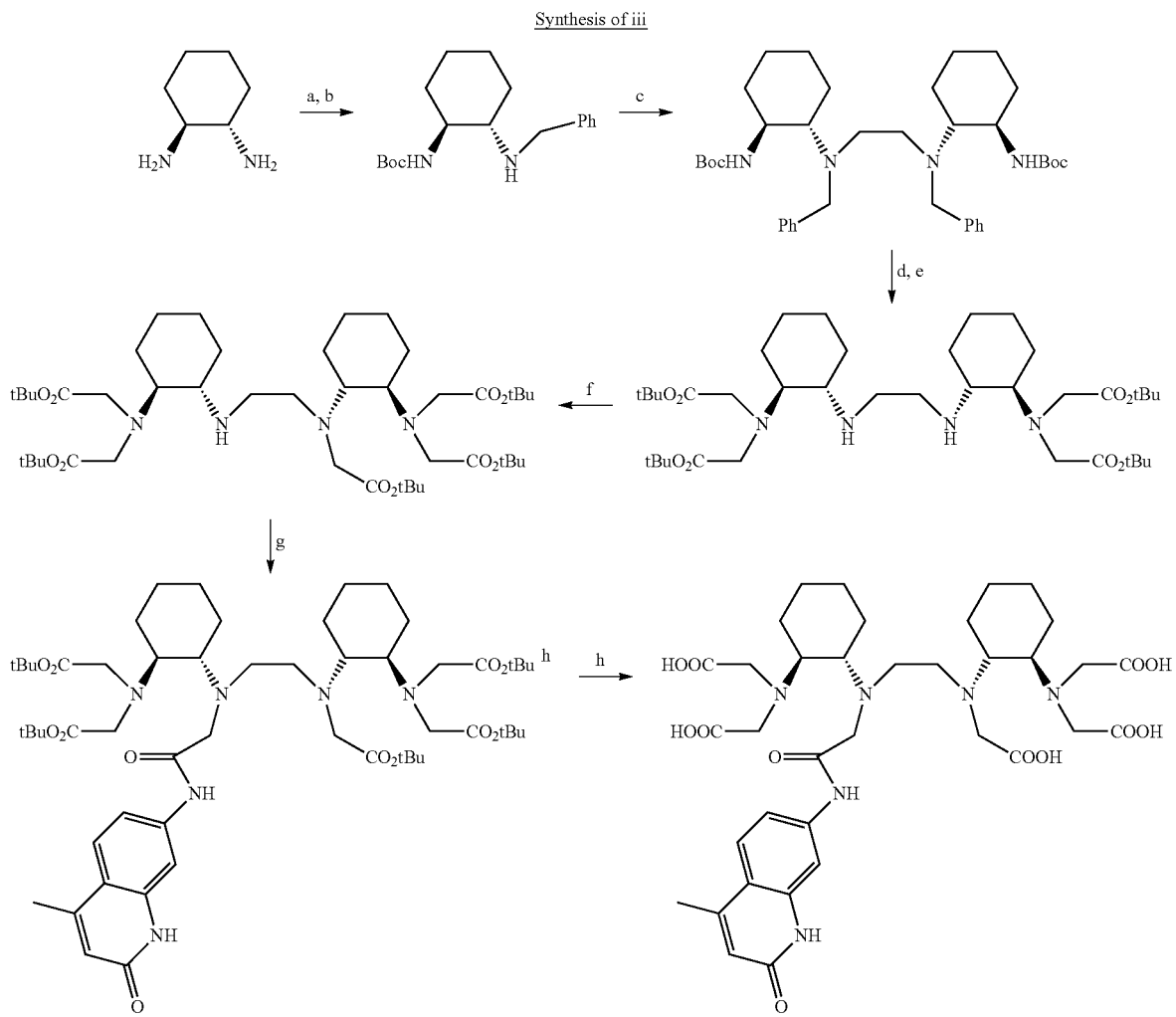

Synthesis of iii

TABLE 1

Measurements of luminescent lifetimes in $H_2O$ and in $D_2O$, number of water in inner coordination sphere, and quantum yield for select Tb(III) and Eu(III) complexes.

| Compound | $t_{H2O}$ | $t_{D2O}$ | Number of Water | Quantum Yield |
|---|---|---|---|---|
| Tb-12a | 1.81 | 1.83 | 0.03 | 0.50 |
| Tb-6a | 1.91 | 1.93 | 0.02 | 0.54 |
| Eu-12b | 1.08 | 1.54 | 0.29 | 0.40 |
| Eu-6b | 0.97 | 1.38 | 0.32 | 0.36 |

Practical use of lanthanide luminophores in solution phase bioassays or as imaging probes requires stable metal retention at high dilution in the presence of competing chelators or other metals. In general, cryptates or macrocycles are more kinetically inert than relatively flexible, linear chelators.[4] However, they typically have slow metal association kinetics and require metallation at elevated temperatures, which complicates their use as antibody conjugates or with other heat-sensitive preparations (the Lumi4-Tb cryptate is a notable exception). Introduction of a pre-organized, cyclic moiety into an otherwise linear chelator can induce rigidity and yield more kinetically and/or thermodynamically stable complexes.[24] For example, incorporation of trans-1,2 diaminocyclohexane into the backbone of DTPA and TTHA improved the kinetic stability of radiometal complexes.[25-26] Ge and Selvin reported enhanced kinetic stability of a 9-dentate polyaminocarboxylate chelate that incorporated 1-oxa-4,7-diazacyclononane.[20]

Figure 2:
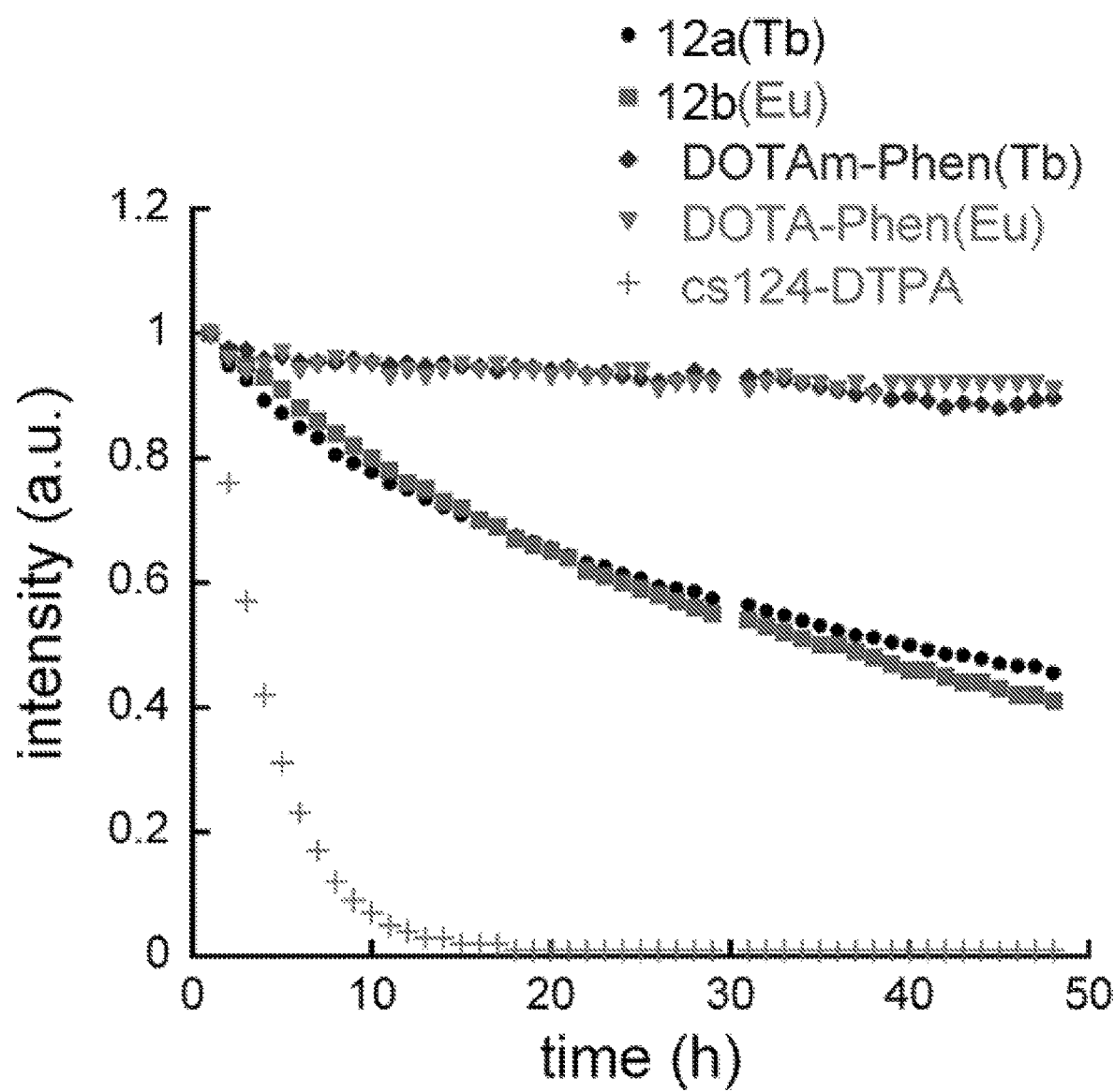
FIG. 2 is a graph of the relative kinetic stability as measured by the luminescence signal intensity at ca. 545 nm (for Tb(III) complexes) or 620 nm (for Eu(III) complexes) for various dilute aqueous solutions (5 nM) of the indicated metal complexes in TBS buffer containing 1 mM EDTA.

The kinetic inertness of Tb-12a and Eu-12b was compared to the highly stable macrocycles Tb-DOTAm-Phen and Eu-DOTA-Phen and the linear complex, Tb-cs124-DTPA.[6,27] Luminescence intensity was monitored after dilution to 5 nM in tris-buffered saline (TBS, pH 7.6) that contained the competitive additive EDTA (1 mM) (FIG. 2). After 48 h in EDTA solution, Tb-12a and the DOTA-based complexes retain their integrity, whereas the linear DTPA complex is completely dissociated from Tb(III) after only 10 h. The cyclic TTHA-based complexes Tb-12a and Eu-12b were still more than 40% in emissive after 48 h. The EDTA challenge assay results show that incorporation of a cyclohexane ring into the TTHA backbone imparts considerable solution stability while preserving fast metallation kinetics.

In summary, we have demonstrated that cyTTHA is a versatile scaffold for preparing emissive lanthanide complexes. An efficient and flexible synthesis makes it possible to easily vary sensitizer moieties, and one may envision alteration of the number or type of chelating groups. Conjugation to biomolecules could be achieved by functionalizing the cyclohexane ring, as has been reported for similar diaminocyclohexane-derived chelators.[28-29] The carbostyril-sensitized complexes Tb-12a and Eu-12b have exceptional quantum yields of emission and excellent kinetic stability and are thus suitable for time-gated imaging and bioanalytical applications.

In order to show that high levels of kinetic inertness can be achieved with bis-diaminocycloalkyl chelators, compound iii and Tb were mixed together in buffer at a 1:1 ratio. Complete metallation, as judged by formation of green Tb luminescence, occurred in less than 15 min. The resulting complex was then diluted to a final concentration of 5 nM in buffer solution that contained a much higher concentration (1 mM) of a competing chelator, ethylene diamine tetraacetic acid (EDTA). By observing the metal luminescence over time, the kinetic inertness of compound iii relative to that of other known chelators was assessed.

Figure 3:
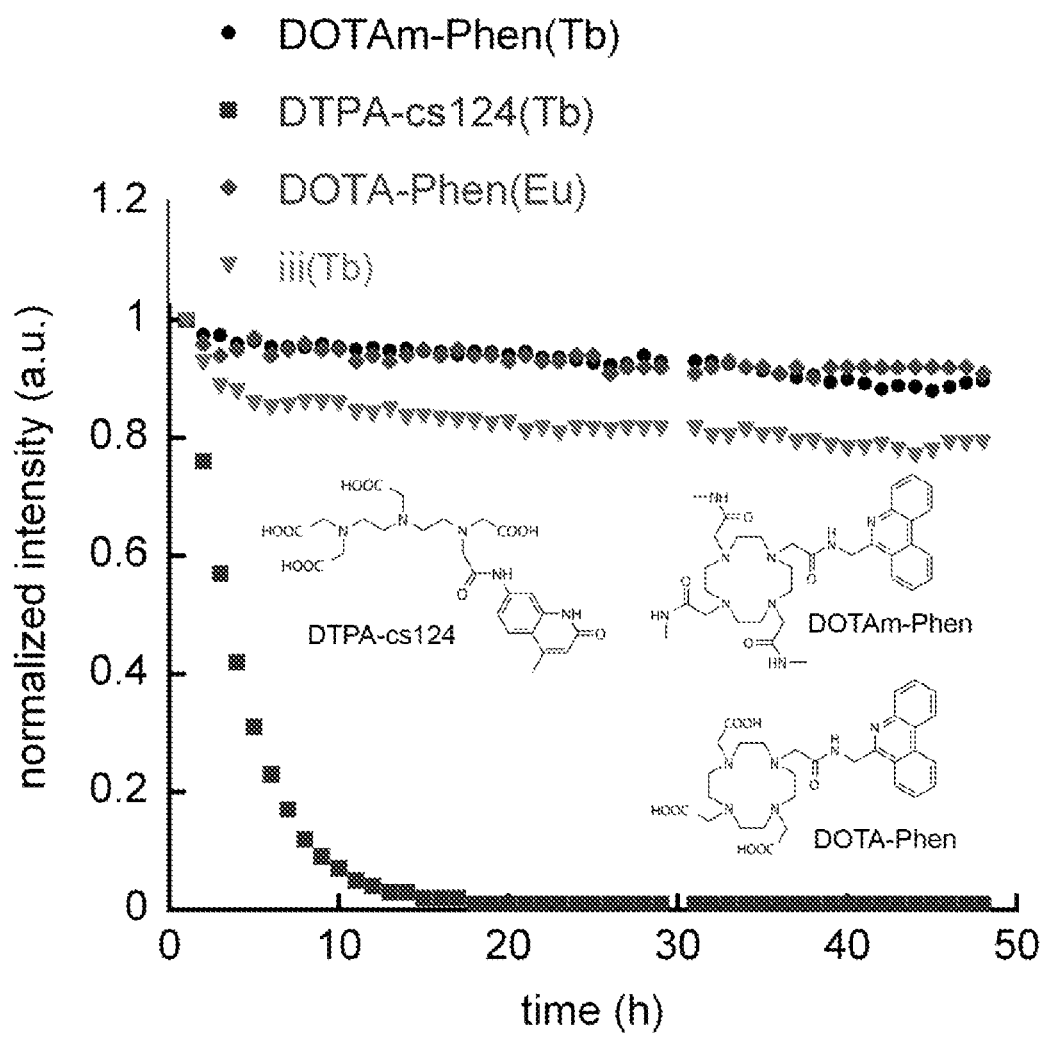
FIG. 3 is a graph of the relative kinetic stability as measured by the luminescence signal intensity at ca. 545 nm (for Tb(III) complexes) or 620 nm (for Eu(III) complexes) for various dilute aqueous solutions (5 nM) of the indicated metal complexes in TBS buffer containing 1 mM EDTA.

FIG. 3 shows the remarkable kinetic stability of the compound iii-Tb analog. Like the well known stable chelator DOTA and its amide-functionalized derivative (DOTAm), compound iii equilibrates with the EDTA solution in 2-3 h and remains essentially stable for 2 days. By contrast, the flexible DTPA complex is completely dissociated after ca. 10 h. The compound iii scaffold may be synthetically modified to exhibit similar stability and kinetic inertness with many other functionally useful metal ions.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES (1) Bunzli, J. C. Chem. Rev. 2010, 110, 2729.
(2) Heffern, M. C.; Matosziuk, L. M.; Meade, T. J. Chem Rev 2014, 114, 4496.
(3) Geissler, D.; Stufler, S.; Lohmannsroben, H. G.; Hildebrandt, N. J. Am. Chem. Soc. 2013, 135, 1102.
(4) Mathis, G.; Bazin, H. In Lanthanide Luminescence; Hanninen, P., Härmä, H., Eds.; Springer Berlin Heidelberg: 2011; Vol. 7, p 47.
(5) Rajendran, M.; Yapici, E.; Miller, L. W. Inorg Chem 2014, 53, 1839.
(6) Xu, J.; Corneillie, T. M.; Moore, E. G.; Law, G. L.; Butlin, N. G.; Raymond, K. N. J. Am. Chem. Soc. 2011, 133, 19900.
(7) Butler, S. J.; Lamarque, L.; Pal, R.; Parker, D. Chemical Science 2014, 5, 1750.
(8) Rajapakse, H. E.; Reddy, D. R.; Mohandessi, S.; Butlin, N. G.; Miller, L. W. Angew. Chem. Int. Ed. Engl. 2009, 48, 4990.
(9) Rajapakse, H. E.; Gahlaut, N.; Mohandessi, S.; Yu, D.; Turner, J. R.; Miller, L. W. Proc. Natl. Acad. Sci. USA 2010, 107, 13582.
(10) Mohandessi, S.; Rajendran, M.; Magda, D.; Miller, L. W. Chem.—Eur. J. 2012, 18, 10825.
(11) Zou, X.; Rajendran, M.; Magda, D.; Miller, L. W. Bioconjug Chem 2015, 26, 460.
(12) Prat, O.; Lopez, E.; Mathis, G. Anal Biochem 1991, 195, 283.
(13) Li, M.; Selvin, P. R. J. Am. Chem. Soc. 1995, 117, 8132.
(14) Xiao, M.; Selvin, P. R. J. Am. Chem. Soc. 2001, 123, 7067.
(15) Chen, J.; Selvin, P. R. Journal of Photochemistry and Photobiology A: Chemistry 2000, 135, 27.
(16) Reddy, D. R.; Pedro Rosa, L. E.; Miller, L. W. Bioconjugate Chem. 2011, 22, 1402.
(17) Heyduk, E.; Heyduk, T. Anal Biochem 1997, 248, 216.
(18) Li, M.; Selvin, P. R. Bioconjugate Chem. 1997, 8, 127.
(19) Krasnoperov, L. N.; Marras, S. A.; Kozlov, M.; Wirpsza, L.; Mustaev, A. Bioconjug Chem 2010, 21, 319.
(20) Ge, P.; Selvin, P. R. Bioconjug Chem 2008, 19, 1105.
(21) Burdinski, D.; Lub, J.; Pikkemaat, J. A.; Moreno Jalon, D.; Martial, S.; Del Pozo Ochoa, C. Dalton Trans 2008, 4138.
(22) Burdinski, D.; Pikkemaat, J. A.; Lub, J.; de Peinder, P.; Nieto Garrido, L.; Weyhermuller, T. Inorg Chem 2009, 48, 6692.

(23) Horrocks, W. D.; Sudnick, D. R. *Journal of the American Chemical Society* 1979, 101, 334.
(24) De Sousa, A. S.; Croft, G. J. B.; Wagner, C. A.; Michael, J. P.; Hancock, R. D. *Inorganic Chemistry* 1991, 30, 3525.
(25) Brechbiel, M. W.; Gansow, O. A.; Pippin, C. G.; Rogers, R. D.; Planalp, R. P. *Inorganic Chemistry* 1996, 35, 6343.
(26) Ouadi, A.; Loussouarn, A.; Morandeau, L.; Remaud, P.; Faivre-Chauvet, A.; Webb, J.; Gestin, J. F. *Eur J Med Chem* 2004, 39, 467.
(27) Weitz, E. A.; Chang, J. Y.; Rosenfield, A. H.; Morrow, E. A.; Pierre, V. C. *Chemical Science* 2013, 4, 4052.
(28) Gestin, J. F.; Benoist, E.; Loussouarn, A.; Mishra, A. K.; FaivreChauvet, A.; Chatal, J. F. *New J. Chem.* 1997, 21, 1021.
(29) Loussouarn, A.; Duflos, M.; Benoist, E.; Chatal, J.-F.; Le Baut, G.; Gestin, J.-F. *Journal of the Chemical Society, Perkin Transactions* 1 1998, 237.
(30) Price, E. W.; Orvig, C., *Chem Soc Rev* 2014, 43, 260-90.
(31) Heffern, M. C.; Matosziuk, L. M.; Meade, T. J., *Chem Rev* 2014, 114, 4496-539.
(32) Pierre, V. C.; Allen, M. J.; Caravan, P., *J Biol Inorg Chem* 2014, 19, 127-31.
(33) Bunzli, J. C., *Chem. Rev.* 2010, 110, 2729-2755.
(34) Hildebrandt, N.; Wegner, K. D.; Algar, W. R., *Coordination Chemistry Reviews* 2014, 273, 125-138.
(35) Rajendran, M.; Yapici, E.; Miller, L. W., *Inorg Chem* 2014, 53, 1839-53.
(36) Gestin, J. F.; Benoist, E.; Loussouarn, A.; Mishra, A. K.; FaivreChauvet, A.; Chatal, J. F., *New Journal of Chemistry* 1997, 21, 1021-1026.
(37) Loussouarn, A.; Duflos, M.; Benoist, E.; Chatal, J.-F.; Le Baut, G.; Gestin, J.-F., *Journal of the Chemical Society, Perkin Transactions* 1 1998, 237-242.
(38) Ouadi, A.; Loussouarn, A.; Morandeau, L.; Remaud, P.; Faivre-Chauvet, A.; Webb, J.; Gestin, J. F., *Eur J Med Chem* 2004, 39, 467-72.
(39) Sun, Y.; Martell, A. E.; Reibenspies, J. H.; Reichert, D. E.; Welch, M. J., *Inorg Chem* 2000, 39, 1480-6.

We claim:
1. A compound according to Formula I:

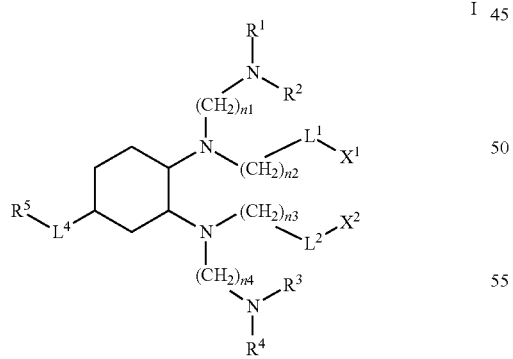

where n1 and n4 are 2;
where n2 and n3 are 1;
where $L^1$ and $L^2$ are none;
where $L^4$ is none or substituted and unsubstituted alkyl;
where $R^2$, $R^3$, and $R^4$ are each —$CH_2COOH$;
where $R^1$ is selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl and substituted and unsubstituted heteroaryl;
where $R^6$ is selected from the group consisting of H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2OR^9$, —$OC(O)R^9$, —$C(O)NR^9R^{10}$—$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol;
where $R^9$ and $R^{10}$ are each independently selected from H, substituted and unsubstituted alkyl, substituted and unsubstituted aryl, substituted and unsubstituted heteroaryl and substituted and unsubstituted heterocyclyl, or $R^9$ and $R^{10}$, together with the atoms to which they are attached, form a 5- to 7 membered heterocyclyl or heteroaryl;
where $X^1$ and $X^2$ are each independently selected from the group consisting of COOH, —$PO(OH)_2$, or a sensitizer so long as at least one of $X^1$ and $X^2$ is a sensitizer;
where each occurrence of the sensitizer is independently chosen from any one of the following formulas:

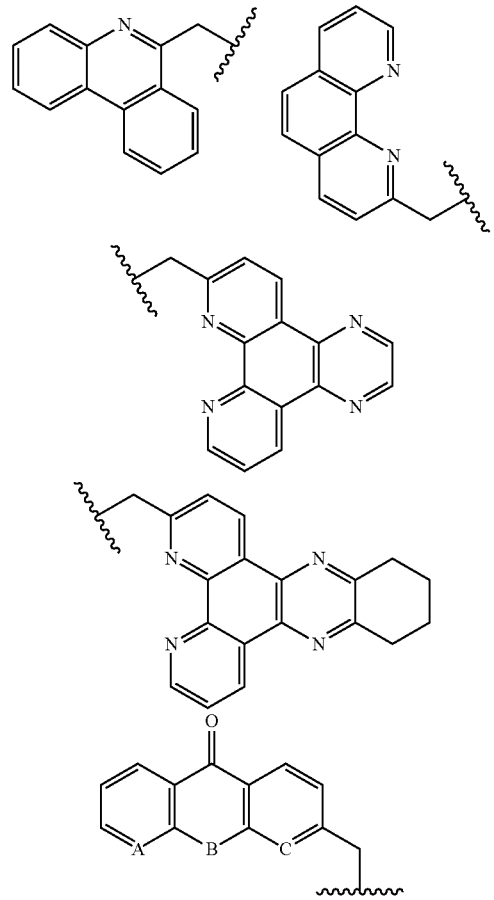

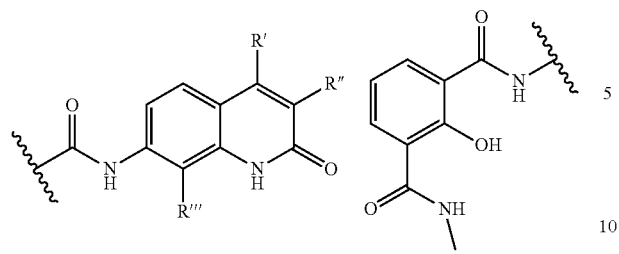
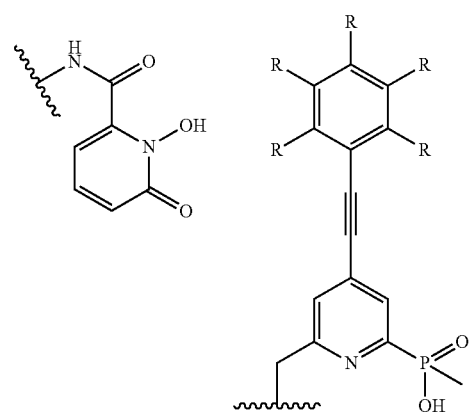
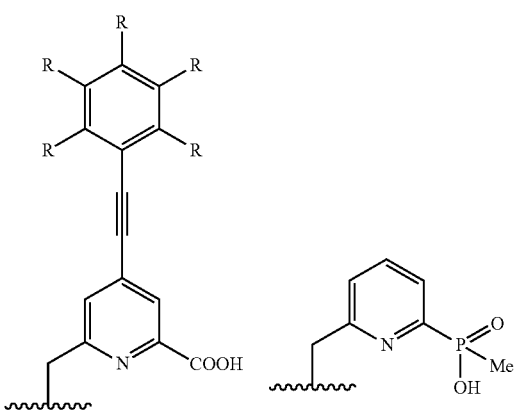
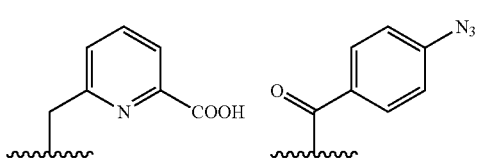
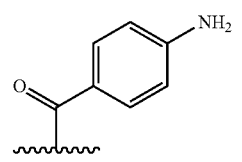
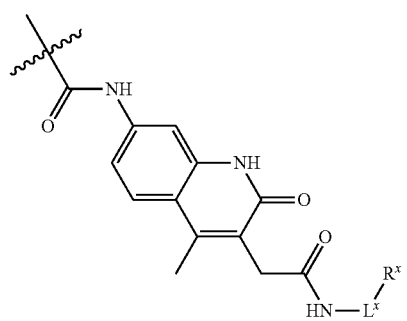
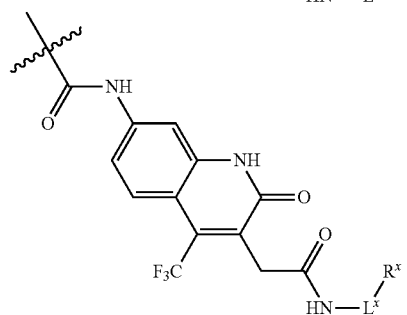
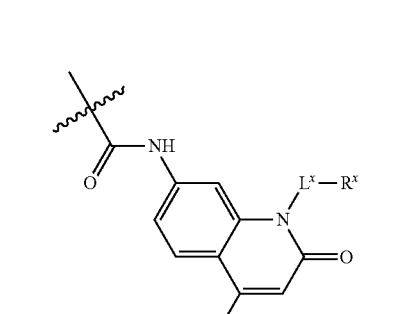
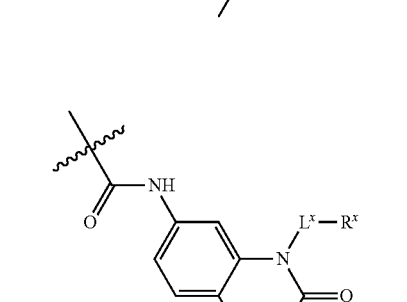
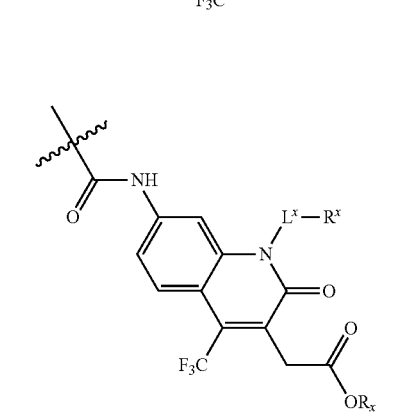

-continued

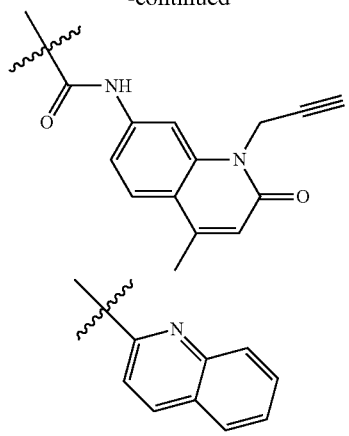

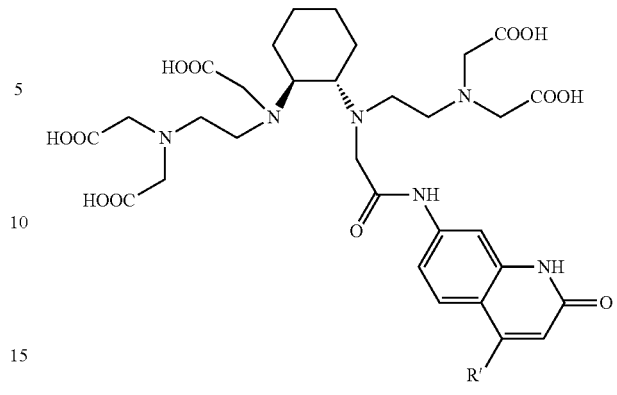

where A, B, and C are each independently selected from N and CH;

where R is independently selected at each occurrence from H and —OCH$_3$;

where R' is independently selected at each occurrence from —CH$_3$, —CF$_3$, and —CH$_2$COOH;

where R" is independently selected at each occurrence from H and —CH$_2$COOH;

where R''' is independently selected at each occurrence from H and —CH$_3$;

where $L^x$ is independently selected at each occurrence from none, substituted and unsubstituted alkyl, substituted and unsubstituted heteroalkyl, substituted and unsubstituted heteroaryl, and substituted and unsubstituted heterocycloalkyl; and where $R^x$ is independently selected at each occurrence from H, a halogen, substituted and unsubstituted alkyl, substituted and unsubstituted heteroalkyl, substituted and unsubstituted heteroaryl, substituted and unsubstituted heterocycloalkyl.

2. The compound according to claim 1, wherein the compound is according to Formula I;
wherein $R^1$ is —CH$_2$COOH; and
wherein $R^6$ is H.

3. The compound according to claim 1, wherein the compound is according to Formula II; and
wherein $R^1$ is —CH$_2$COOH.

4. The compound according to claim 1, wherein each occurrence of the sensitizer has a formula according to

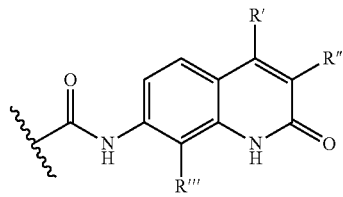

where R', R", and R''' are as defined above.

5. The compound according to claim 1, wherein at least one of $X^1$ and $X^2$ is —COOH.

6. The compound according to claim 1, wherein both $X^1$ and $X^2$ are a sensitizer.

7. The compound according to claim 1, wherein the compound is where R' is CH$_3$ or CF$_3$.

8. The compound according to claim 1, wherein the compound is

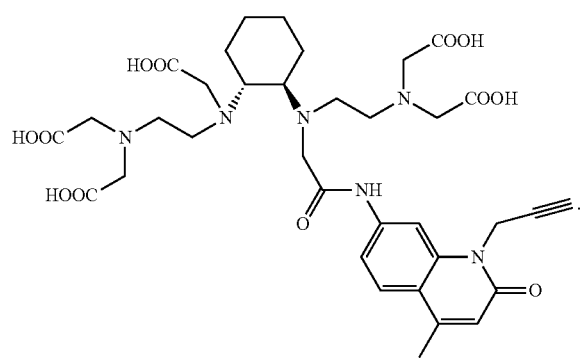 [SMILES: C#CCn1c(=O)cc(C)c2ccc(NC(=O)CN(CCN(CC(=O)O)CC(=O)O)[C@@H]3CCCC[C@H]3N(CCN(CC(=O)O)CC(=O)O)CC(=O)O)cc21]

9. The compound according to claim 1, wherein the compound is selected from the group consisting of

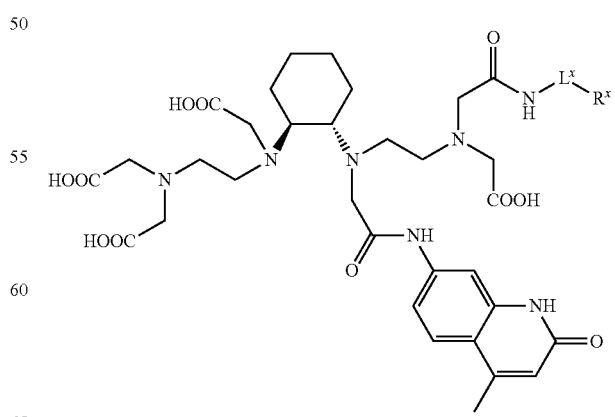

73
-continued
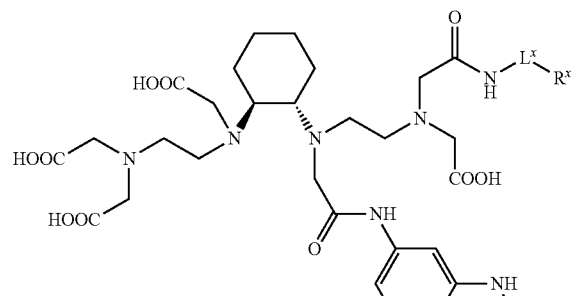
74
-continued
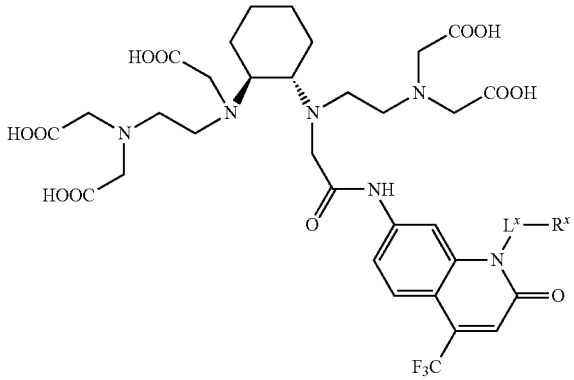
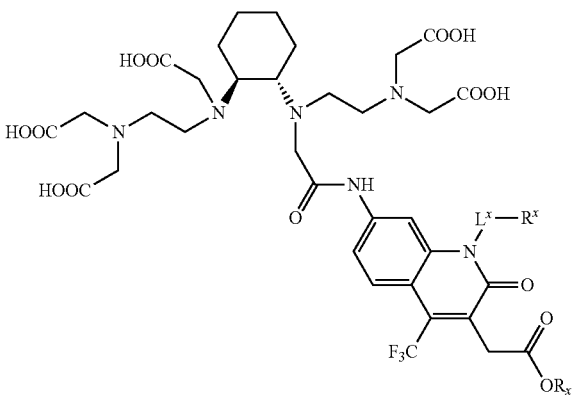
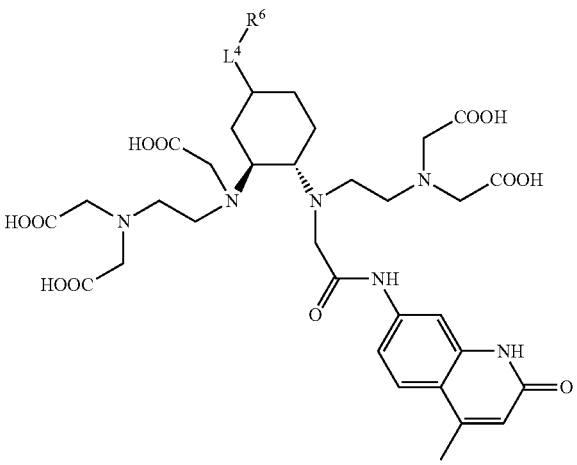
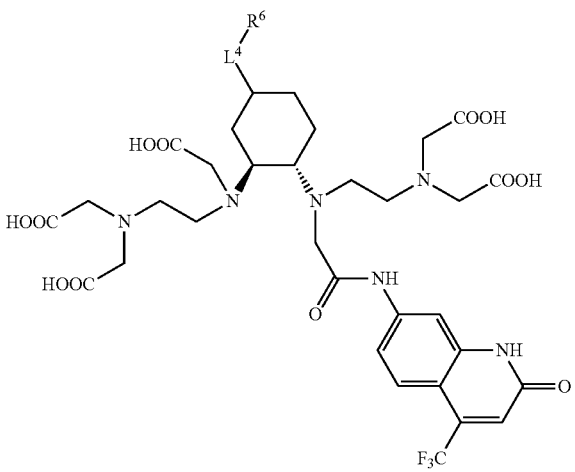

-continued

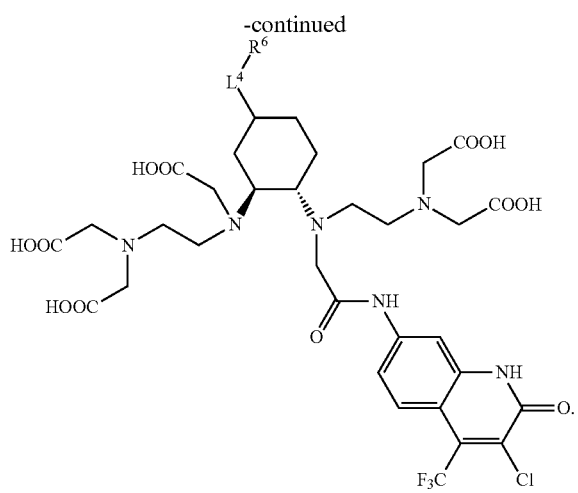

10. A luminescent complex formed between a compound according to claim 1 and a metal ion.

11. The luminescent complex according to claim 10, where the metal ion is selected from the group consisting of Eu(III) and Tb(III).

12. The luminescent complex according to claim 10, wherein the metal ion is a lanthanide.

13. A method of making a compound according to claim 1, the method comprising:
alkylating a compound according to Formula I-C with a compound according to Formula IV to produce a first intermediate;
alkylating the first intermediate with a compound according to Formula V to produce a second intermediate; and
deprotecting the second intermediate to produce the compound according to Formula I or Formula II;
where Formula I-C is

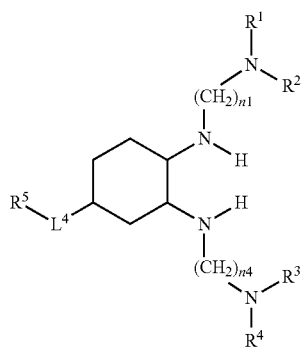

I-C where Formula IV and Formula V are

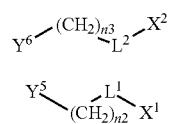

IV

V where n1 and n4 are 2;
where n2 and n3 are 1;
where $L^1$ and $L^2$ are none;

where $L^4$ is none or substituted and unsubstituted alkyl;

where $R^2$, $R^3$, and $R^4$ are each —$CH_2COOH$ or a —$CH_2COOH$ that has been protected with a carboxylic acid protecting group;

where $R^1$ is selected from the group consisting of —$CH_2COOH$, H, —$CH_2PO(OH)_2$, —$CH_2CONH_2$, substituted and unsubstituted alkyl, substituted and unsubstituted cycloalkyl, substituted and unsubstituted heterocyclyl, substituted and unsubstituted aryl, and substituted and unsubstituted heteroaryl groups, optionally that have been protected with one or more protecting groups;

where $R^6$ is selected from the group consisting of H, substituted and unsubstituted alkyl, halogen, CN, $CF_3$, acyl, —$SO_2NR^9R^{10}$, —$NR^9R^{10}$, —$OR^9$, —$SO_2R^9$, —$COOR^9$, —$SO_2OR^9$, —$OC(O)R^9$, —$C(O)NR^9R^{10}$—$NR^9C(O)R^{10}$, —$NR^9SO_2R^{10}$, —$NO_2$, —$C(O)NHNH_2$, —NCO, —NCS, —$N_3$, amino acid, peptidyl, phosporamidite, substituted and unsubstituted NHS ester, sulfonated NHS ester, haloacetyl, tyramine, biotin, estrogen, trimethoprim, methotrexate, benzyl guanine, benzyl cytosine, 1,2-dialkyl-sn-glycero-3-phosphoethanolamine, 1,2-dialkyl-sn-glycero-3-phospho-L-serine, 1,1',2,2'-tetraoleoyl cardiolipin, D-erythro-sphingosine, sphingosine-1-phosphocholine, and 5-cholesten-3β-ol, optionally that have been protected with one or more protecting groups;

where $R^9$ and $R^{10}$ are each independently selected from H, substituted and unsubstituted alkyl, substituted and unsubstituted aryl, substituted and unsubstituted heteroaryl and substituted and unsubstituted heterocyclyl, or $R^9$ and $R^{10}$, together with the atoms to which they are attached, form a 5- to 7 membered heterocyclyl or heteroaryl;

where $Y^5$ and $Y^6$ are each independently a halogen;

where $X^1$ and $X^2$ are each independently selected from the group consisting of —COOH, —$PO(OH)_2$, and a sensitizer so long as at least one of $X^1$ and $X^2$ is a sensitizer;

where each occurrence of the sensitizer is independently chosen from any one of the following formulas:

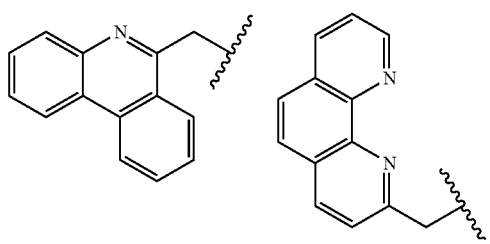

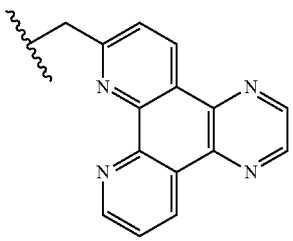

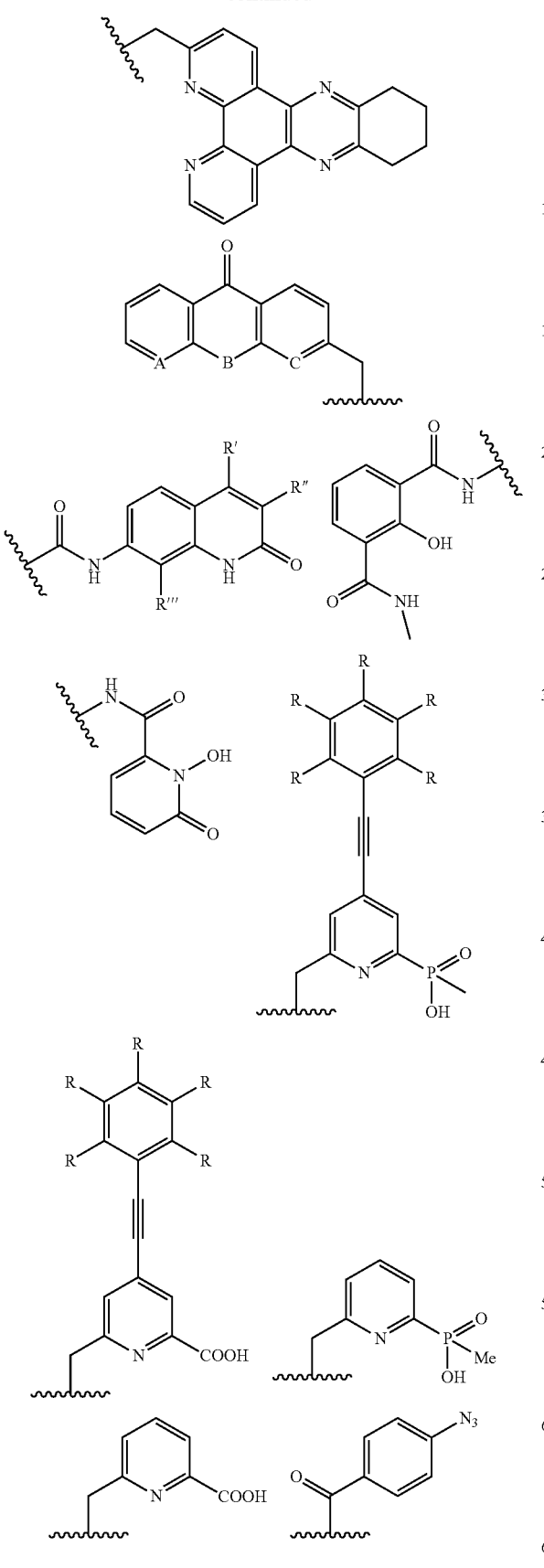
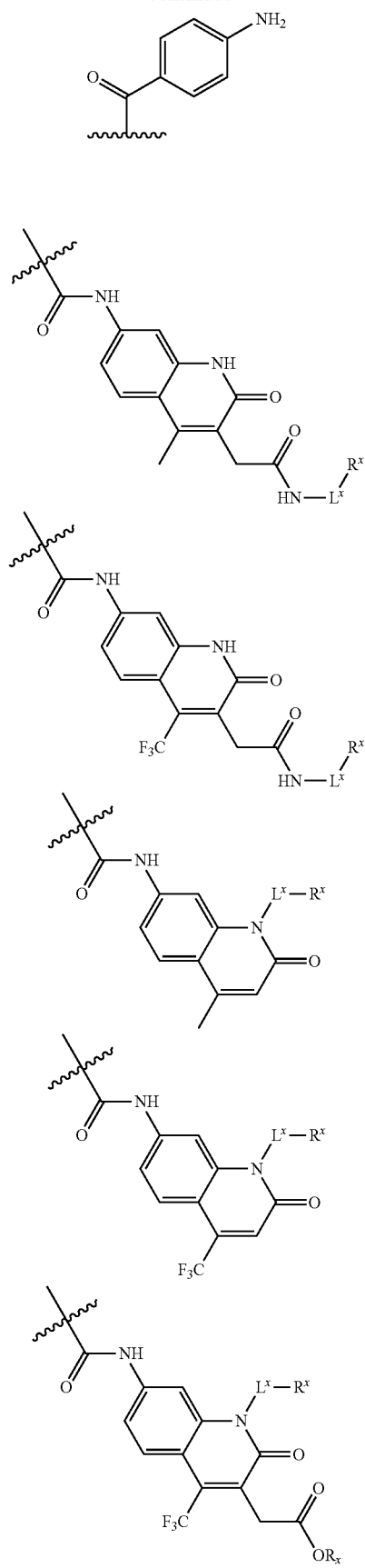

-continued

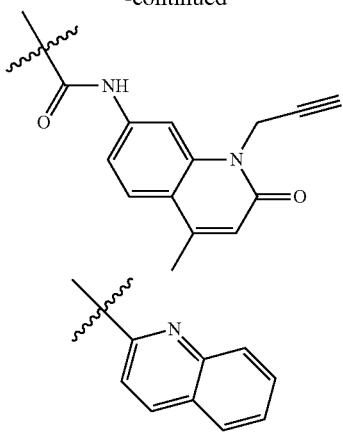

where A, B, and C are each independently selected from N and CH;

where R is independently selected at each occurrence from H and —OCH$_3$;

where R' is independently selected at each occurrence from —CH$_3$, —CF$_3$, and —CH$_2$COOH;

where R" is independently selected at each occurrence from H and —CH$_2$COOH;

where R'" is independently selected at each occurrence from H and —CH$_3$;

where L$^x$ is independently selected at each occurrence from none, substituted and unsubstituted alkyl, substituted and unsubstituted heteroalkyl, substituted and unsubstituted heteroaryl, and substituted and unsubstituted heterocycloalkyl; and where R$^x$ is independently selected at each occurrence from H, a halogen, substituted and unsubstituted alkyl, substituted and unsubstituted heteroalkyl, substituted and unsubstituted heteroaryl, and substituted and unsubstituted heterocycloalkyl.

14. The method according to claim 13, wherein the first alkylating step, the second alkylating step, or both comprise protecting one or more of R$^1$, R$^2$, R$^3$, and R$^4$ with a protecting group.

15. The method according to claim 13, wherein R$^2$, R$^3$, and R$^4$ are each —CH$_2$COOtBu.

16. The method according to claim 13, wherein R$^1$ is —CH$_2$COOtBu.

17. The method according to claim 13, wherein one or both of Y$^5$ and Y$^6$ are Cl.

* * * * *